(12) United States Patent
Desarbre et al.

(10) Patent No.: US 8,901,293 B2
(45) Date of Patent: *Dec. 2, 2014

(54) USEFUL COMBINATIONS OF MONOBACTAM ANTIBIOTICS WITH BETA-LACTAMASE INHIBITORS

(75) Inventors: Eric Desarbre, Mulhouse (FR); Bérangére Gaucher, Mulhouse (FR); Malcolm G. P. Page, Basel (CH); Patrick Roussel, Mulhouse (FR)

(73) Assignee: Basilea Pharmaceutica AG, Basel (CH)

( * ) Notice: Subject to any disclaimer, the term of this patent is extended or adjusted under 35 U.S.C. 154(b) by 1718 days.

This patent is subject to a terminal disclaimer.

(21) Appl. No.: 12/086,270

(22) PCT Filed: Dec. 7, 2006

(86) PCT No.: PCT/CH2006/000685
§ 371 (c)(1),
(2), (4) Date: Sep. 22, 2009

(87) PCT Pub. No.: WO2007/065288
PCT Pub. Date: Jun. 14, 2007

(65) Prior Publication Data
US 2010/0056478 A1 Mar. 4, 2010

(30) Foreign Application Priority Data

Dec. 7, 2005 (EP) .................... 05026699
Mar. 27, 2006 (EP) .................... 06006291

(51) Int. Cl.
| | | |
|---|---|---|
| C07D 205/08 | (2006.01) | |
| A61K 31/69 | (2006.01) | |
| A61K 31/675 | (2006.01) | |
| A61K 31/43 | (2006.01) | |
| A01N 43/00 | (2006.01) | |
| A61K 31/407 | (2006.01) | |
| A61K 45/06 | (2006.01) | |
| C07D 401/14 | (2006.01) | |
| A61K 31/4436 | (2006.01) | |
| C07D 487/04 | (2006.01) | |
| C07D 403/12 | (2006.01) | |
| A61K 31/427 | (2006.01) | |
| C07D 413/14 | (2006.01) | |
| C07D 417/14 | (2006.01) | |
| A61K 31/545 | (2006.01) | |
| A61K 31/662 | (2006.01) | |
| C07D 471/04 | (2006.01) | |

(52) U.S. Cl.
CPC .......... *C07D 403/12* (2013.01); *A61K 31/407* (2013.01); *A61K 45/06* (2013.01); *C07D 401/14* (2013.01); *A61K 31/43* (2013.01); *A61K 31/4436* (2013.01); *C07D 487/04* (2013.01); *A61K 31/427* (2013.01); *A61K 31/69* (2013.01); *C07D 413/14* (2013.01); *C07D 417/14* (2013.01); *A61K 31/545* (2013.01); *A61K 31/662* (2013.01); *C07D 471/04* (2013.01)
USPC .............. 540/355; 540/364; 514/64; 514/79; 514/195; 514/209

(58) Field of Classification Search
CPC ....... A61K 31/69; A61K 38/00; A01N 55/08; C07K 5/06191
USPC ................................. 540/355, 364; 514/64
See application file for complete search history.

(56) References Cited

U.S. PATENT DOCUMENTS

| | | |
|---|---|---|
| 4,181,800 A | 1/1980 | Kamiya |
| 4,201,779 A | 5/1980 | Bormann |
| 4,267,176 A | 5/1981 | Kamiya |
| 4,348,518 A | 9/1982 | Montavon |
| 4,394,504 A | 7/1983 | Commons |
| 4,427,690 A | 1/1984 | Cole |
| 4,432,970 A | 2/1984 | Kellogg |
| 4,499,016 A | 2/1985 | Breuer |
| 4,572,801 A | 2/1986 | Matsuo |
| 4,638,061 A | 1/1987 | Slusarchyk |
| 4,775,670 A | 10/1988 | Sykes |
| 4,794,108 A | 12/1988 | Kishimoto |
| 4,798,828 A | 1/1989 | Osborne |
| 4,826,833 A | 5/1989 | Chen |
| 4,939,253 A | 7/1990 | Breuer |
| 5,137,884 A | 8/1992 | Andrus |
| 5,644,053 A | 7/1997 | Hubschwerlen |
| 5,686,441 A | 11/1997 | Maiti |

(Continued)

FOREIGN PATENT DOCUMENTS

| | | |
|---|---|---|
| DE | 3229439 | 2/1983 |
| EP | 0017485 | 10/1980 |
| EP | 0051381 | 5/1982 |
| EP | 0055465 | 7/1982 |
| EP | 0062876 | 10/1982 |

(Continued)

OTHER PUBLICATIONS

Tanaka et al.; "In Vitro Evaluation of Tigemonam, a Novel Oral Monobactam"; 1987; Antimicrobial Agents and Chemotherapy; 31(2): 219-225.*

(Continued)

*Primary Examiner* — Shirley V Gembeh

(57) ABSTRACT

New monobactam antibiotics compounds which contain an 3-amino-azetidin-2-one ring and are active against gram-negative bacteria, wherein the compounds include the compound 2-(2-amino-thiazol-4-yl)-2-[(Z)-(1H,4H-1,5-dihydroxy-4-oxo-pyridin-2-yl)methoxyimino]-N-[3(S)-1-oxysulfonyl-2,2-dimethyl-4-oxo-azetidin-3-yl]acetamide.

12 Claims, No Drawings

(56) References Cited

U.S. PATENT DOCUMENTS

| | | | |
|---|---|---|---|
| 6,566,355 | B1 | 5/2003 | Hubschwerlen |
| 2004/0029836 | A1 | 2/2004 | Besterman |
| 2004/0082546 | A1 | 4/2004 | Besterman |
| 2004/0157826 | A1 | 8/2004 | Lampilas |
| 2005/0020572 | A1 | 1/2005 | Aszodi |

FOREIGN PATENT DOCUMENTS

| | | |
|---|---|---|
| EP | 0096296 | 12/1983 |
| EP | 0135194 | 3/1985 |
| EP | 0251299 | 1/1988 |
| EP | 0272016 | 6/1988 |
| EP | 0333154 | 9/1989 |
| EP | 0508234 | 10/1992 |
| EP | 0544307 | 6/1993 |
| EP | 0640607 | 3/1995 |
| GB | 1519495 | 7/1978 |
| GB | 2102423 | 2/1983 |
| WO | 9315078 | 8/1993 |
| WO | 9533724 | 12/1995 |
| WO | 9617849 | 6/1996 |
| WO | 9706172 | 2/1997 |
| WO | 9847895 | 10/1998 |
| WO | 9910324 | 3/1999 |
| WO | 0076970 | 12/2000 |
| WO | 0210172 | 2/2002 |
| WO | 0222613 | 3/2002 |

OTHER PUBLICATIONS

Vippagunta et al.; "Crystalline solids"; 2001I Advanced Drug Reviews; 48: 3-26.*

Madsen et al, N-Methyl-D-aspartic acid receptor agonists : resolution, absolute stereochemistry, and pharmacology of the enantiomers of 2-amino-2-(3-hydroxy-5-methyl-4-isoxazolyl)acetic acid, Journal of medicinal chemistry, 1996, vol. 39, No. 1, pp. 183-190.

Madsen et al, Synthesis and single cell pharmacology of potential heterocyclic bioisosteres of the excitatory amino acid antagonist glutamic acid diethyl ester, Acta Chem Scand. Jan. 1990; 44(1):96-102.

Matsuo et al, Synthesis and antibacterial activity of 3-acylamino-3-methoxy-2-azetidinone-1-sulfonic acid derivatives, Chem. Pharm. Bull (Tokyo), Jul. 1983;31 (7):2200-8.

Mattingly et al, Chiral syntheses of protected 3-amino-4-(alkoxycarbonyl)-2-azetidinones from b-hydroxyaspartic acid, J. Org. Chem. 1983, 48, 3556-3559.

Mattingly et al, Synthesis of 2-azetidinones from serinehydroxamates: approaches to the synthesis of 3-aminonocardicinic acid, Journal of Organic Chemistry 1981, 46, (8), 1557-64.

Mattingly et al, Titanium trichloride reduction of substituted N-hydroxy-2-azetidinones and other hydroxamic acids, J. Org. Chem., 1980, 45, (3), pp. 410-415.

McLamore et al, The Preparation and Rearrangement of Allyl Kojate, J. Am. Chem. Soc.; 1956; 78(12); 2816-2818.

Miller et al, Synthesis of. beta.-lactams from substituted hydroxamic acids, J. Am. Chem. Soc. 1980, 102, pp. 7026-7032.

Nishigaki et al, Condensation Reactions of Ethyl Ethoxymethylenecyanoacetate with Amidines, Chemical & pharmaceutical bulletin, vol. 18, No. 5 (1970) pp. 1003-1007.

Pace et al, The monoethyl ester of meconic acid is an active site inhibitor of HCV NS5B RNA-dependent RNA polymerase, Bioorg Med. Chem Lett. Jun. 21, 2004;14(12):3257-61.

Palandoken et al, A facile synthesis of (tert-alkoxy)amines, Tetrahedron Letters, vol. 46, Issue 39, Sep. 26, 2005, pp. 6667-6669.

Phillips et al, SYN-1012 : A new β-lactamase inhibitor of penem skeleton, Journal of Antibiotics, 1997, vol. 50, No. 4, pp. 350-356.

Roemmele et al, Chirospecific synthesis of beta.-hydroxy. alpha.-amino acids, J. Org. Chem. 1989, 1866-1875.

Rzepecki et al, New heterocyclic beta-sheet ligands with peptidic recognition elements, J. Org. Chem. Aug. 6, 2004;69(16):5168-78.

Saito et al, Diethyl (2S,3R)-2-(N-tert-Butoxycarbonyl)Amino-3-Hydroxysuccinate, Organic Syntheses, Coll. vol. 9, p. 220 (1998).

Sakaiani et al, One-pot conversion of N-benzyloxycarbonyl group into N-tert-butoxycarbonyl group, Tetrahedron Letters, vol. 29, Issue 24, 1988, pp. 2983-2984.

Salituro et al, Total Syntheses of (−)-Nocardicins A-G: A Biogenetic Approach, J. Am. Chem. Soc., 1990, 112, 760-770.

Saunders et al, Novel quinuclidine-based ligands for the muscarinic cholinergic receptor, J. Med. Chem. Apr. 1990; 33(4):1128-38.

Schaefer, Synthesis of the s-Triazine System. VI. Preparation of Unsymmetrically Substituted s-Triazines by Reaction of Amidine Salts with Imidates, J. Org. Chem., vol. 27, Oct. 1962, pp. 3608-3613.

Seebach et al, Addition of chiral glycine, methionine, and vinylglycine enolate derivatives to aldehydes and ketones in the preparation of enantiomerically pure a-amino-p-hydroxy acids, Helvetica chimica acta, 1987, vol. 70, No. 1, pp. 237-261.

Sendai et al, Chemical modification of sulfazecin. Synthesis of 4-(substituted methyl)-2-azetidinone-1-sulfonic acid derivatives, J. Antibiot (Tokyo). Mar. 1985; 38(3):346-71.

Sharma et al, Studies in Potential Filaricides. Part 19. Synthesis of 1-Methyl-4-Substituted Carbonylpiperazines As Diethylcarbamazine Analogs. & Ind. J. Chem., Sect. B; 1987, 26B(8), 748-51.

Shen et al, New synthesis of dialkyl fluoroalkynylphosphonates, J. Chem. Soc., Perkin Trans. 1, 1993, 2153-2154.

Sigman et al, A General Catalyst for the Asymmetric Strecker Reaction, Angew. Chem. Int. Ed. Engl. Apr. 2000;39(7):1279-1281.

Singh et al, Regioselective Activation of Aminothiazole(iminoxyacetic acid)acetic Acid: An Efficient Synthesis of the Monobactam Aztreonam, Org. Proc. Res. Dev., 6 (6), 863-868, 2002.

Skotnicki et al, Synthesis and biological evaluation of a 4-fluoromethyl monobactam analog, J. Antibiot (Tokyo), Sep. 1983; 36(9):1201-4.

Slusarchyk et al, β-Lactam synthesis: chemospecific sulfonation and cyclization of the β-hydroxyvaline nucleus, Tetrahedron letters, 1986, vol. 27, No. 25, pp. 2789-2792.

Stefanic et al, Aspartate and glutamate mimetic structures in biologically active compounds, Current medicinal chemistry, 2004, vol. 11, No. 8, pp. 945-968.

Sznaidman et al, Novel selective small molecule agonists for peroxisome proliferator-activated receptor delta (PPARdelta)—synthesis and biological activity, Bioorg. Med. Chem. Lett., May 5, 2003;13(9):1517-21.

Tatsuta et al, Practical Preparation of (Z)-2-(5-Amino-1,2,4-thiadiazol-3-yl)-2-methoxyiminoacetic Acid: A Side-Chain of the Fourth Generation of Cephem Antibiotics, Bulletin of the Chemical Society of Japan, vol. 67 (1994), No. 6, pp. 1701-1707.

Taylor et al, The Reaction of Malononitrile with Hydrazines, J. Am. Chem. Soc., vol. 81, No. 10: May 20, 1959, pp. 2452-2455.

Taylor et al, The Reaction of Malononitrile with Substituted Hydrazines: New Routes to 4-Aminopyrazolo[3,4-d] pyrimidines, J. Am. Chem. Soc.; 1959; 81(10) pp. 2456-2464.

Thomas et. al., "Heilmittelchemische Studien in der heterocyclischen Reihe: Die Reaktion von Kojisaure mit Hydrazin: Umsetzung von Kojisaureathern mit Hydrazin", Helv. Chim. Acta 1960, 469. An English Summary is on p. 477.

Tondi et al, Structure-based design and in-parallel synthesis of inhibitors of AmpC β-lactamase, Chemistry & Biology, vol. 8, Issue 6, 2001, pp. 593-610.

Wei et al, Synthesis of chiral. beta.-lactams using L-ascorbic acid, J. Org. Chem. 1985,50, 3462-3467.

Weinheimer et al, Naturally Occurring Cembranes, Fortschr. Chem. Org. Naturst., 36, 1979, p. 327.

Williams et al, Grignard reactions to chiral oxazolidine aldehydes, Tetrahedron, vol. 52, Issue 36, Sep. 2, 1996, pp. 11673-11694.

Woulfe et al, Synthesis and biological activity of substituted [[3(S)-(acylamino)-2-oxo-1-azetidinyl]oxy]acetic acids. A new class of heteroatom-activated beta-lactam antibiotics, J. Med. Chem. Oct. 1985; 28(10):1447-53.

Yarovenko et al, Synthesis of Oxamic Acids Thiohydrazides and Carbamoyl-1,3,4-thiadiazoles, Russian Journal of Organic Chemistry, vol. 39, No. 8 / Aug. 2003, pp. 1133-1139.

(56) References Cited

OTHER PUBLICATIONS

Young et al, Novel synthesis of oxadiazoles via palladium catalysis, Tetrahedron Letters, vol. 39, Issue 23, Jun. 4, 1998, pp. 3931-3934.
Yoshida et al, Studies on monocyclic beta-lactam antibiotics. II. Synthesis and antibacterial activity of 3-acylamino-2-azetidinone-1-oxysulfonic acids, J. Antibiot (Tokyo). Nov. 1985; 38 (11):1536-49.
Yoshida et al, Studies on monocyclic beta-lactam antibiotics. III. Synthesis and antibacterial activity of N-(aromatic heterocyclic substituted)azetidin-2-ones, J. Antibiot (Tokyo). Jan. 1986; 39(1):76-89.
Zhang et al, A Novel and Practical Synthesis of 3-Unsubstituted Indolizines, Synthesis 2000; No. 12, 1733-1737.
The International Search Report and Written Opinion by the International Searching Authority, issued on Apr. 18, 2008, in the PCT application No. PCT/CH2006/000685.
Piddock et al, Activity of 13 β-lactam agents combined with BRL 42715 against β-lactamase producing Gram-negative bacteria compared to combinations with clavulanic acid, tazobactam and sulbactam, Journal of Antimicrobial Chemotherapy (1993) 31, 89-103.
Fournier et al, In-vitro susceptibility of Klebsiella oxytoca strains to 13 β-lactams in the presence and absence of β-lactamase inhibitors, Journal of Antimicrobial Chemotherapy (1996) 37, 931-942.
Gutmann et al, SHV-5, a novel SHV-type beta-lactamase that hydrolyzes broad-spectrum cephalosporins and monobactams, Antimicrob Agents Chemother. Jun. 1989; 33(6): 951-956.
Amicosante et al, Do inert beta-lactamase inhibitors act as synergizers of beta-lactam antibiotics? Utility of boric and boronic acids, J. Chemother. Dec. 1989;1(6):394-8.
Heinze-Krauss et al, Structure-based design of β-lactamase inhibitors. 1. Synthesis and evaluation of bridged monobactams. Journal of Medicinal Chemistry 41, 1998, pp. 3961-3971.
Hubschwerlen et al, Structure-based design of β-lactamase inhibitors. 2. Synthesis and evaluation of bridged sulfactams and oxamazins, Journal of Medicinal Chemistry 41, 1998, pp. 3972-3975.
Georgopapadakou, N H: Beta-lactamase inhibitors: evolving compounds for evolving resistance targets, Expert Opin. Investig. Drugs 13, 2004, pp. 1307-1318.
Xiong et al, A Klebsiella pneumoniae producing three kinds of class A beta-lactamases encoded by one single plasmid isolated from a patient in Huashan Hospital, Shanghai, China, International Journal of Antimicrobial Agents vol. 23, Issue 3, Mar. 2004, pp. 262-267.
Buynak et al, The synthesis and evaluation of 6-alkylidene-2'beta-substituted penam sulfones as beta-lactamase inhibitors, Bioorganic & Medicinal Chemistry Letters vol. 9, Issue 14, Jul. 19, 1999, pp. 1997-2002.
Gottstein et al, Synthesis and. beta.-lactamase inhibitory properties of 2. beta acyloxymethyl-2-Methylpenam-3-alpha-carboxylic-acid 11-Dioxides, Journal of Medicinal Chemistry, 1985, vol. 28, pp. 518-522.
Sumita et al, Structure-activity Relationships for Interactions between Carbapenems and Beta-Lactamases, The Journal of Antibiotics, vol. 48, No. 2(1995) pp. 188-190.
Sotto et al, In-vitro evaluation of beta-lactamase inhibition by latamoxef and imipenem, Journal of Antimicrobial Chemotherapy (1996) 37, 697-701.
Ageno et al, Enantiospecific and diastereoselective synthesis of 4,4-disubstituted-3-amino-2-azetidinones, starting from D-serine, Tetrahedron, vol. 51, Issue 29, Jul. 17, 1995, pp. 8121-8134.
Aggarwal et al, Catalytic, Asymmetric Sulfur Ylide-Mediated Epoxidation of Carbonyl Compounds: Scope, Selectivity, and Applications in Synthesis, Acc. Chem. Res., 37 (8), 611-620, 2004.
Amici et al, Enantioselective Synthesis of (S)-2-Amino-3-(3-Hydroxy-5-methylisoxazol-4-yl)propanoic Acid (S)-AMPA, Synthesis Oct. 1996; 1177-1179.
Badalassi et al, Fluorescence Assay and Screening of Epoxide Opening by Nucleophiles, European Journal of Organic Chemistry, vol. 2004 Issue 12, pp. 2557-2566.

Bapat et al, N-Oxides and Related Compounds. Part 58. Some Precursors of Pyridinum Methylide, J. Chem. Soc., Perkin Trans. I. 1977, 1692.
Barbachyn et al, Identification of phenylisoxazolines as novel and viable antibacterial agents active against Gram-positive pathogens, J. Med. Chem. Jan. 16, 2003;46(2):284-302.
Bartholomew et al, Chloro (ethoxycarbonyl)methyleneiminium salts—versatile electrophilic intermediates for heterocyclic synthesis, Tetrahedron Letters, vol. 20, Issue 30, 1979, pp. 2827-2830.
Basavaiah et al, A study toward understanding the role of a phosphorus stereogenic center in (5S)-1,3-diaza-2-phospha-2- oxo-3-phenylbicyclo(3.3.0)octane derivatives as catalysts in the borane-mediated asymmetric reduction of prochiral ketones, Tetrahedron: asymmetry, 2005, vol. 16, No. 24, pp. 3955-3962.
Borg et al, Synthesis of 1, 2, 4-Oxadiazole-, 1, 3, 4-Oxadiazole-, and 1, 2, 4-Triazole-Derived Dipeptidomimetics, J. Org. Chem. 1995,60, 3112-3120.
Breuer et al, [(2-Oxo-1-azetidinyl)oxy]acetic acids: a new class of synthetic monobactams, J. Antibiot (Tokyo),Jun. 1985; 38(6):813-8.
Buynak et al., Synthesis and Biological Activity of 7-Alkylidenecephalosporins, J. Med. Chem. 1995, 38, 1022-1034.
Buynak et al., The synthesis and evaluation of 2-substituted-7-(alkylidene)cephalosporin sulfones as beta-lactamase inhibitors, Bioorganic & Medicinal Chemistry Letters, vol. 10, Issue 9, May 1, 2000, pp. 847-851.
Buynak et al., The synthesis and evaluation of 3-substituted-7-(alkylidene)cephalosporin sulfones as beta-lactamase inhibitors, Bioorganic & Medicinal Chemistry Letters, vol. 10, Issue 9, May 1, 2000, pp. 853-857.
Buynak et al., The Synthesis and Lactamase Inhibitory Activity of 6-(Carboxymethylene)penicillins and 7-(Carboxymethylene)cephalosporins, Bioorg. Med. Chem. Lett. 1995, 5, 1513-1518.
Campbell et al, Studies on γ-Pyrones. I. Derivatives of Kojic Acid, The Journal of Organic Chemistry, J. Org. Chem., vol. 15, No. 1: Jan. 1950, pp. 221-226.
Castro et al, Advances in the synthesis and recent therapeutic applications of 1,2,4-thiadiazole heterocycles, Bioorganic & medicinal chemistry, 2006, vol. 14, No. 5, pp. 1644-1652.
Choong et al, Synthesis of Alkoxylamines by Alkoxide Amination with 3,3'-Di-tert-butyloxaziridine, J. Org. Chem. Sep. 3, 1999; 64(18):6528-6529.
Clark, Novel adducts in the pteridine field, Tetrahedron Letters, vol. 8, Issue 12, 1967, pp. 1099-1102.
Coleman et al, In vitro evaluation of BRL 42715, a novel beta-lactamase inhibitor, Antimicrob Agents Chemother, Sep. 1989; 33(9): 1580-1587.
Coleman et al, Pharmacokinetic studies and renal dehydropeptidase stability of the new beta-lactamase inhibitor BRL 42715 in animals, Antimicrob Agents Chemother. Sep. 1991; 35(9): 1748-1752.
Csendes et al, Cephalosporin antibiotics. Synthesis and antimicrobial activity of 7 beta-[2-(5-amino-1,2,4-thiadiazol-3-yl)-2-oxyiminoacetamido]cephalosporin derivatives, J. Antibiot (Tokyo). Aug. 1983; 36(8):1020-33.
Dettwiler et al, Serine as Chiral Educt for the Practical Synthesis of Enantiopure N-Protected -Hydroxyvaline, J. Org. Chem., 68 (1), 177-179, 2003.
Dornow et al, Über einige Analoga des Thiamins. Zur Strukturspezifitat des Vitamins B1, IX. Mitteilung, Justus Liebigs Annalen der Chemie, vol. 588 Issue 1, pp. 45-61, with a partial English translation and a concise explanation.
Dost et al, Darstellung von 3-substituierten 5-Amino-1,2,4-oxadiazolen aus Amidoximen mi Bromcyan, Z. Chem. 1975, 233, with an English translation.
Eckstein, et al., A facile rearrangement of Heterocycles, pyridinecarbohydroxamic acids in formamide, Heterocycles, vol. 20, No. 10, 1983, pp. 1899-1901.
Floyd et al., Monobactams. Preparation of (S)-3-Amino-2-Oxoazetidine-1-Sulfonic Acids from L-.alpha.-Amino-.beta.-Hydroxy Acids via Their Hydroxamic Esters, J. Org. Chem. 1982, 47, 5160-5167.

(56) References Cited

OTHER PUBLICATIONS

Frohlich et al, Belitrage zur Chemic N-organylsubstituierter Metallamide; Athyl-vanadin-tris-diathylamid, Z. Chem. 1975, 233, with an English translation.

Fuerst et al, Thiourea-Catalyzed Enantioselective Cyanosilylation of Ketones, J. Am. Chem. Soc., 2005, 127, 8964-8965.

Glinka et al, Relationships between structure, antibacterial activity, serum stability, pharmacokinetics and efficacy in 3-(heteroarylthio)cephems. Discovery of RWJ-333441 (MC-04,546), Bioorganic & Medicinal Chemistry, vol. 11, Issue 4, Feb. 20, 2003, pp. 591-600.

Gordon et al, O-Sulfated .beta.-lactam hydroxamic acids (monosulfactams). Novel monocyclic .beta.-lactam antibiotics of synthetic origin, J. Am. Chem. Soc., vol. 104, No. 22: Nov. 3, 1982, pp. 6053-6060.

Goto et al, Studies of 7 beta-[2-(aminoaryl)acetamido]-cephalosporin derivatives. I. Synthesis and structure-activity relationships in the aminopyridine series, J. Antibiot (Tokyo). May 1984; 37(5):532-45.

Goto et al, Studies of 7 beta-[2-(aminoaryl)acetamido]-cephalosporin derivatives. II. Synthesis and structure-activity relationships in the aminopyrimidine series, J. Antibiot (Tokyo). May 1984;37(5):546-56.

Goto et al, Studies of 7 beta-[2-(aminoaryl)acetamido]-cephalosporin derivatives. III. Synthesis and structure-activity relationships in the aminothiadiazole series, J. Antibiot (Tokyo). May 1984; 37(5):557-71.

Hanson et al, An Expedient Synthesis of ()-2-Amino-3-(3-Hydroxy-5-Methylisoxazol-4-yl) Propionic Acid Hydrobromide Via a 3-Bromoisoxazole Intermediate, Journal of heterocyclic chemistry, 1997, vol. 34, No. 1, pp. 345-348.

Herges et al, Design of a Neutral Macrocyclic Ionophore: Synthesis and Binding Properties for Nitrate and Bromide Anions, European Journal of Organic Chemistry, vol. 2002 Issue 17, pp. 3004-3014.

Hrabalek et al, [1-Alkyl(aryl)tetrazol-5-ylthio]acetic Acids, Russian Journal of Organic Chemistry, vol. 36, No. 5, 2000, pp. 761-762.

Huck et al, From beta-N-tert-butyloxycarbonyl N-carboxyanhydrides to beta-aminoacid derivatives, J. Pept Res. Dec. 2003; 62(6):233-7.

Ishikawa et al, Studies on anti-Mrsa parenteral cephalosporins, II. Synthesis and antibacterial activity of 7β-12-(5-amino-1,2,4-thiadiazol-3-yl)-2(Z)-alkoxyiminoacetamido]-3-(substituted imidazo[1,2-b]pyridazinium-1-yl)methyl-3-cephem-4-carboxylates and related compounds, Journal of antibiotics, 2000, vol. 53, No. 10, pp. 1071-1085.

Iwamatsu et al, A new antipseudomonal cephalosporin CP6162 and its congeners, J. Antibiot (Tokyo). Nov. 1990; 43 (11):1450-63.

Johansen et al, Excitatory amino acid receptor ligands : Resolution, absolute stereochemistry, and enantiopharmacology of 2-amino-3-(4-butyl-3-hydroxyisoxazol-5-yl)propionic acid, Journal of medicinal chemistry, 1998, vol. 41, No. 6, pp. 930-939.

Kawulka et al, Structure of subtilosin A, a cyclic antimicrobial peptide from *Bacillus subtilis* with unusual sulfur to alpha-carbon cross-links: formation and reduction of alpha-thio-alpha-amino acid derivatives, Biochemistry, Mar. 30, 2004;43 (12):3385-95.

Kim et al, Synthesis and antibacterial activity of cephalosporins having hydroxamic acid at C-7 position, Bioorganic & Medicinal Chemistry Letters, vol. 6, Issue 17, Sep. 3, 1996, pp. 2077-2080.

Kishimoto et al, Chemical modification of sulfazecin. Synthesis of 4-methoxycarbonyl-2-azetidinone-1-sulfonic acid derivatives, Chem. Pharm. Bull (Tokyo), Jul. 1984;32 (7):2646-59.

Kofman et al, Synthesis and Some Transformations of 3-Substituted 1,2,4-Triazole-5-Acetic Acids, Russian journal of organic chemistry, 1995, vol. 31, No. 2, pp. 240-244.

Kristinsson et al, Synthese von heterocyclen. V. 1, 3, 4-thiadiazol-2 (3 H)-one, Helvetica Chimica Acta, vol. 65, Issue 8, 1982, pp. 2606-2621.

Kronenthal et al, Oxidative N-Dearylation of 2-Azetidinones. p-Anisidine as a Source of Azetidinone Nitrogen, J. Org. Chem., 47, 2765-2768 (1982).

Liu et al, Design, synthesis, and evaluation of novel 2-substituted 3-hydroxypyridin-4-ones: Structure-activity investigation of metalloenzyme inhibition by iron chelators, Journal of medicinal chemistry, 2002, vol. 45, No. 3, pp. 631-639.

Liu et al, Synthesis of 2-amido-3-hydroxypyridin-4(1H)-ones : Novel iron chelators with enhanced pFe3+ values, Bioorganic & medicinal chemistry, 2001, vol. 9, No. 3, pp. 563-573.

Lubell et al, N-(9-phenylfluoren-9-yl)-.alpha.-amino ketones and N-(9-phenylfluoren-9-yl)-.alpha.-amino aldehydes as chiral educts for the synthesis of optically pure 4-alkyl-3-hydroxy-2-amino acids. Synthesis of the C-9 amino acid MeBmt present in cyclosporin, J. Org. Chem.; 1990; 55(11); 3511-3522.

Ma et al, Design, synthesis, physicochemical properties, and evaluation of novel iron chelators with fluorescent sensors, Journal of medicinal chemistry, 2004, vol. 47, No. 25, pp. 6349-6362.

\* cited by examiner

USEFUL COMBINATIONS OF MONOBACTAM ANTIBIOTICS WITH BETA-LACTAMASE INHIBITORS

FIELD OF THE INVENTION

The present invention is concerned with pharmaceutical compositions and methods for treating infections caused by pathogenic Gram-negative bacteria.

BACKGROUND OF THE INVENTION

β-Lactam antibiotics have been widely used for the treatment of bacterial infections both in hospitals and in the general public. There are several classes of β-lactam antibiotics that have found clinical application, these include the penicillins, cephalosporins, cephamycins, carbacephems, oxacephems, carbapenems and monobactams.

The efficiency of all of these classes to cure bacterial infections has been impaired by the appearance of bacteria that are resistant towards the antibiotics. The prevalent cause of this resistance in Gram-negative bacteria is the expression by the bacteria of enzymes known as β-lactamases that are able to hydrolyse the β-lactam antibiotics rendering them inactive. Bacteria are able to produce a variety of β-lactamases, including penicillinases, cephalosporinases, cephamycinases, carbapenemases, monobactamases, broad-spectrum β-lactamases and extended-spectrum β-lactamases.

The possibility of rescuing individual β-lactam antibiotics by combination with a β-lactamase inhibitor that inactivates the β-lactamase before it can hydrolyse the β-lactam antibiotic has been demonstrated with clinically useful combinations between penicillins such as amoxicillin, ampicillin and ticarcillin and β-lactamase inhibitors such as clavulanic acid, sulbactam and tazobactam. Further, potential combinations have been described involving cephalosporins and newly developed β-lactamase inhibitors including bridged monobactams, penam sulfones, phosphonate esters, exomethylene penams and diazabicyclooctane derivatives.

Monobactams have been regarded as stable towards many β-lactamases. However, there are now many strains of Gram-negative bacteria that exhibit β-lactamase-mediated resistance towards the monobactam antibiotics (aztreonam, carumonam and tigemonam).

The present invention aims to provide improved medicaments with novel monobactam antibiotics and combinations of monobactam antibiotics with β-lactamase inhibitors that are active against aerobic Gram-negative bacteria that are resistant against treatments with monobactam antibiotics.

SUMMARY OF THE INVENTION

The objective set is solved by a pharmaceutical composition, comprising a combination of
a) an antibiotically active compound of the following formula I:

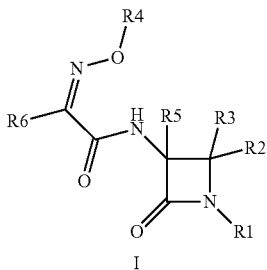

in which
R1 signifies $SO_3H$, $OSO_3H$, CRaRa'COOH, OCRaRa'COOH, 5-tetra-zolyl, $SO_2NHRb$ or CONHRc,
  wherein Ra and Ra' are independently selected from hydrogen; alkyl; allyl; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; alkylamino; dialkylamino; alkoxyalkyl and a 5-6 membered heteroaromatic ring which may be substituted with 1 to 4 substituents selected from alkyl, hydroxyl, alkoxy, amino, alkylamino, dialkylamino and halogen;
  wherein Rb is hydrogen; alkyl; alkoxycarbonyl; alkylaminocarbonyl; benzylaminocarbonyl in which the benzyl may be substituted with 1 to 5 substituents selected from alkyl, hydroxyl, alkoxy, amino, alkylamino, dialkylamino and halogen; or phenylaminocarbonyl in which the phenyl may be substituted with 1 to 5 substituents selected from alkyl, hydroxyl, alkoxy, amino, alkylamino, dialkylamino and halogen;
  wherein Rc is hydrogen; alkyl; phenyl which may be substituted with 1 to 5 substituents selected from alkyl, hydroxyl, alkoxy, amino, alkylamino, dialkylamino and halogen; benzyl which may be substituted with 1 to 5 substituents selected from alkyl, hydroxyl, alkoxy, amino, alkylamino, dialkylamino and halogen; alkoxycarbonyl; $SO_2$phenyl; $SO_2$NHalkyl; or a 5-6 membered heteroaromatic ring which may be substituted with 1 to 4 substituents selected from alkyl, hydroxyl, alkoxy, amino, alkylamino, dialkylamino and halogen;
R2 and R3 independently signify hydrogen; alkyl; alkenyl; alkynyl; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; azido; halogen; dihalogenomethyl; trihalogenomethyl; alkoxycarbonyl; carboxyl; sulfonyl or $CH_2X1$,
  wherein X1 is azido; amino; halogen; hydroxyl; cyano; carboxyl; aminosulfonyl; alkoxycarbonyl; alkanoylamino; phenylaminocarbonyl; alkylaminocarbonyl; aminocarbonyl; carbamoyloxy; alkylaminosulfonyl; phenylaminosulfonyl in which the phenyl may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; or benzyl which may be substituted with 1 to 5 substituents selected from alkyl, hydroxyl, alkoxy, amino, alkylamino, dialkylamino and halogen;
R4 signifies hydrogen; alkyl; C(Rx)(Ry)Z,
  wherein Rx and Ry are independently selected from hydrogen; alkyl; allyl; $(C_3-C_6)$cycloalkyl; phenyl which may be substituted with 1 to 5 substituents selected from alkyl, hydroxyl, alkoxy, amino, alkylamino, dialkylamino and halogen; $(C_2-C_7)$ alkene and $(C_2-C_7)$alkyne; or Rx and Ry taken together may form an alkylene bridge —$(CH_2)_n$— with n being an integer number from 2 to 6; and
  Z is COOH; $CH_2N(OH)COR'$ wherein
    R' is hydrogen, alkyl, alkylamino, alkoxy, benzyl which may be substituted with 1 to 5 substituents selected from alkyl, hydroxyl, alkoxy, amino, alkylamino, dialkylamino and halogen, phenyl which may be substituted with 1 to 5 substituents selected from alkyl, hydroxyl, alkoxy, amino, alkylamino, dialkylamino and halogen, or a 5-6 membered heteroaromatic ring which may be substituted with 1 to 4 substituents selected from alkyl, hydroxyl, alkoxy, amino, alkylamino, dialkylamino and halogen;

or Z is one of the following six groups

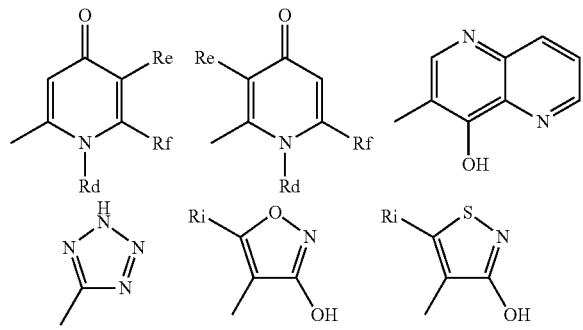

in which groups

Rd, Re and Rf are independently selected from hydrogen; alkyl; amino; monoalkylamino; carboxylaminoalkyl; alkoxycarbonyl; benzyl which may be substituted with 1 to 5 substituents selected from alkyl, hydroxyl, alkoxy, amino, alkylamino, dialkylamino and halogen; diphenylmethyl; trityl; and ORg wherein Rg is hydrogen; alkyl; benzyl which may be substituted with 1 to 5 substituents selected from alkyl, hydroxyl, alkoxy, amino, alkylamino and halogen; or phenyl which may be substituted with 1 to 5 substituents selected from alkyl, hydroxyl, alkoxy, amino, alkylamino and halogen;

or, when Re and Rf are vicinal substituents, Re and Rf taken together may also be —O—CH=CH—CH$_2$—, —O—CH$_2$—CH$_2$—O—, —CH$_2$—CH$_2$—CH$_2$—, —CH$_2$—CH$_2$—CH$_2$—CH$_2$—, —CH=CH—CH=CH— or —CH=C(OH)—C(OH)=CH—;

Ri is hydrogen; alkyl; alkylamino; alkoxy; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl and hydroxyl; or a 5-6 membered heteroaromatic ring which may be substituted with 1 to 5 substituents selected from alkyl, hydroxyl, alkoxy, amino, alkylamino, dialkylamino and halogen;

R5 signifies hydrogen, alkyl, halogenomethyl, dihalogenomethyl, trihalogenomethyl, alkoxy, formylamino or alkylcarbonylamino;

R6 signifies phenyl which may be substituted with 1 to 5 substituents selected from alkyl, hydroxyl, alkoxy, amino, alkylamino, dialkylamino and halogen; or a 5-6 membered heteroaromatic ring which may be substituted with 1 to 4 substituents selected from alkyl, hydroxyl, alkoxy, amino, alkylamino, carbonylamino and halogen;

or a pharmaceutically acceptable salt thereof;

and one or more β-lactamase inhibitors selected from the following groups b1) to b11):

b1) a bridged monobactam derivative of the following formula II:

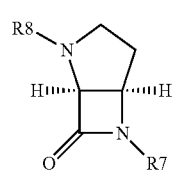

in which:

R7 signifies SO$_3$H, OSO$_3$H or OCRjRj'COOH,
wherein Rj and Rj' are independently selected from hydrogen; alkyl; phenyl which may be substituted with 1 to 5 substituents selected from alkyl, hydroxyl, alkoxy, amino, alkylamino, dialkylamino and halogen; benzyl which may be substituted with 1 to 5 substituents selected from alkyl, hydroxyl, alkoxy, amino, alkylamino, dialkylamino and halogen; alkylamino and alkoxyalkyl;

R8 is alkoxycarbonylamino, the acyl residue of an α or β-amino acid, or a residue of the formula Q-(X)$_r$—Y—,
wherein Q is a 3-6 membered ring which optionally contains nitrogen, sulphur and/or oxygen and which is optionally fused to a phenyl ring or to a 5-6 membered heterocyclic ring and which is optionally substituted with 1 to 4 substituents selected from alkyl, allyl, hydroxyl, alkoxy, amino, alkylamino, dialkylamino, carboxamide which may be substituted, carboxylic acid, carbonylalkoxy, aminocarbonyl, alkylaminocarbonyl, halogen, halogenomethyl, dihalogenomethyl, trihalogenomethyl, sulfamide, substituted sulfamide with substituents selected from alkyl, allyl, phenyl which may be substituted with 1 to 5 substituents selected from alkyl, hydroxyl, alkoxy, amino, alkylamino and halogen and benzyl which may be substituted with 1 to 5 substituents selected from alkyl, hydroxyl, alkoxy, amino, alkylamino, halogen and benzyl, urea which may be substituted with alkyl, aminoalkyl or alkoxy and carbamate which may be substituted with alkyl, aminoalkyl or alkoxy, X signifies a linear spacer of from 1 to 6 atoms length and containing carbon, nitrogen, oxygen and/or sulphur atoms, of which up to 2 atoms can be nitrogen atoms and 1 atom can be oxygen or sulphur, r is an integer of from 0 to 1; and Y is selected from —CO—, —CS—, —NHCO—, —NHCONH— and —SO$_2$—;

or a pharmaceutically acceptable salt thereof, or b2) a monobactam derivative of the general formula III:

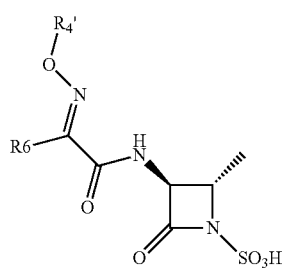

in which

R4' signifies hydrogen, alkyl or CH(Rx')Z', wherein

Rx' is selected from hydrogen; $(C_1\text{-}C_6)$alkyl; allyl; phenyl and $(C_3\text{-}C_6)$cycloalkyl; and Z' signifies COOH or a group of one of the following two formulae:

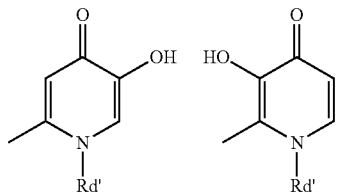

in which Rd' is hydrogen or hydroxy; and

R6 is as defined for formula I; or a pharmaceutically acceptable salt thereof, or b3) a penam sulfone derivative of the general formulae IV or V:

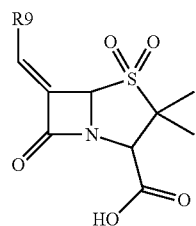

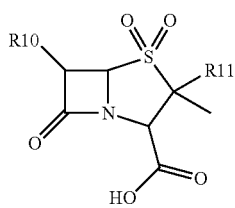

in which

R9 signifies COOH or a 5-6 membered monocyclic or polycyclic heteroaromatic group;

R10 signifies hydrogen or halogen;

R11 signifies $CH_2R12$; $CH=CHR12$ wherein R12 is hydrogen, halogen, cyano, carboxylic acid, acyl such as acetyl, carboxamide which may be substituted, alkoxycarbonyl or a 5-6 membered heteroaromatic ring which is optionally substituted with 1 to 5 substituents selected from alkyl, hydroxyl, alkoxy, amino, alkylamino, dialkylamino and halogen; or which is optionally fused with a 5-6 membered heteroaromatic ring; CH=NR12' wherein R12' is amino, alkylamino, dialkylamino, aminocarbonyl, acylamino such as acetylamino, hydroxy, alkoxy, or a pharmaceutically acceptable salt thereof;

or b4) an oxapenam derivative of the general formula VI:

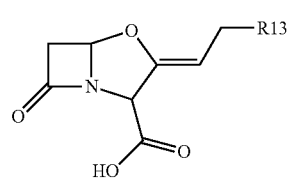

in which

R13 signifies OR14; $S(O)_nR14$ or a 5-6 membered heteroaromatic ring which may be substituted with 1 to 5 substituents selected from alkyl, hydroxyl, alkoxy, amino, alkylamino, dialkylamino and halogen; whereby n=0, 1 or 2, and R14 is hydrogen, alkyl, $(C_2\text{-}C_7)$alkene, $(C_2\text{-}C_7)$alkyne or a 5-6 membered heteroaromatic ring which may be substituted with 1 to 5 substituents selected from alkyl, hydroxyl, alkoxy, amino, alkylamino, dialkylamino and halogen, or a pharmaceutically acceptable salt thereof;

or b5) a penem derivative of the general formula VII:

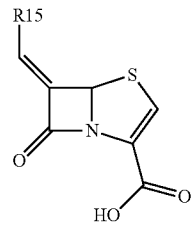

in which

R15 signifies a 5-6 membered heteroaromatic ring which may be substituted with 1 to 5 substituents selected from alkyl, hydroxyl, alkoxy, amino, alkylamino, dialkylamino and halogen; or which is optionally fused with a 5-6 membered heteroaromatic ring and/or which is optionally bound to the exo-methylene group over a —CH=CH— spacer being preferably in the (E)-configuration, or a pharmaceutically acceptable salt thereof;

or b6) a cephem sulfone derivative of the general formula VIII:

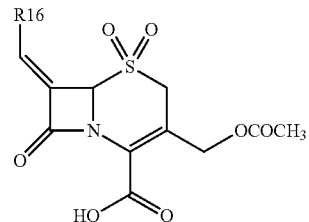

in which

R16 signifies COOR17, whereby R17 signifies hydrogen or alkyl; or a 5-6 membered heteroaromatic ring which is optionally fused with a 5-6 membered heteroaromatic ring being optionally substituted with 1 to 5 substituents selected from alkyl, hydroxyl, alkoxy, amino, alkylamino, dialkylamino, halogen; and/or being optionally bound to the exo-methylene group over a —CH=CH— spacer being preferably in the (E)-configuration, or a pharmaceutically acceptable salt thereof;

or b7) a carbapenem derivative of the general formula IX:

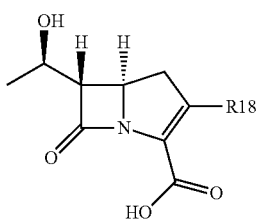

IX in which R18 signifies —S-alkyl, —S—(CH$_2$)$_2$—NH—CH=NH or a group of the following two formulae

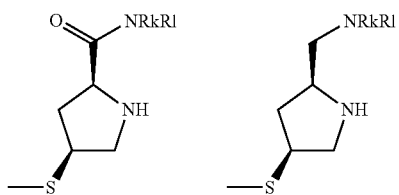

wherein Rk and Rl are individually selected from hydrogen, alkyl, 2-, 3-, 4-carboxyphenyl and sulfamoyl, or a pharmaceutically acceptable salt thereof;

or b8) a boronate derivative of the general formula X:

X wherein R19 signifies a 5-6 membered heteroaromatic ring which may be substituted with amino, alkylamino, dialkylamino or alkylsulfoxide, or a pharmaceutically acceptable salt thereof;

or b9) a boronate derivative of the general formula XI:

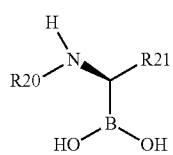

XI wherein

R20 and 21 are independently selected from a 5-6 membered heteroaromatic ring or phenyl which may be substituted with 1 to 5 substituents selected from alkyl, hydroxyl, alkoxy, amino, alkylamino, dialkylamino and halogen and benzyl which may be substituted with 1 to 5 substituents selected from alkyl, hydroxyl, alkoxy, amino, alkylamino, dialkylamino and halogen, or a pharmaceutically acceptable salt thereof;

or b10) a phosphonate derivative of the general formula XII:

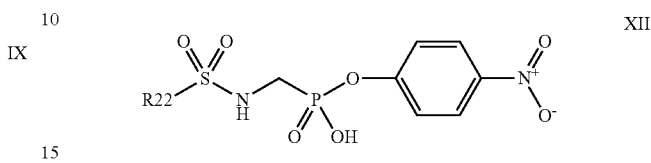

XII wherein

R22 is selected from a 5-6 membered heteroaromatic ring which may be substituted with 1 to 5 substituents selected from alkyl, hydroxyl, alkoxy, amino, alkylamino, dialkylamino and halogen and which is optionally fused with a 5-6 membered heteroaromatic ring; phenyl which may be substituted with 1 to 5 substituents selected from alkyl, hydroxyl, alkoxy, amino, alkylamino, dialkylamino and halogen; and benzyl which may be substituted with 1 to 5 substituents selected from alkyl, hydroxyl, alkoxy, amino, alkylamino, dialkylamino and halogen, or a pharmaceutically acceptable salt thereof;

or b11) a diazabicyclooctane derivative of the general formula XIII:

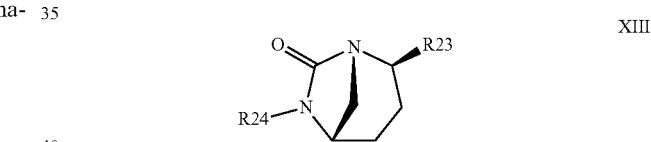

XIII in which

R23 signifies hydrogen, carboxylic acid, alkoxycarbonyl or carboxamide which may be substituted, and R24 signifies SO$_3$H, OSO$_3$H or OCRjRj'COOH, wherein Rj and Rj' are as defined for formula II, or a pharmaceutically acceptable salt thereof.

As a preferred embodiment of the invention, the pharmaceutical compositions may comprise two or more compounds selected from one of the formulae II to XIII of b1) to b11), these two or more compounds being different from each other.

The object set is also solved by the novel monobactam antibiotics of formula Ia as described hereinafter, which may be used in the same combinations as outlined above.

Further objects of the invention are visible from the description hereinafter and from the appended claims.

DETAILED DESCRIPTION OF THE INVENTION

It has surprisingly been found that the efficacy of monobactam antibiotics of the formula I against aerobic Gram-negative bacteria can be potentiated by co-using a β-lactamase inhibitor according to any one of the formulae II to XIII.

In formula I, when the oxoazetidine ring is lying in the plane of the paper, preferably R3 points downwards from the plane, and R2 points upwards from the plane.

For the purposes of the present invention, the compounds of the above formula III are not considered as "antibiotically active" compounds in the sense of claim 1. The compounds in formula I have the oximino group predominantly the "syn" configuration shown in formula I, whereas the compounds III have the oximino group specifically in the "anti" configuration shown in formula III.

The term "alkyl", as used in the present application, preferably means straight-chain or branched ($C_1$-$C_7$)alkyl such as in particular methyl, ethyl, propyl, butyl, pentyl, hexyl, heptyl, octyl, isopropyl, isobutyl, tert-butyl or neopentyl.

The term "alkoxy", as used in the present application, preferably means straight-chain or branched ($C_1$-$C_7$)alkoxy, such as in particular methoxy, ethoxy, propoxy, 1- or 2-butoxy, 1-, 2-, or 3-pentyloxy, 1-, 2- or 3-hexyloxy, 1-, 2-, 3-, or 4-heptyloxy or tert-butoxy. The term "alkylhydroxyl" as also used, shall be considered synonymous to "alkoxy"; in particular for the alkyl in "alkylhydroxyl" the same definition shall apply as given above for "alkyl".

The term "carboxamide which may be substituted" preferably has the meaning that the carboxamide has 0 to 2 hydrogen atoms attached to the amino moiety, with the remainder of the substituents on the amino moiety being alkyl or phenyl which may be substituted.

The term "imine which may be substituted" preferably means that the imine bears at the imine nitrogen hydrogen, alkyl, phenyl which may be substituted or benzyl which may be substituted.

The terms "optionally substituted phenyl" and "optionally substituted benzyl", if given without specifically indicated substituents, shall preferably mean that the phenyl or benzyl is optionally substituted with 1 to 5 substituents selected from alkyl, alkoxy, dialkylamino and halogen, wherein the "alkyl" itself and the alkyl in dialkylamino and alkoxy has the meaning as defined above.

The term "linear spacer", as used in the present application, preferably means a linear divalent group selected from —O—, —S—, —NH—, —NH—NH—, —CH$_2$—, —CO—, —CH$_2$O—, —CH$_2$CH$_2$—, —CH═CH—, —CH$_2$NH—, —S—CH$_2$—, —SO$_2$—, —CH$_2$—, —O—CH$_2$—, —S—CH$_2$CH$_2$—, —CH$_2$CH$_2$—NH—, —CH$_2$—NH—CO—CH$_2$CH$_2$—, —CH$_2$—NH—CO—O—CH$_2$CH$_2$, —CH$_2$—NH—CO—NH—CH$_2$CH$_2$, —CH$_2$—O—CO—NH—CH$_2$CH$_2$—, —CH(OH)—, —CH(COOH)—, —CH(OSO$_3$H)—, —CH(OCONH$_2$)— and —CH[CH(CH$_3$)$_2$]—.

Some compounds of formula I may, when they contain an acidic group (such as when R1 is SO$_3$H, OSO$_3$H, CRaRa'COOH, OCRaRa'COOH or SO$_2$NHRb) be present as a salt with a pharmaceutically acceptable inorganic base (e.g. NaOH, KOH, NH$_3$, K$_2$CO$_3$, Na$_2$CO$_3$, Na$_2$HPO$_4$ or K$_2$HPO$_4$) or organic base (e.g. NEt$_3$, HNiPr$_2$, triethanolamine, TRIS or basic amino acids such as arginine and lysine). The use of such salts of compounds of formula I is encompassed by the invention. Also, some of the compounds of formula I, when they contain both an acidic group (such as when R1 is SO$_3$H, OSO$_3$H, CRaRa'COOH, OCRaRa'COOH or SO$_2$NHRb) and a basic group (such as when R6 is 2-amino-1,3-thiazol-4-yl, 5-amino-1,2,4-thiadiazol-3-yl, 5-amino-1,2,4-oxadiazol-3-yl, 3-aminoisoxazol-5-yl, 5-amino-1-methylpyrazol-3-yl, 5-aminopyrazol-3-yl, 6-amino-2-pyridyl, 4-aminopyrimidin-2-yl, 2-carbonylamino-1,3-thiazol-4-yl or 2-amino-5-chloro-1,3-thiazol-4-yl) may form an inner, zwitterionic salt; such inner salts are also intended to be encompassed by the claims.

When R4 contains a 4-pyridone moiety, wherein Rd is selected from hydrogen and hydroxy, there is the possibility of tautomerism:

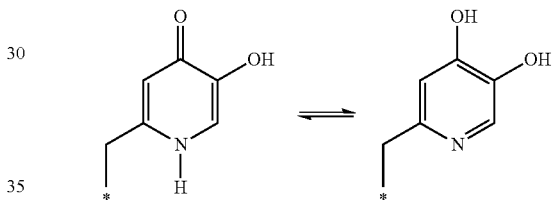

The invention intends to encompass the use of any such tautomers.

A first group of preferred examples of compounds of the formula I for the combinations of the invention are aztreonam, carumonam, tigemonam, and compounds according to the following table 1 (R5 is in these compounds always H):

TABLE 1

| Compound number | R1 | R2 | R3 | R4 | R6 |
|---|---|---|---|---|---|
| 1 | SO$_3$H | H | CH$_3$ | ![pyridone with ethyl, N-OH, OH] | ![2-amino-4-methylthiazol-5-yl] |
| 2 | SO$_3$H | H | CH$_3$ | ![pyridone with ethyl, N-OH, OH] | ![5-amino-3-methyl-1,2,4-thiadiazol] |

TABLE 1-continued
| Compound number | R1 | R2 | R3 | R4 | R6 |
|---|---|---|---|---|---|
| 3 | SO$_3$H | H | CH$_3$ | 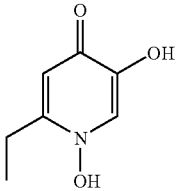 | 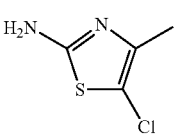 |
| 4 | SO$_3$H | H | CH$_3$ | CH$_3$ | 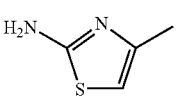 |
| 5 | SO$_3$H | H | CH$_3$ | 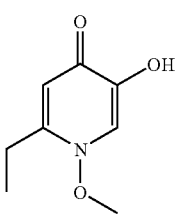 | 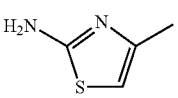 |
| 6 | SO$_3$H | H | CH$_3$ | 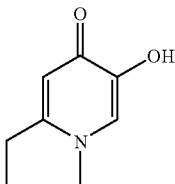 | 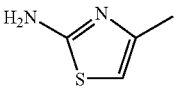 |
| 7 | SO$_3$H | H | CH$_3$ | 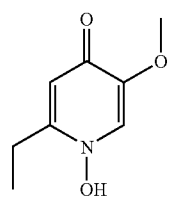 | 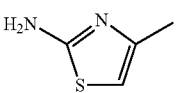 |
| 8 | SO$_3$H | H | CH$_3$ | 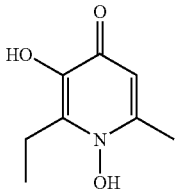 | 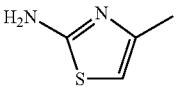 |
| 9 | SO$_3$H | H | H | 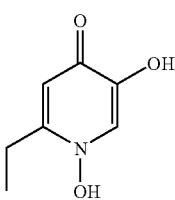 | 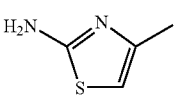 |
| 10 | SO$_3$H | H | CH$_3$ | CH$_2$CH$_2$N(OH)COCH$_3$ | 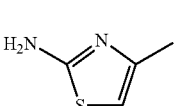 |

TABLE 1-continued

| Compound number | R1 | R2 | R3 | R4 | R6 |
|---|---|---|---|---|---|
| 11 | SO₃H | H | CH₃ | 2-ethyl-1-amino-5-hydroxy-pyridin-4(1H)-one | 2-amino-4-methylthiazol-5-yl |
| 12 | OSO₃H | H | CH₃ | 2-ethyl-1-hydroxy-5-hydroxy-pyridin-4(1H)-one | 2-amino-4-methylthiazol-5-yl |
| 13 | 5-methyl-1H-tetrazol-1-yl | H | CH₃ | 2-ethyl-1-hydroxy-5-hydroxy-pyridin-4(1H)-one | 2-amino-4-methylthiazol-5-yl |
| 14 | SO₂NH₂ | H | CH₃ | 2-ethyl-1-hydroxy-5-hydroxy-pyridin-4(1H)-one | 2-amino-4-methylthiazol-5-yl |
| 15 | SO₃H | H | CH₃ | 2-ethyl-1-hydroxy-5-hydroxy-pyridin-4(1H)-one | 3-amino-5-methyl-1H-1,2,4-triazol-5-yl |
| 16 | SO₃H | H | CH₃ | 2-ethyl-1-hydroxy-5-hydroxy-pyridin-4(1H)-one | 5-amino-3-methyl-1,2,4-oxadiazol-2-yl |
| 17 | SO₃H | H | CH₃ | 2-ethyl-1-hydroxy-5-hydroxy-pyridin-4(1H)-one | 3-amino-5-methylisoxazol-4-yl |

TABLE 1-continued
| Compound number | R1 | R2 | R3 | R4 | R6 |
|---|---|---|---|---|---|
| 18 | SO₃H | H | CH₃ | 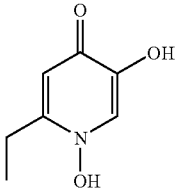 | 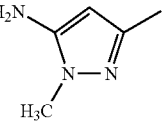 |
| 19 | SO₃H | H | CH₃ | 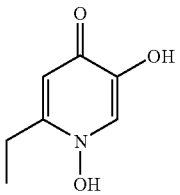 | 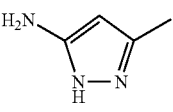 |
| 20 | SO₃H | H | CH₃ | 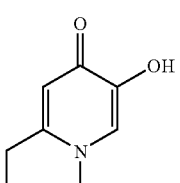 | 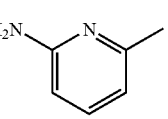 |
| 21 | SO₃H | H | CH₃ | 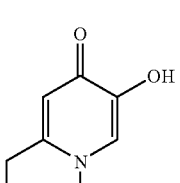 | 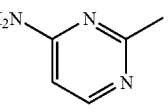 |
| 22 | OCH₂COOH | H | CH₃ | 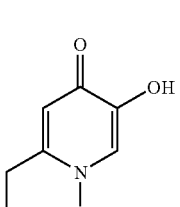 | 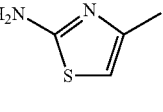 |
| 23 | OCH(CH₃)COOH | H | CH₃ | 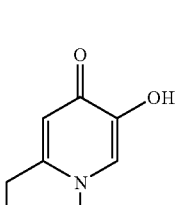 | 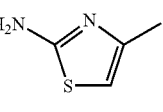 |
| 24 | OSO₃H | CH₂F | H | 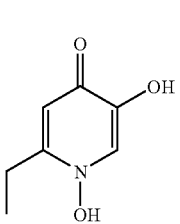 | 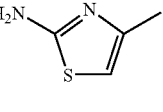 |

TABLE 1-continued
| Compound number | R1 | R2 | R3 | R4 | R6 |
|---|---|---|---|---|---|
| 25 | OSO₃H | CH₂OCONH₂ | H | 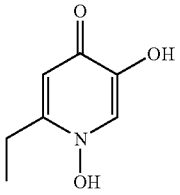 | 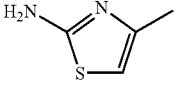 |
| 26 | OSO₃H | CH₃ | CH₃ | 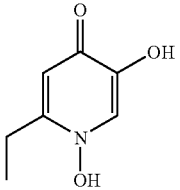 | 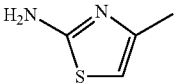 |
| 27 | SO₃H | H | CH₃ | 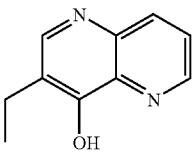 | 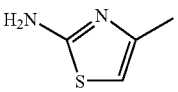 |
| 28 | SO₃H | H | CH₃ | 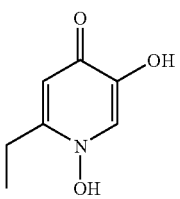 | 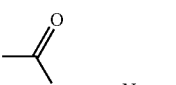 |
| 29 | OSO₃H | H | CH₃ | 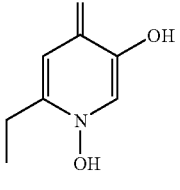 | 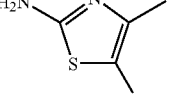 |
| 30 | OSO₃H | H | CH₃ | 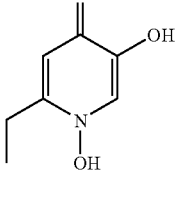 | 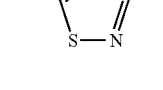 |
| 31 | OSO₃H | CH₃ | CH₃ | 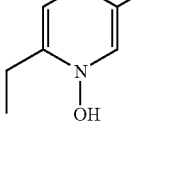 | 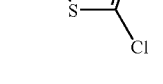 |

TABLE 1-continued
| Compound number | R1 | R2 | R3 | R4 | R6 |
|---|---|---|---|---|---|
| 32 | OSO₃H | CH₃ | CH₃ | 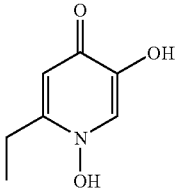 | 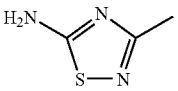 |
| 33 | OCH₂COOH | CH₃ | CH₃ | 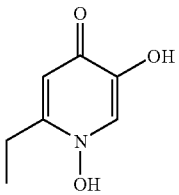 | 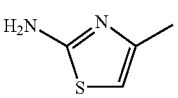 |
| 34 | OCH₂COOH | CH₃ | CH₃ | 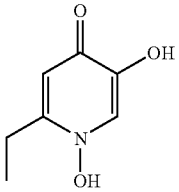 | 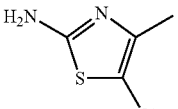 |
| 35 | OCH₂COOH | CH₃ | CH₃ | 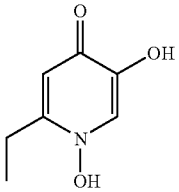 | 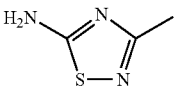 |
| 36 | OCH₂COOH | H | CH₃ | 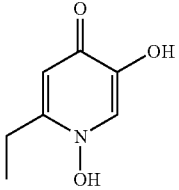 | 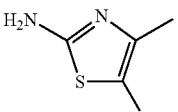 |
| 37 | OCH₂COOH | H | CH₃ | 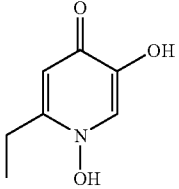 | 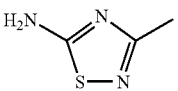 |
| 38 | SO₃H | CH₃ | CH₃ | 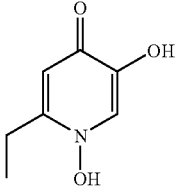 | 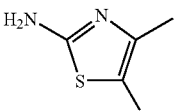 |

TABLE 1-continued
| Compound number | R1 | R2 | R3 | R4 | R6 |
|---|---|---|---|---|---|
| 39 | SO₃H | CH₃ | CH₃ | 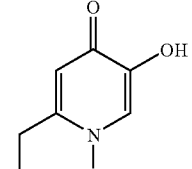 | 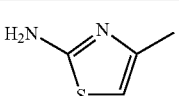 |
| 40 | SO₃H | CH₃ | CH₃ | 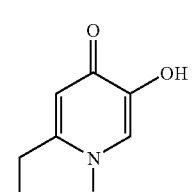 | 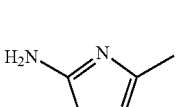 |
| 41 | OCH₂COOH | CH₂OCONH₂ | H | 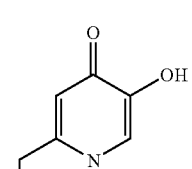 | 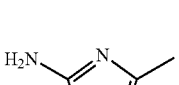 |
| 42 | OCH₂COOH | CH₂OCONH₂ | H | 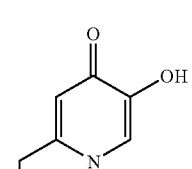 | 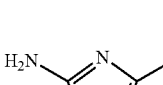 |
| 43 | OCH₂COOH | CH₂OCONH₂ | H | 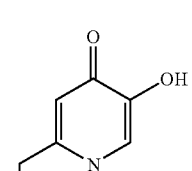 | 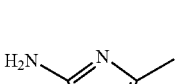 |
| 44 | OCH₂COOH | CH₂F | H | 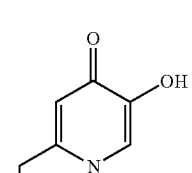 | 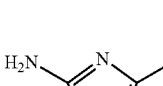 |
| 45 | OCH₂COOH | CH₂F | H | 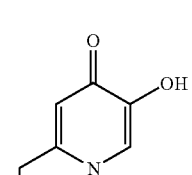 | 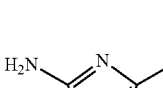 |

TABLE 1-continued

| Compound number | R1 | R2 | R3 | R4 | R6 |
|---|---|---|---|---|---|
| 46 | OCH$_2$COOH | CH$_2$F | H | ![structure] | ![structure] |
| 47 | OSO$_3$H | CH$_2$OCONH$_2$ | H | ![structure] | ![structure] |
| 48 | OSO$_3$H | CH$_2$OCONH$_2$ | H | ![structure] | ![structure] |

The numbering of the compounds as given in above table 1 is used in the following for the sake of conciseness.

The compounds of the above table 1 are, when their compound numbers are underscored and bold, part of the present invention.

Among the compounds of formula I which are more preferred in the combinations of the invention and which are novel per se are those of the following formula Ia:

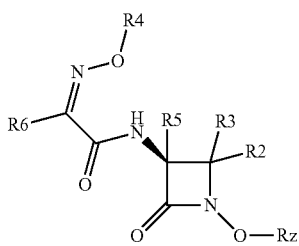

Ia wherein
Rz is SO$_3$H or CRaRa'COOH, wherein Ra and Ra' are as defined for formula I;
R2, R3, R5 and R6 are as defined for formula I;
R4 is CH$_2$Z; whereby Z is a group of one of the formulae

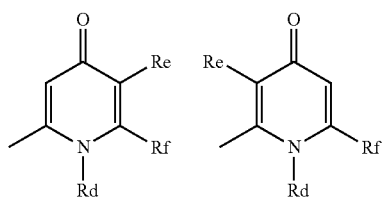

wherein Rd, Re and Rf are as defined for the compounds of formula I; and the pharmaceutically acceptable salts or inner salts thereof. This first group of compounds forms part of the invention. When Rz is SO$_3$H, then preferably both R2 and R3 are methyl. When Rz is CRaRa'COOH, then R2 is preferably selected from hydrogen, methyl, fluoromethyl and carbamoyloxymethyl; and R3 is preferably selected from or hydrogen and methyl; and more preferably here, the absolute configuration at the carbon atom bearing R2 and R3 is (S). Preferably, Ra and Ra' are each hydrogen. Preferably for all compounds of formula Ia, the Rd, Re and Rf are individually selected from hydrogen and hydroxy, with the proviso that at least two of Rd, Re and Rf are hydroxy (most preferably Rd and Re are hydroxy and Rf is hydrogen). R5 is preferably hydrogen. R6 is preferably an optionally amino-substituted and optionally chloro-substituted 5-6-membered heteroaromatic ring, this ring being more preferably selected from 2-amino-1,3-thiazol-4-yl, 5-amino-1,2,4-thiadiazol-3-yl, 5-amino-1,2,4-oxadiazol-3-yl, 3-aminoisoxazol-5-yl, 5-amino-1-methylpyrazol-3-yl, 5-aminopyrazol-3-yl, 6-amino-2-pyridyl, 4-aminopyrimidin-2-yl, 2-carbonylamino-1,3-thiazol-4-yl, 2-amino-5-chloro-1,3-thiazol-4-yl and 2-thienyl.

More preferred examples of the compound of formula Ia are the compounds (12), (22), (23), (24), (25), (26), (29), (30), (31), (32), (33), (34), (35), (36), (37), (41), (42), (43), (44), (45), (46), (47) and (48) of above table 1. The most preferred compounds of formula Ia are compounds (22), (23), (26) and (31).

The compounds of formula Ia, if Rz is SO$_3$H, can be made by a methodology as outlined in scheme 4 below, until the R2,R3-disubstituted 3-amino-2-oxoazetidine hydroxysulfonate, and reacting this further in a manner known per se to connect the 3-amino substituents. The compounds of formula Ia, if Rz is CRaRa'COOH, can be prepared following the synthesis scheme of compounds II to X as described in U.S. Pat. No. 4,939,253 (column 15, line 26 to column 17, line 25), and reacting the obtained oxoazetidine X further according to scheme 1 described hereinafter.

A second group of compounds of formula I which is preferred in the combinations of the invention and is novel are those of the following formula Ib:

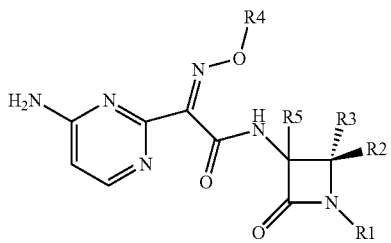

and the pharmaceutically acceptable salts thereof, wherein the residues R1, R2, R3, R4 and R5 are as defined for formula I. This second group of compounds also forms part of the invention. Preferably, in these compounds R1 is SO$_3$H, R2 is H, R3 is methyl and R4 is C(Rx)(Ry)Z; whereby Rx=Ry=H, and Z is a group of one of the formulae

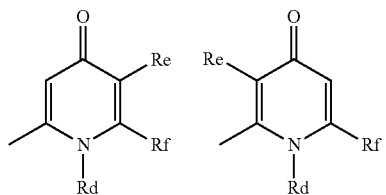

wherein Rd, Re and Rf are individually selected from hydrogen and hydroxy, with the proviso that at least two of Rd, Re and Rf are hydroxy (most preferably Rd and Re are hydroxy and Rf is hydrogen).

The antibiotically active monobactams of formula I may firstly be combined with b1) β-lactamase inhibitors of the above general formula II.

In formula II, R8 is preferably of the formula Q-(X)$_r$—CO—. The following subgroups are more preferable within this formula:

a) With X=—CH$_2$— and r=1; wherein Q is a pyridinium group which may be substituted with one to three substituents, preferably one to two substituents, selected from alkyl; perfluoroalkyl, in particular trifluoromethyl; phenyl; benzyl; R$_u$R$_v$N—, wherein R$_u$ and R$^v$ are independently selected from hydrogen, alkyl, cycloalkyl, pyrrolidinyl, carbamoyl and N-(carbamoylalkyl)carbamoyl, or wherein R$_u$ and R$_v$ taken together form an alkylene bridge —(CH$_2$)—$_w$, with w being an integer number of 3 to 6; alkylcarbonyl; R$_u$R$_v$NCO—, wherein R$_u$, and R$_v$ are as defined before; (alkoxycarbonyl)alkyl; thiocarbamoyl and alkoxycarbonyl; or wherein Q is a pyridinium group which is fused with a 5-6 membered carbocycle; and thioamide. Examples within this subgroup are pyridinium, 2-, 3- or 4-aminopyridinium, 3-N-methylaminopyridinium, 3-N,N-dimethylaminopyridinium, 4-(N-methylamino)pyridinium, 4-(N,N-dimethylamino)pyridinium, 3-carbamoylpyridinium, 3-(N-methylcarbamoyl)pyridinium, 3-(N,N-dimethylcarbamoyl)pyridinium, 4-carbamoylpyridinium, 4-(N-methylcarbamoyl)pyridinium, 4-(N,N-dimethylcarbamoyl)pyridinium, 3-(N-cyclopropylcarbamoyl)pyridinium, 4-(N-cylopropylcarbamoyl)pyridinium, 4-(N-methylcarbamoyl)pyridinium, 3-(methoxycarbonyl)pyridinium, 3-(ethoxycarbonyl)pyridinium, 4-(methoxycarbonyl)pyridinium, 4-(ethoxycarbonyl)pyridinium, 3-thiocarbamoylpyridinium, 3-(N-methylthiocarbamoyl)pyridinium, 3-(N,N-dimethylthiocarbamoyl)pyridinium, 4-thiocarbamoylpyridinium, 4-(N-methylthiocarbamoyl)pyridinium, 4-(N,N-dimethylthiocarbamoyl)pyridinium, 2,3-, 2,4-, 2,5-, 2,6-, 3,4-, 3,5-, 3,6-dimethylpyridinium, 3- or 4-isopropylpyridinium, 3- or 4-(trifloromethyl)pyridinium, 3- or 4-phenylpyridinium, 3- or 4-benzylpyridinium, quinolinium, isoquinolinium, 5,6,7,8-tetrahydroquinolinium and 5,6,7,8-tetrahydroisoquinolinium. In this subgroup, R7 is preferably —SO$_3^-$ or —OSO$_3^-$, to form a pharmaceutically acceptable inner salt. The compounds II of this subgroup a) themselves are per se also part of the invention, but compound 102 of table 2 below is known from J. Med. Chem. 1998, 41(21), 3961, and does per se not form part of the invention.

b) With X=—SCH$_2$— and r=1; wherein Q is 1,2,3,4-tetrazol-5-yl, which may be substituted at its 1-position with a substituent selected from alkyl, aminoalkyl or alkoxyalkyl. Examples for this substituent are methyl, ethyl, propyl, butyl, 2-aminoethyl, 2-(N-methylamino)ethyl, 2-(N,N-dimethylamino)ethyl, 3-aminopropyl, 3-(N-methylamino)propyl, 3-(N,N-dimethylamino)propyl, 2-(N-ethylamino)ethyl, 2-(N,N-diethylamino)ethyl, 3-(N-ethylamino)propyl and 3-(N,N-diethylamino)propyl. In these compounds, R7 is preferably —SO$_3$H or OSO$_3$H, whereby the possibility of formation of an inner, acid addition salt may be allowed, to form a pharmaceutically acceptable inner salt.

c) With X=—CH$_2$NH$_2$— and r=1; wherein Q is phenyl which may be substituted with one to two substituents selected from hydroxy and alkoxy, or a 5-6-membered heterocycle which preferably is selected from oxazol-2-yl, -3-yl or -4-yl, furan-2-yl or 3-yl, thiophen-2-yl or -3-yl, 1,3-thiazol-2-yl, -3-yl, -4-yl or -5-yl and which optionally may be substituted with one to two substituents selected from alkyl and alkoxy.

d) With X=—NH$_2$— and r=1, wherein Q is phenyl which may be substituted with one to two substituents selected from hydroxy; alkoxy and a substituted urea of the formula H$_2$N[(CH$_2$)$_m$O]$_n$(CH$_2$)$_o$HNCONH— or a substituted carbamate of the formula H$_2$N[(CH$_2$)$_m$O]$_n$(CH$_2$)$_o$HNCOO—, wherein m and o are independently integer numbers from 2 to 3 and n is an integer number from 0 to 1. Examples for Q here are phenyl, 2-, 3- and 4-hydroxyphenyl, 2,3-, 2,4-, 2,6-, 3,4-, 3,5- and 3,6-dihydroxyphenyl, 2-, 3- and 4-methoxyphenyl, 3-[N'-{2-(2-aminoethoxy)et-hyl}carbamoylamino]phenyl, 3-[N'-{2-(3-aminopropoxy)et-hyl}carbamoylamino]phenyl, 3-[N'-{3-(2-aminoethoxy)propyl}carbamoylamino]phenyl, 3-[N'-{3-(3-aminopropoxy)propyl}carbamoylamino]phenyl, 4-[N'-{2-(2-aminoethoxy)ethyl}carbamoylamino]phenyl, 4-[N'-{2-(3-aminopropoxy)ethyl}carbamoylamino]phenyl, 4-[N'-{3-(2-aminoethoxy)propyl}carbamoylamino]phenyl, 4-[N'-{3-(3-aminopropoxy)propyl}carbamoylamino]phenyl, 3-[N'-{2-(2-aminoethoxy)ethyl}carbamoyloxy]phenyl, 3-[N'-{2-(3-aminopropoxy)ethyl}carbamoyloxy]phenyl, 3-[N'-{3-(2-aminoethoxy)propyl}carbamoyloxy]phenyl, 3-[N'-{3-(3-aminopropoxy)propyl}carbamoyloxy]phenyl, 4-[N'-{2-(2-aminoethoxy)ethyl}carbamoyloxy]phenyl, 4-[N'-{2-(3-aminopropoxy)ethyl}carbamoyloxy]phenyl, 4-[N'-{3-(2-aminoethoxy)propyl}carbamoyloxy]phenyl and 4-[N'-{3-(3-aminopropoxy)propyl}carbamoyloxy]phenyl.

Particularly preferred examples of the compounds of formula II are according to the following table 2

TABLE 2
| Compound number | R7 | R8 |
|---|---|---|
| 101 | SO$_3^-$ | 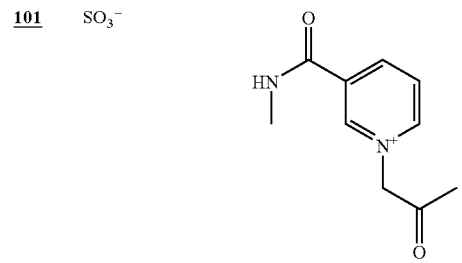 |
| 102 | SO$_3^-$ | 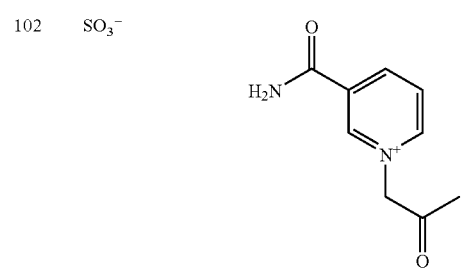 |
| 103 | SO$_3^-$ | 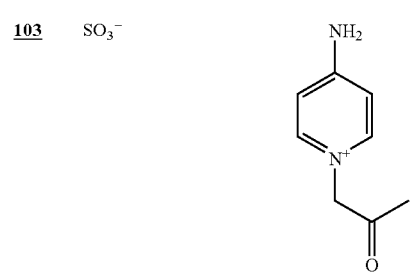 |
| 104 | SO$_3^-$ | 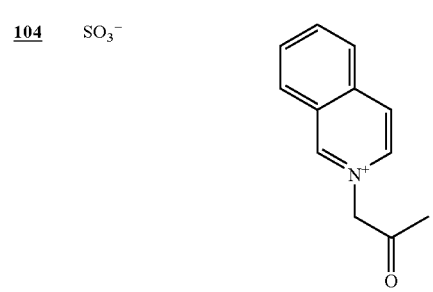 |
| 105 | SO$_3^-$ | 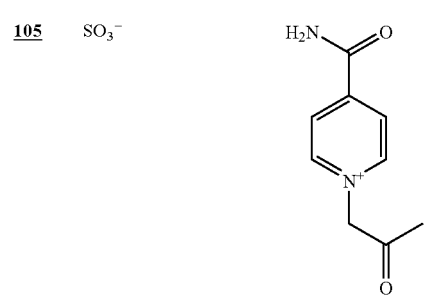 |
TABLE 2-continued
| Compound number | R7 | R8 |
|---|---|---|
| 106 | SO$_3^-$ | 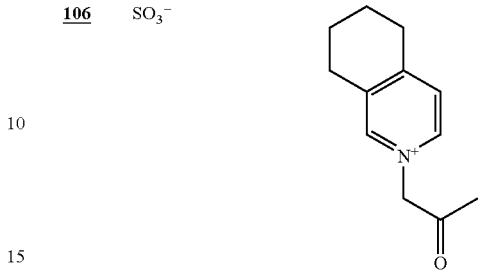 |
| 107 | SO$_3^-$ | 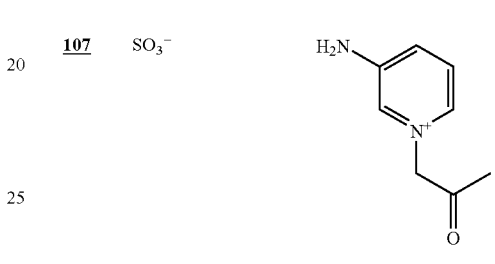 |
| 108 | SO$_3^-$ | 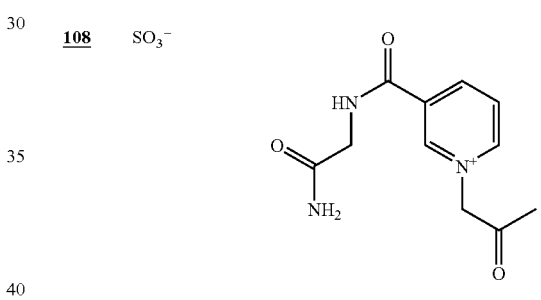 |
| 109 | SO$_3^-$ | 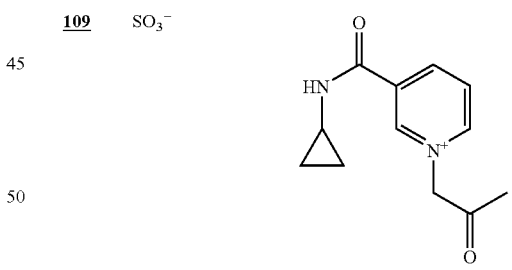 |
| 110 | SO$_3^-$ | 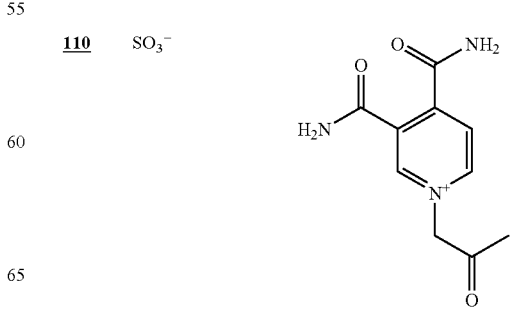 |

TABLE 2-continued
| Compound number | R7 | R8 |
|---|---|---|
| 111 | SO$_3^-$ | 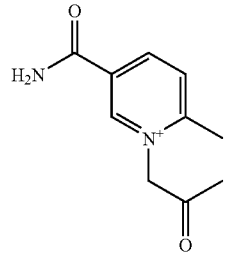 |
| 112 | SO$_3^-$ | 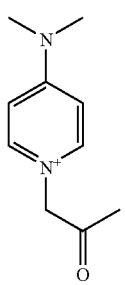 |
| 113 | SO$_3^-$ | 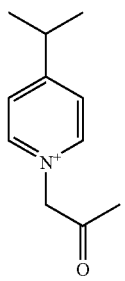 |
| 114 | SO$_3^-$ | 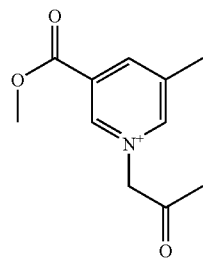 |
| 115 | SO$_3^-$ | 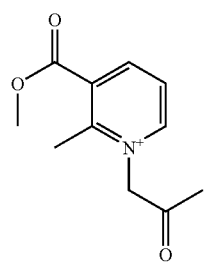 |
| 116 | SO$_3^-$ | 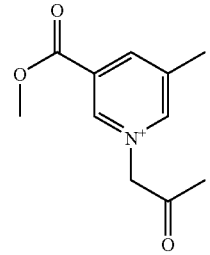 |
| 117 | SO$_3^-$ | 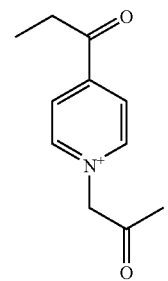 |
| 118 | SO$_3^-$ | 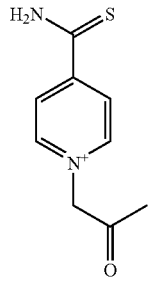 |
| 119 | SO$_3^-$ | 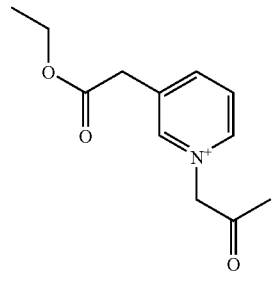 |
| 120 | SO$_3^-$ | 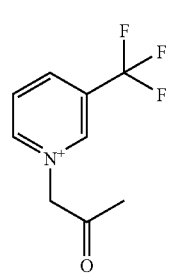 |

TABLE 2-continued

| Compound number | R7 | R8 |
|---|---|---|
| 121 | SO₃⁻ | 3,4-dimethylpyridinium-N-propan-2-one |
| 122 | SO₃⁻ | N-[(3S)-pyrrolidin-3-yl]-1-(2-oxopropyl)pyridinium-3-carboxamide |
| 123 | SO₃⁻ | 3-benzyl-1-(2-oxopropyl)pyridinium |
| 124 | SO₃⁻ | 3-phenyl-1-(2-oxopropyl)pyridinium |
| 125 | SO₃⁻ | N-[(3R)-pyrrolidin-3-yl]-1-(2-oxopropyl)pyridinium-3-carboxamide |
| 126 | SO₃⁻ | 4-amino-1-(2-oxopropyl)pyridinium-3-carboxamide |
| 127 | SO₃⁻ | 5-methyl-1-(2-oxopropyl)pyridinium-3-carboxamide |
| 128 | SO₃⁻ | 3-ureido-1-(2-oxopropyl)pyridinium |
| 129 | SO₃⁻ | 5-amino-1-(2-oxopropyl)pyridinium-3-carboxamide |
| 201 | SO₃Na | 1-phenyl-5-[(2-oxopropyl)thio]-1H-tetrazole |
| 202 | SO₃Na | 5-methyl-2-[(2-oxopropyl)thio]-1,3,4-thiadiazole |

TABLE 2-continued
| Compound number | R7 | R8 |
|---|---|---|
| 203 | SO₃H | 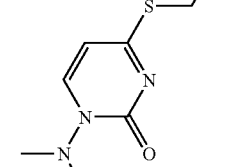 |
| 204 | SO₃⁻ | 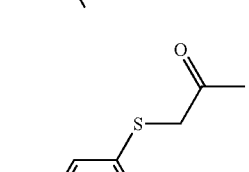 |
| 205 | SO₃H | 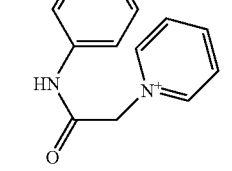 |
| 206 | SO₃Na | 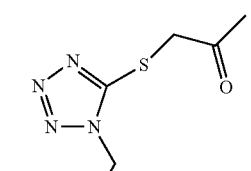 |
| 207 | SO₃H | 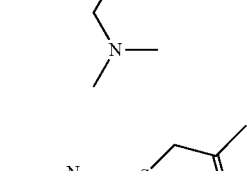 |
| 208 | SO₃H | 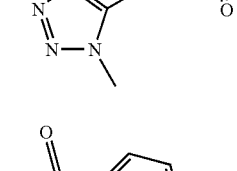 |
| 209 | SO₃H | |
| 210 | SO₃H | |
| 211 | SO₃H | |
| 212 | SO₃H | |
| 213 | SO₃H | |
| 214 | SO₃H | |
| 215 | SO₃H | |

TABLE 2-continued

| Compound number | R7 | R8 |
|---|---|---|
| 301 | SO₃Na | N-phenylacetamide |
| 302 | SO₃Na | N-benzylacetamide |
| 303 | SO₃Na | N-(3,4-dihydroxybenzyl)acetamide |
| 304 | SO₃Na | N-(4-methoxyphenyl)acetamide |
| 305 | SO₃Na | 3-acetamidobenzamide |
| 306 | SO₃Na | N-(3,4-dihydroxyphenyl)acetamide |
| 307 | SO₃Na | N,N'-(1,3-phenylene)diacetamide |
| 308 | SO₃Na | 3-acetamidobenzenesulfonamide |
| 309 | SO₃Na | N-(4-(dimethylamino)phenyl)acetamide |
| 310 | SO₃Na | 4-acetamido-N-(2-(dimethylamino)ethyl)benzamide |
| 311 | SO₃Na | 4-acetamidobenzamide |
| 312 | SO₃Na | 4-acetamido-N-(2-amino-2-oxoethyl)benzamide |
| 313 | SO₃Na | N-((3-methoxyisoxazol-5-yl)methyl)acetamide |
| 314 | SO₃Na | N-(thiophen-2-ylmethyl)acetamide |
| 315 | SO₃Na | 1-(4-acetamidophenyl)urea |
| 316 | SO₃Na | N-(4-hydroxyphenyl)acetamide |
| 317 | SO₃Na | N-(3-hydroxyphenyl)acetamide |
| 318 | SO₃H | N-(3-(oxazol-5-yl)phenyl)acetamide |

TABLE 2-continued

| Compound number | R7 | R8 |
|---|---|---|
| 319 | SO₃Na | 5-acetamido-1,3-dihydro-2H-benzimidazol-2-one |
| 320 | SO₃Na | ethyl 3-acetamidobenzoate |
| 321 | SO₃Na | N-(3-(hydroxymethyl)phenyl)acetamide |
| 322 | SO₃H | N-(piperidin-4-yl)acetamide |
| 323 | SO₃H | N-(4-(3-(2-(2-aminoethoxy)ethyl)ureido)phenyl)acetamide |
| 324 | SO₃H | N-(4-(3-(2-aminoethyl)ureido)phenyl)acetamide |
| 325 | SO₃H | N-(4-(3-(piperidin-4-yl)ureido)phenyl)acetamide |
| 326 | SO₃H | N-(4-(piperazine-1-carboxamido)phenyl)acetamide |
| 327 | SO₃Na | N-(4-aminophenyl)acetamide |
| 328 | SO₃Na | 2-acetamidobenzamide |
| 329 | SO₃Na | benzyl (2-((4-acetamidophenyl)amino)-2-oxoethyl)carbamate |
| 330 | SO₃H | N-(4-(3-(2-morpholinoethyl)ureido)phenyl)acetamide |
| 331 | SO₃H | complex bis-urea morpholine derivative |
| 332 | SO₃H | N-(4-((2-aminoethyl)carbamoyl)phenyl)acetamide |
| 333 | SO₃Na | tert-butyl (4-acetamidophenyl)carbamate |
| 334 | SO₃H | N-(4-(morpholinomethyl)phenyl)acetamide |

TABLE 2-continued
| Compound number | R7 | R8 |
|---|---|---|
| 335 | SO$_3$H | 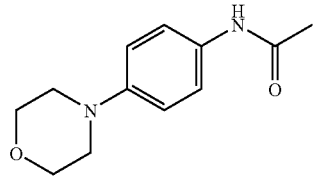 |
| 336 | SO$_3$H | 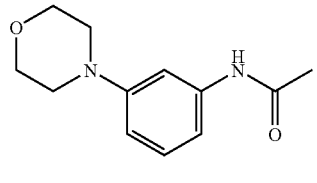 |
| 337 | SO$_3$H | 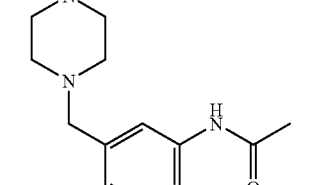 |
| 338 | SO$_3$H | 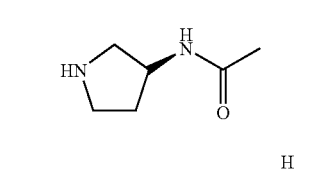 |
| 339 | SO$_3$H | 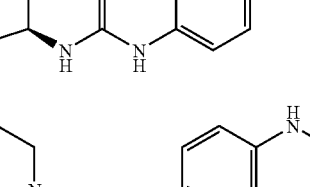 |
| 340 | SO$_3$H | 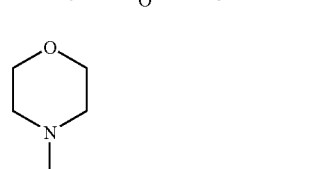 |
| 341 | SO$_3$H | 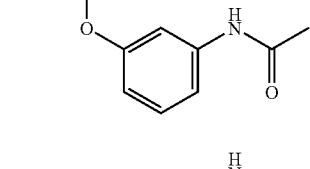 |
| 342 | SO$_3$H | 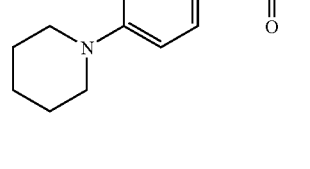 |
| 343 | SO$_3$H | 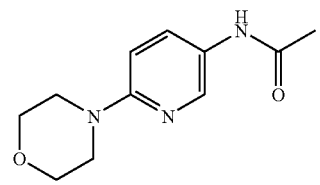 |
| 344 | SO$_3$H | 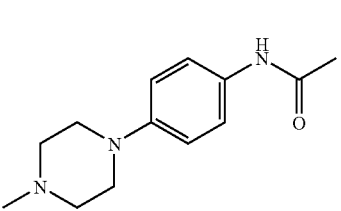 |
| 401 | SO$_3$H | 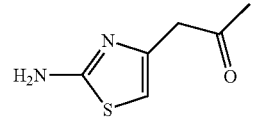 |
| 402 | SO$_3$H | 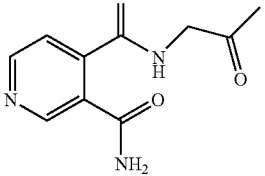 |
| 403 | SO$_3$H | 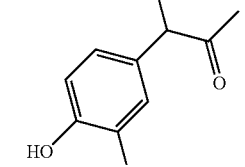 |
| 404 | SO$_3$Na | 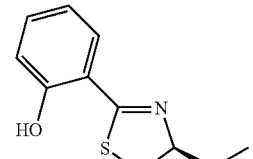 |
| 405 | SO$_3$Na | 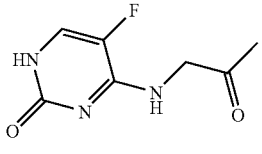 |

TABLE 2-continued

| Compound number | R7 | R8 |
|---|---|---|
| 406 | SO₃H | (structure: H₂N-CH(C(=O)-)-C₆H₄-C(=O)NH₂) |
| 407 | SO₃⁻ | (structure: imidazolyl-C(=O)-piperazinium(N-methyl)-CH₂-C(=O)-) |
| 408 | SO₃Na | (structure: H₂N-C(=O)-C₆H₄-NH-C(=O)-NH-CH₃) |

The numbering of the preferred compounds of formula II as given in above table 2 is used in the following for the sake of conciseness.

The compounds of the above table 2 are, when their compound numbers are underscored and bold, part of the present invention. Otherwise they are disclosed in EP-A-0-508 234, U.S. Pat. No. 6,566,355 and J. Med. Chem. 1998, 3961. These publications are hereby incorporated by reference.

The compounds of formula I may also be combined with other β-lactamase inhibitors. These further inhibitors are:

b2) monobactam derivatives of the above general formula III:

Examples of these compounds are disclosed in WO-A-99/10324 and WO-A-98/47895, incorporated herein by reference. A preferred example of these compounds is 3-{(2E)-3-[(1,5-dihydroxy-4-oxo(2-hydropyridyl))methoxy]-2-(2-thienyl)-3-azaprop-2-enoylamino}(3S,4S)-4-methyl-2-oxoazetidinesulfonic acid disclosed in WO-A-98/47895.

b3) penam sulfone derivatives of the above general formulae IV and V:

Here, preferred examples of the 5-6 membered heteroaromatic ring as R12 are 1,3-thiazol-2-yl, 1,2,4-oxadiazol-3-yl and 1,2,3-triazol-1-yl.

Particularly preferred examples of the compounds of formula V are sulbactam, tazobactam and the compounds of the following table (in parentheses the source):

| R10 | R11 | Compound number |
|---|---|---|
| hydrogen | (1Z)-2-cyanovinyl | 501 EP-A-0 640 607 |
| hydrogen | (1E)-3-oxo-but-1-en-1-yl | 502 EP-A-0 640 607 |
| hydrogen | (1Z)-2-(1,3-thiazol-2-yl)vinyl | 503 EP-A-0 640 607 |
| hydrogen | (1E)-2-(1,2,4-oxadiazol-3-yl)vinyl | 504 EP-A-0 640 607 |
| carboxymethylene | CH₃ | (Bioorg. Med. Chem. Lett. 1995, 1513) |
| hydrogen | (1E)-2-methoxy-2-azavinyl | U.S. Pat. No. 5,686,441 |
| hydrogen | (1E)-2,3-diaza-4-oxo-pent-1-en-1-yl | U.S. Pat. No. 5,686,441 |

The numbers used in the rightmost column of this table are also used in the tests for biological activity (see below).

b4) oxapenam derivatives of the above general formula VI:

A preferred compound of formula VI is clavulanic acid or a customary pharmaceutically acceptable salt thereof (i.e. a clavulanate).

b5) penem derivatives of the above general formula VII:

Here, preferred examples of the 5-6 membered heteroaromatic ring which may be bound over a —CH=CH— spacer as R15 are 1,2,3-triazol-4-yl, 2H,3H-imidazo[2,1-b]1,3-thiazolidin-6-yl and 2'-[1-methyl-1,2,3-triazolin-4-yl]vinylidene.

Preferred examples for inhibitors of formula VII are e.g. 6-[(1-methyl(1,2,3-triazol-4-yl))methylene]-5-oxo-6aH-azetidino[2,1-b]1,3-thiazoline-3-carboxylic acid and 6-(2H,3H-imidazo[2,1-b]1,3-thiazolidin-6-ylmethylene)-5-oxo-6aH-azetidino[2,1-b]1,3-thiazoline-3-carboxylic acid (as described in Antimicrob. Agents Chemother. 1989, 1580 and Antimicrob. Agents Chemother. 1991, 1748), and 6-[(2E)-3-(1-methyl(1,2,3-triazolin-4-yl))prop-2-enylidene]-5-oxo-6aH-azetidino[2,1-b]1,3-thiazoline-3-carboxylic acid (as described in J. Antibiotic 1997, 50, 350).

b6) cephem sulfone derivatives of the above general formula VIII:

Here, a preferred example of the 5-6 membered heteroaromatic ring as R16 is 2-thienyl.

Preferred examples are here 3-(acetyloxymethyl)-1,1,6-trioxo-7-(2-pyridylmethylene)-2H,7aH-azetidino[2,1-b]1,3-thiazine-4-carboxylic acid (Biorg. Med. Chem. Lett. 2000, 853 and Biorg. Med. Chem. Lett. 2000, 847) and 3-(acetyloxymethyl)-7-{[(tert-butyl)oxycarbonyl]methylene}-1,1,6-trioxo-2H,7aH-azetidino[2,1-b]1,3-thiazine-4-carboxylic acid (J. Med. Chem. 1995, 38, 1022).

b7) carbapenem derivatives of the above general formula IX:

Here, preferred combinations for Rk and Rl are: Rk=hydrogen and Rl=sulfamoyl or 3-carboxyphenyl (or vice versa); and Rk=Rl=methyl.

Preferred examples these compounds are imipenem, meropenem, ertapenem and doripenem.

b8) boronate derivatives of the above general formula X.

b9) boronate derivatives of the above general formula XI:

Examples of these compounds are 3-[(4-phenylsulfonyl-2-thienylsulfonyl)amino]phenyl]boronic acid (Chem. Biol. 2001, 8, 593) and [3-[[4-[(4-carboxyphenylsulfonyl)amino]phenylsulfonyl]amino]phenyl]boronic acid (Chem. Biol. 2001, 8, 594).

b10) phosphonate derivatives of the above general formula XII

Preferred examples of these are {[(4-nitrophenoxy)(hydroxyphosphoryl)]methyl}[benzylsulfonyl]amine, {[(4-nitrophenoxy)(hydroxyphosphoryl)]methyl}(phenylsulfonyl)amine and {[(4-nitrophenoxy)(hydroxyphosphoryl)]methyl}(2-thienylsulfonyl)amine, (benzo[b]thiophen-2-ylsulfonyl){[(4-nitrophenoxy)(hydroxyphosphoryl)]methyl}amine and 2-[(4-nitrophenoxy)(hydroxyphosphoryl)]-1-(phenylsulfonyl)hydrazine (all described in US-A-2004/082546 and US-A-2004/029836); and b11) diazabicyclooctane derivatives of the above general formula XIII:

A preferred example of these is (1R,2S,5R) 2-(aminocarbonyl)-7-oxo-1,6-diazabicyclo[3.2.1]octane-6-sulfonic acid (as described in WO-A-2002/01219, WO-A-2002/010172, FR-A-2835186 and FR-A-2848210).

The pharmaceutical compositions of the present invention may comprise, besides the compound of formula I, two or more compounds selected from the above formulae II to XIII, being different from each other. Pharmaceutical compositions comprising triple combinations of a compound of formula I and two different compounds selected from the groups b1) to b11) are a preferred embodiment of the invention.

Preferred combinations for the pharmaceutical compositions of the invention are compounds of formula I, where R1 is SO$_3$H, OSO$_3$H or OCRaRa'COOH, wherein Ra and Ra' are as defined for formula I;

R2, R3 and R5 are as defined for formula I;

R4 is C(Rx)(Ry)Z, with either:

Rx=Ry=H and Z is a group of one of the formulae

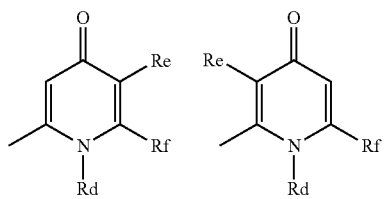

wherein Rd, Re and Rf are as defined for formula I; or

Rx=Ry=methyl and Z=COOH;

or R4 is 4-hydroxypyridino[3,2-b]pyridin-3-yl)methoxy; and R6 is 2-amino-1,3-thiazol-4-yl, 2-amino-5-chloro-1,3-thiazol-4-yl, 5-amino-1,2,4-thiadiazol-3-yl, 5-aminopyrazol-3-yl or 4-aminopyrimidin-2-yl;

with either one of (1S,5R)-2-[2-(3-carbamoylpyridyl)acetyl]-7-oxo-2,6-diazabicyclo[3.2.0]heptane-6-sulfonic acid, (1S,5R)-2-[2-(4-aminopyridyl)acetyl]-7-oxo-2,6-diazabicyclo[3.2.0]heptane-6-sulfonic acid, (1S,5R)-2-[2-(3-carbamoyl-6-methylpyridyl)acetyl]-7-oxo-2,6-diazabicyclo[3.2.0] heptane-6-sulfonic acid, (1S,5R)-2-[2-(5-methyl(1,3,4-thiadiazol-2-ylthio))acetyl]-7-oxo-2,6-diazabicyclo[3.2.0] heptane-6-sulfonic acid, sodium salt, (1S,5R)-2-[2-(1-methyl(1,2,3,4-tetraazol-5-ylthio))acetyl]-7-oxo-2,6-diazabicyclo[3.2.0]heptane-6-sulfonic acid, sodium salt, (1S, 5R)-2-{N-[4-({[2-(2-aminoethoxy)ethyl]amino}carbonylamino)phenyl]carbamoyl}-7-oxo-2,6-diazabicyclo[3.2.0]heptane-6-sulfonic acid, (1S,5R)-2-[N-(4-{[(2-aminoethyl)amino]carbonylamino}phenyl)carbamoyl]-7-oxo-2,6-diazabicyclo[3.2.0]heptane-6-sulfonic acid or (2S,3S,5R)-3-((1Z)-2-cyanovinyl)-3-methyl-4,4,7-trioxo-4-thia-1-azabicyclo[3.2.0]heptane-2-carboxylic acid.

More preferred are composition wherein the above double combinations are further combined with one of sulbactam, clavulanic acid or a customary pharmaceutically acceptable salt thereof, i.e. a clavulanate. These compositions thus comprise triple combinations.

Particularly preferred are compositions with the following double and triple combinations (the numbers are as in the foregoing tables 1a, 1b, 2a and 2b):

| | | |
|---|---|---|
| Aztreonam | Compound 102 | Sulbactam |
| Aztreonam | Compound 102 | Clavulanate |
| Compound 1 | Compound 501 | |
| Compound 1 | Compound 102 | Sulbactam |
| Compound 1 | Compound 102 | Clavulanate |
| Compound 1 | Compound 103 | Clavulanate |
| Compound 1 | Compound 111 | Clavulanate |
| Compound 1 | Compound 202 | Clavulanate |
| Compound 1 | Compound 206 | Clavulanate |
| Compound 1 | Compound 323 | Sulbactam |
| Compound 1 | Compound 323 | Clavulanate |
| Compound 1 | Compound 324 | Clavulanate |
| Compound 12 | Compound 102 | Sulbactam |
| Compound 12 | Compound 102 | Clavulanate |
| Compound 12 | Compound 103 | Sulbactam |
| Compound 12 | Compound 323 | Sulbactam |
| Compound 12 | Compound 324 | Sulbactam |
| Compound 21 | Compound 102 | Sulbactam |
| Compound 21 | Compound 102 | Clavulanate |
| Compound 21 | Compound 323 | Sulbactam |
| Compound 21 | Compound 323 | Clavulanate |
| Compound 21 | Compound 324 | Sulbactam |
| Compound 22 | Compound 102 | Clavulanate |
| Compound 22 | Compound 324 | Clavulanate |
| Compound 22 | Compound 324 | Sulbactam |
| Compound 26 | Compound 102 | Clavulanate |
| Compound 26 | Compound 102 | Sulbactam |
| Compound 26 | Compound 324 | Clavulanate |
| Compound 26 | Compound 324 | Sulbactam |
| Compound 29 | Compound 102 | Sulbactam |
| Compound 29 | Compound 102 | Clavulanate |
| Compound 29 | Compound 323 | Sulbactam |
| Compound 29 | Compound 324 | Sulbactam |

Pharmaceutical compositions with triple combinations of compound no. 1 according to formula I with any one of the compounds of formula II and with clavulanate form a particularly preferred embodiment of the invention, such as do kits-of-parts (articles) with this combination.

The compounds of formula I are compounds known from the above cited literature references, or can be made in an analogous manner, or can be made as described in the following. If in the following schemes a number is assigned to an intermediate then this intermediate is per se presumed novel and may form part of the invention.

The compounds of formula I can generally be prepared by reacting aryl or heteroaryl carboxylic acids of general formula A with 3-amino-azetidin-2-one compounds of general formula B (scheme 1). In this scheme, R4 may also have the meaning of a protecting group, which may then be removed, in order to subsequently connect the actually desired R4.

Scheme 1

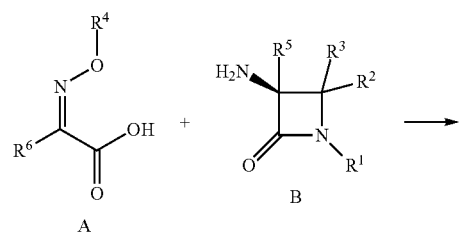

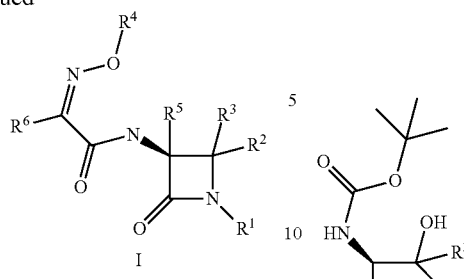

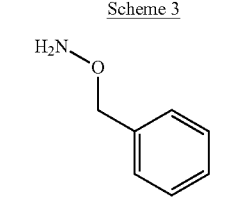

The coupling reaction of compounds of general formula A with compounds of general formula B can be performed with the corresponding acyl chlorides of the aryl or heteroaryl carboxylic acids of general formula A or with the carboxylic acids A themselves and DCC (Chem. Pharm. Bull 1983, 2200) or with an activated ester of the aryl or heteroaryl carboxylic acids of general formula A, such as the N-hydroxysuccinimidyl ester (see Org. Process Res. & Dev. 2002, 863) or the benzothiazolyl thioester (see J. Antibiotics 2000, 1071). Alternatively, compounds of formula I can also be prepared as outlined in scheme 2 (with R1=SO$_3$H see also J. Antibiotics 1985, 346; J. Org. Chem. 1981, 1557).

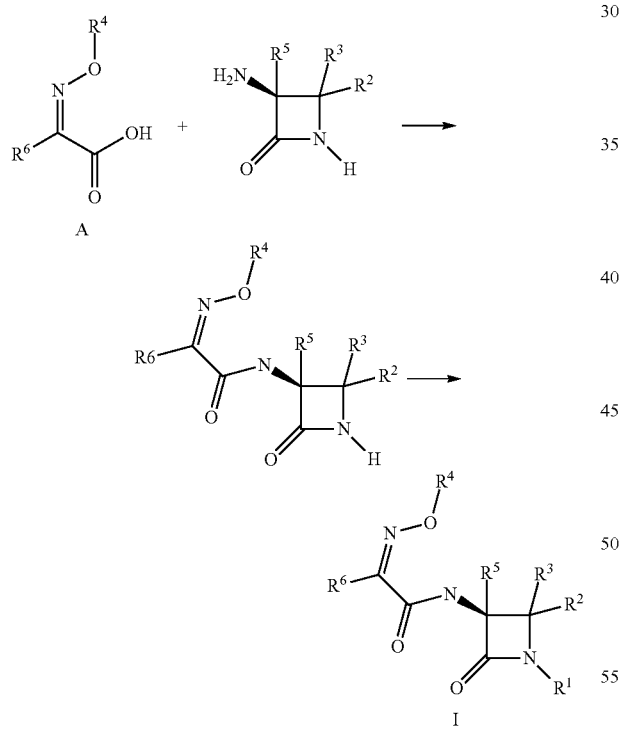

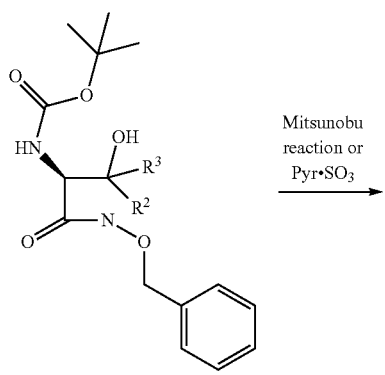

A) Preparation of Compounds B

The preparation of compounds of general formula B can be carried out in different ways according to the substituents present in 1, 3 and 4-positions (Scheme 3, 4, 5). (J. Org. Chem. 1980, 410; J. Org. Chem. 1985, 3462; J. Antibiotics 1985, 346; J. Antibiotics 1985, 813; J. Antibiotics 1986, 76; Tetrahedron Lett. 1986, 2789, J. Med. Chem. 1985, 1447; Chem. Pharm. Bull. 1984, 2646, J. Am. Chem. Soc. 1990, 760).

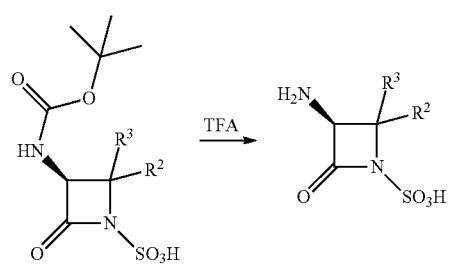

Scheme 4
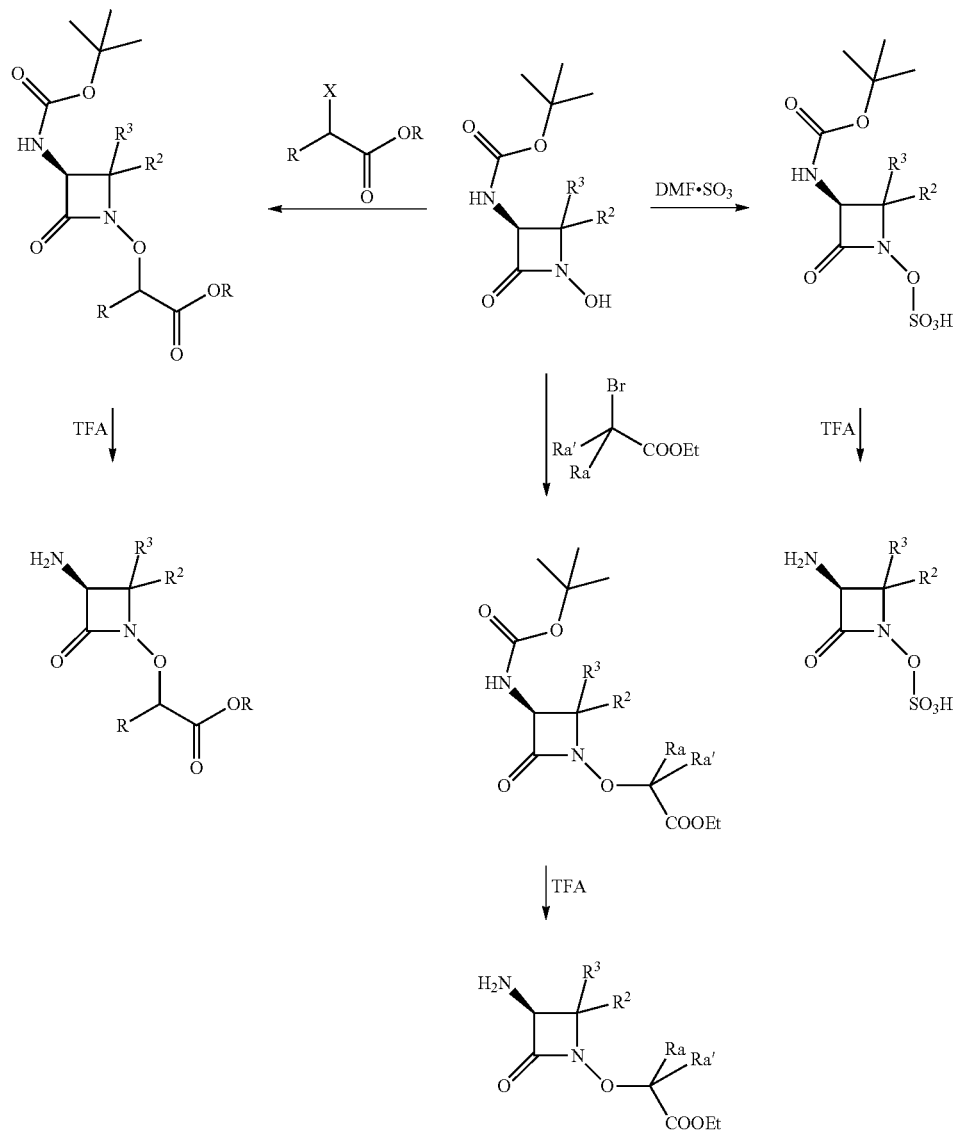
Scheme 5
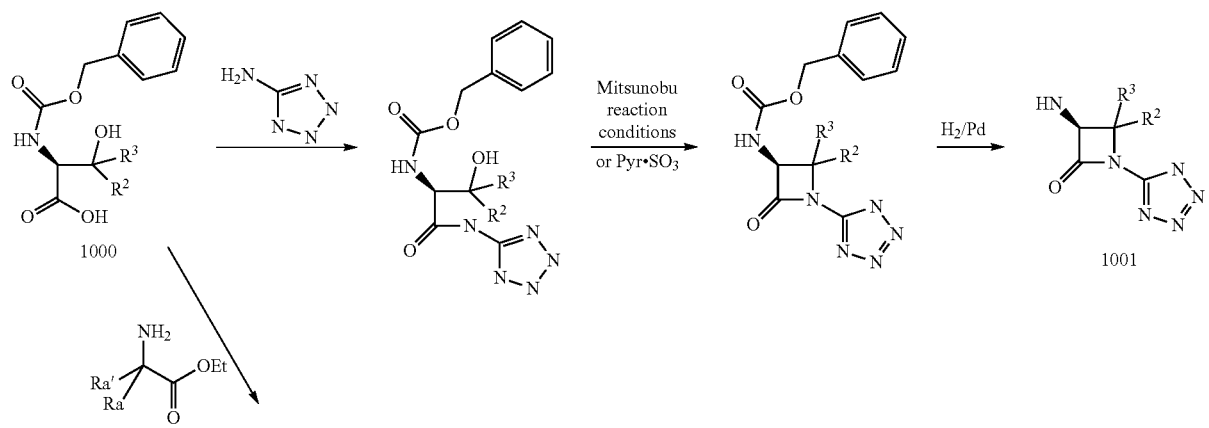

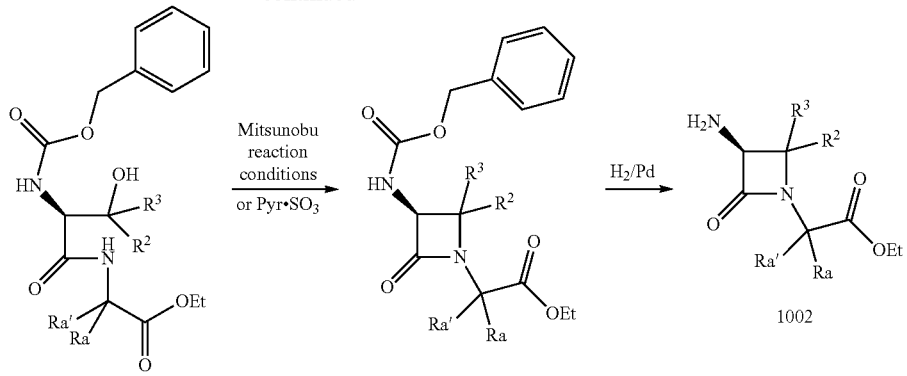

A-1) In the above schemes 3 and 5, generally an enantiomerically pure N-protected β-hydroxy amino acid 1000 is required as the starting material. This precursor 1000 can be prepared in different ways, as outlined in the following sections A-1-I) to A-1-IV):

A-1-I) Where $R^2=R^3=R$ and preferably is alkyl, alkenyl, alkynyl, optionally substituted benzyl or optionally substituted phenyl, a synthesis according to the following scheme A-1-I or scheme A-1-Ia may be used:

Scheme A-1-I

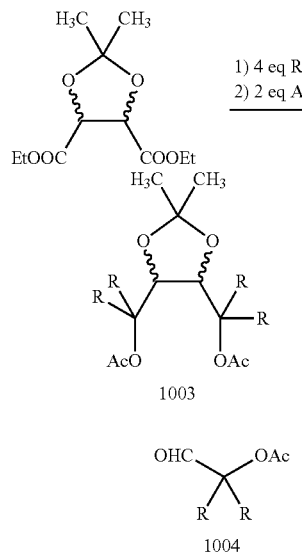

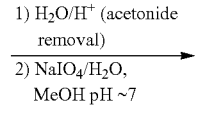

1004

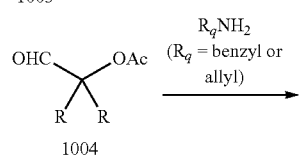

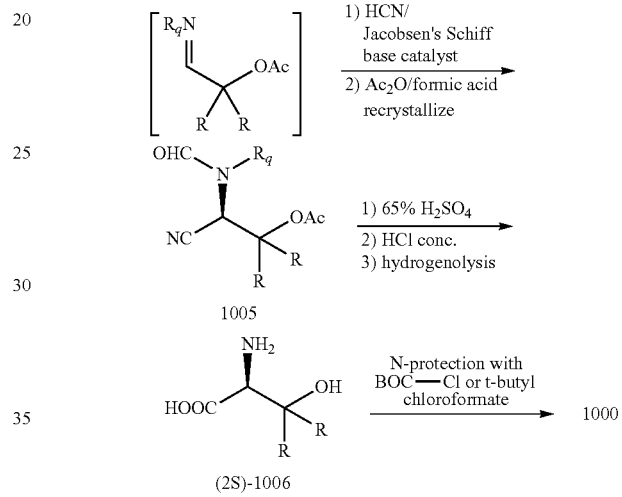

In the above scheme A-1-I, the configuration of the α-carbon atoms in the starting diethyl tartrate needs not be defined. The indicated chiral Jacobsen's catalyst for the asymmetric Strecker synthesis of the amino acid (2S)-1006 has been known from Angew. Chem. Int. Ed. 2000 1279. As the catalyst is available in both enantiomers, the corresponding β-hydroxy amino acid with the D-configuration at the α carbon atom ((2R)-1006) may also be produced. The latter is suited for producing N-protected β hydroxy amino acids 1000a where the hydrogen atom at the α carbon atom is replaced by R5 (see section A-1-IV below).

Scheme A-1-Ia

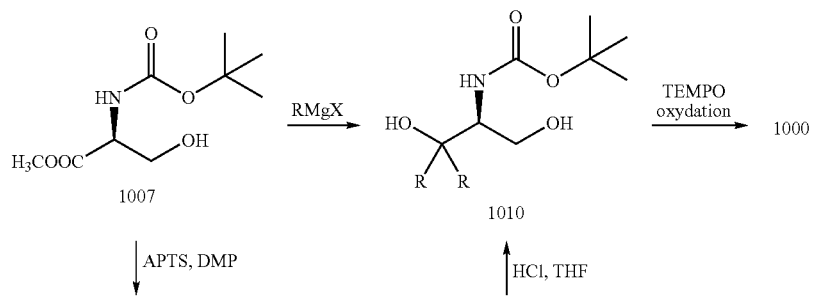

-continued

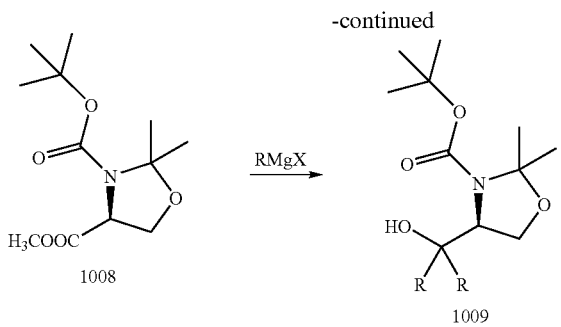

In the above scheme A-1-Ia, the preparation of the β,β-dialkylsubstituted β-hydroxy α-amino acid 1000 starts from the commercially available enantiomerically pure N—BOC serine methyl ester 1007 (J. Org. Chem. 2003, 177, Tetrahedron, 1996, 11673). The synthesis follows the chemistry based on Rapoport's methodology, which is known to keep the conformational integrity of the starting amino acid (J. Org. Chem. 1989, 1866, J. Org. Chem. 1990, 3511).

A-1-II) Similarly, where $R^2$ and $R^3$ are different from each other and are preferably independently selected from alkyl, alkenyl, alkynyl, optionally substituted benzyl and optionally substituted phenyl, the following scheme A-1-II, modified from scheme A-1-I, may be used to produce 1000:

Scheme A-1-II

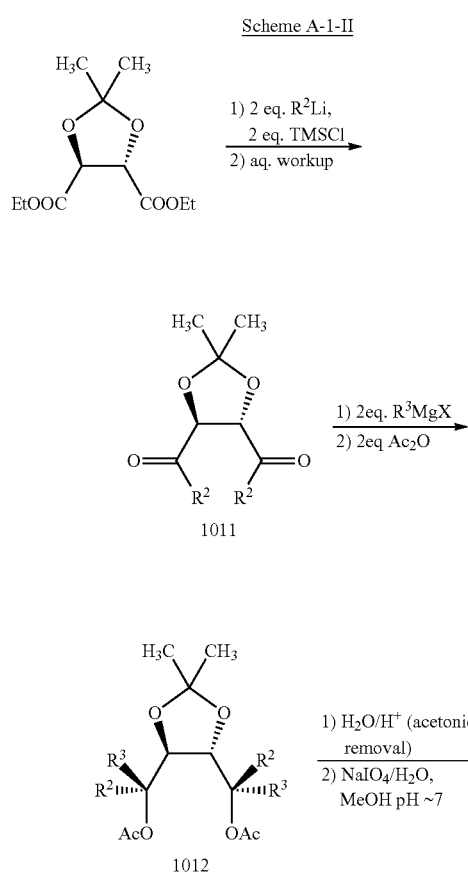

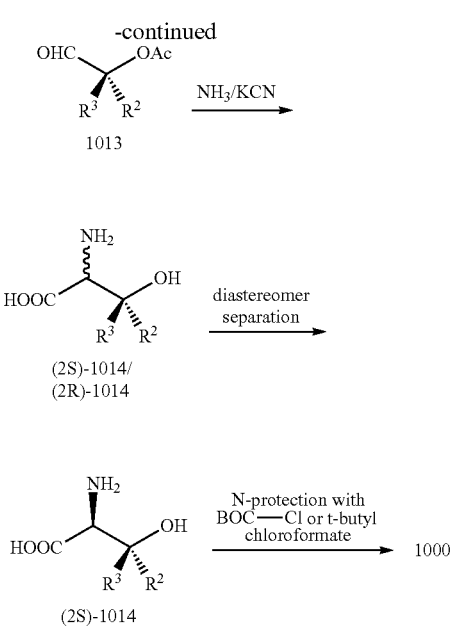

In this scheme $R^2$ is particularly preferably methyl. The introduction of the second residue $R^3$ into 1011 by Grignard reaction gives, according to Cram, predominantly the shown diastereomer of 1012, due to the chelating effect of the oxygen atom of the α-acetonide substituent. In the Strecker synthesis step without chiral auxiliary, both diastereomeric amino acids (2S)-1014 and (2R)-1014 may form as a mixture due to the newly formed chiral α-carbon atoms. The diastereomers of the so produced β-hydroxy amino acids 1014 may be separated using ion exchange chromatography with aqueous buffers as the mobile phase, as is customary in the art. The correct diastereomer (2S)-1014 may be identified as the one that produces faster a dipeptide, when each of the diastereomers (2S)-1014 and (2R)-1014 is reacted under otherwise identical conditions with N-benzoyl L-alanine methyl ester and carboxypeptidase Y as the dipeptide-forming enzyme (for an appropriate experimental procedure see example 1 of EP-A-0 017 485). The other, undesired diasteromer (2R)-1014 may be used for the production of N-protected β-hydroxy amino acids 1000a where the hydrogen atom at the α carbon atom is replaced by $R^5$ other than hydrogen (see section A-1-IV below).

Scheme A-1-IIa

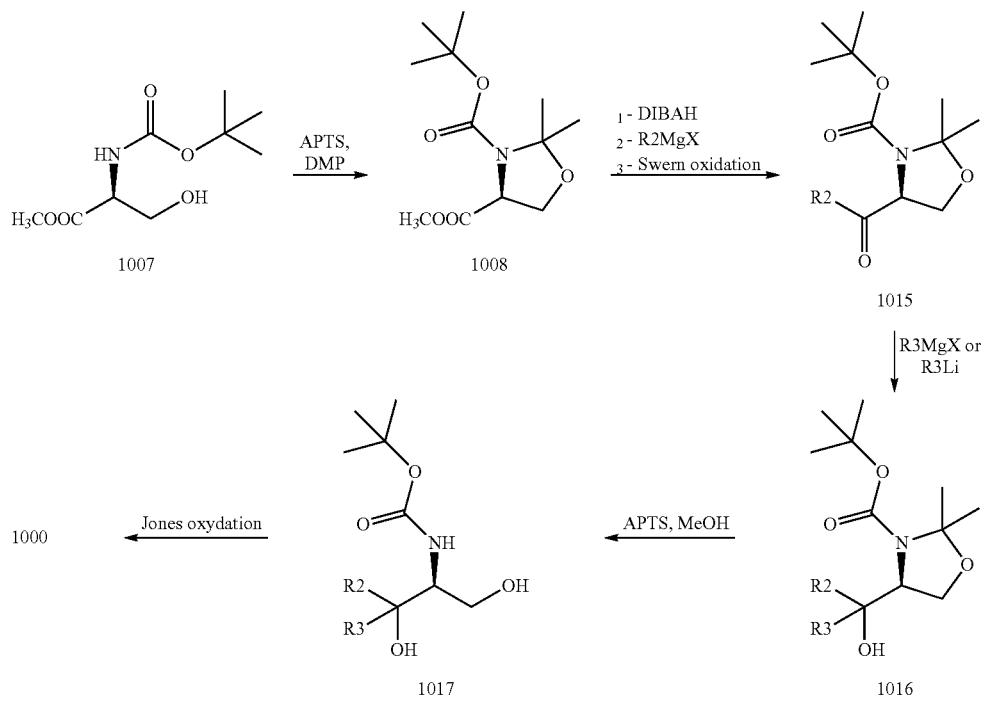

Scheme A-1-IIa outlines an alternative procedure starting from protected serine 1007 and leading to disubstituted hydroxyl derivatives 1016 by controlling the stereochemistry of the addition of the second substituent; either with R3Li, giving the Felkin adduct as major product, or with R3MgX, to obtain the anti-Felkin adduct as major product (Tetrahedron 1995, 8121).

A-1-III) where $R^2$ is preferably alkyl, alkenyl, alkynyl, optionally substituted benzyl or optionally substituted phenyl, and $R^3$ is H, or $R^2$ is H and $R^3$ is preferably alkyl, alkenyl, alkynyl, optionally substituted benzyl or optionally substituted phenyl, a synthesis according to following scheme A-1-III) may be adopted to form 1000:

Scheme A-1-III

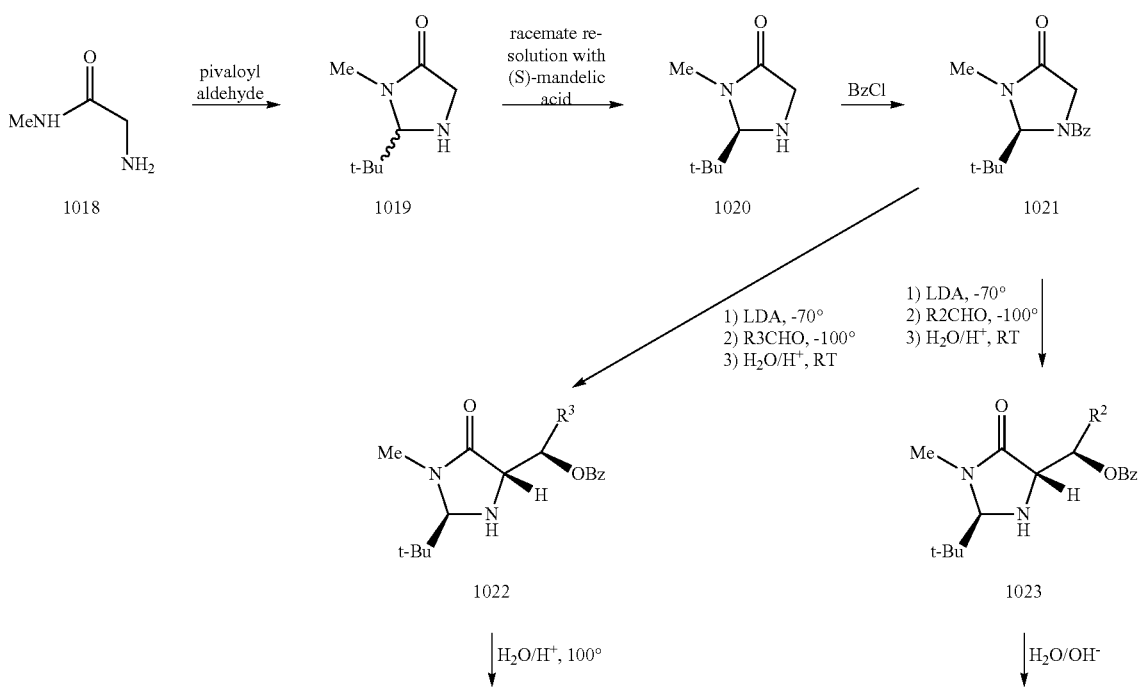

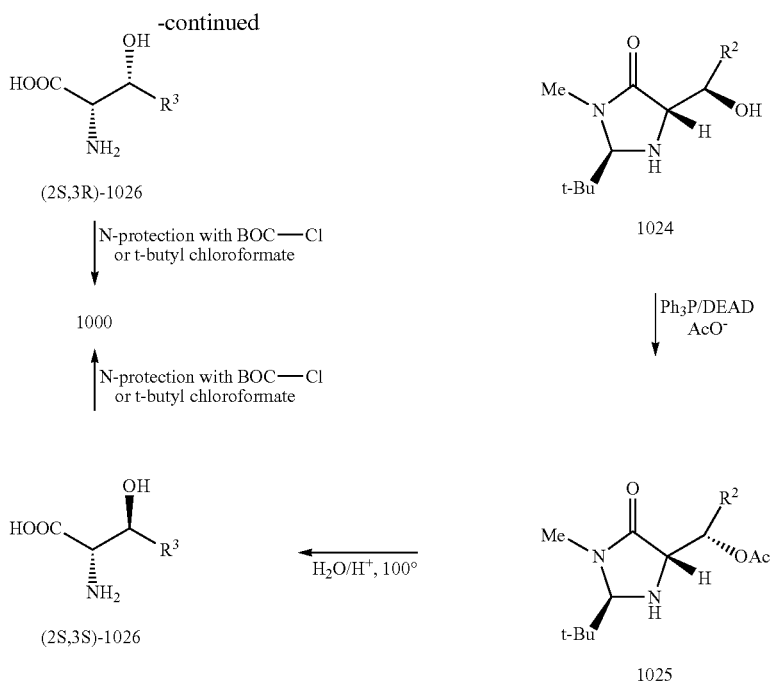

This methodology was developed by Seebach (Helv. Chim. Acta 1987. 237). In scheme A-1-III, the conversions on the left pathway yield the N-protected β-hydroxy amino acid 1000 where $R^2$=hydrogen, in defined configuration. The conversions on the right pathway yield the N-protected β-hydroxy amino acid 1000 where $R^3$=hydrogen, also in defined configuration.

A-1-IV) When the azetidinone B contains R5 other than hydrogen, then an N-protected α-$R^5$-substituted β-hydroxy amino acid 1000a is required, analogous to a corresponding above amino acid 1000, except for the additional R5 substituent. This amino acid 1000a may be used in above schemes 3 and 5 instead of 1000.

A-1-IVa) When R5 is preferably alkyl, and one of R2 and R3 is preferably hydrogen, and the other one preferably is alkyl, alkenyl, alkynyl, optionally substituted phenyl or optionally substituted benzyl (or both of R2 and R3 are preferably independently selected from alkyl, alkenyl, alkynyl, optionally substituted phenyl and optionally substituted benzyl) the technology described in part A-1-III (Helv. Chim. Acta 1987. 237) can be employed, but using 2-tert-butyl-N-benzoyl-1,3-oxazolidinone as chiral inductor (scheme A-1-IVa below). The introduction of the electrophile R5-X leads to the compound 1029. A condensation with aldehyde R2CHO as second electrophile gives the R2,R5-disubstituted oxazolidinone 1030 with control of the stereochemistry. If desired, the configuration at the newly formed secondary alcohol in 1030 may be inverted, such as under Mitsunobu conditions, to form the epimeric R2,R5-disubstituted oxazolidinone 1031. If onto 1029 a condensation with ketone R2C(O)R3 as the second electrophile is carried out, then R2,R3,R5-trisubstituted oxazolidinones 1032 may be produced. If necessary the formed epimers of 1032 may be separated, such as by chromatography. All three compounds 1030, 1031 and 1032 may subsequently be converted by hydrolysis of the benzoyl group and the oxazolidinone ring and reprotection of the amino group desired compounds 1000a.

Scheme A-1-IVa

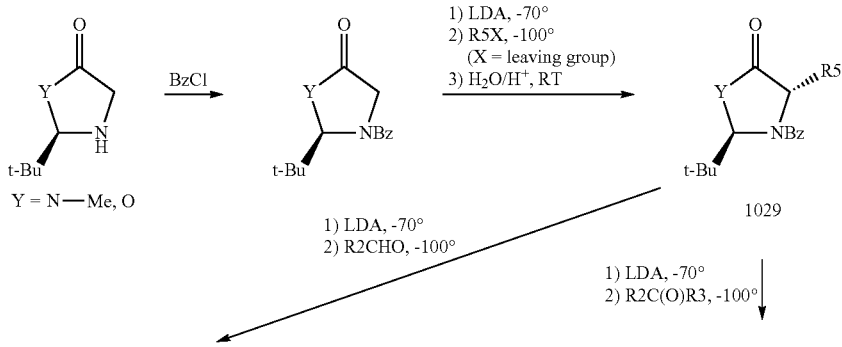

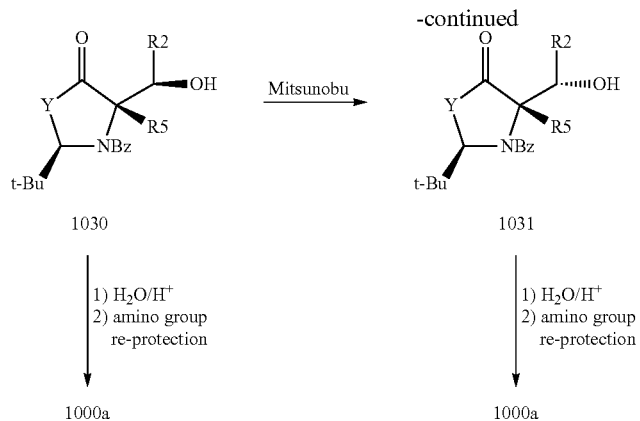
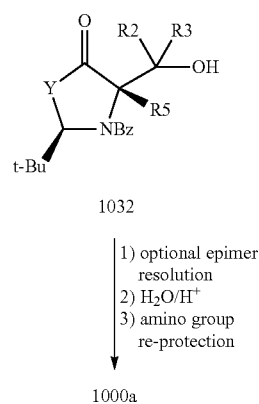

A-1-IVb) When the azetidinone B contains alkoxy as R5 and one of R3 or R2 preferably as hydrogen, and the other one preferably as alkyl, alkenyl, alkynyl, optionally substituted phenyl or optionally substituted benzyl, then another example of preparation of amino acids 1000a is outlined in following scheme A-1-IVb (in the scheme R3 is assumed as hydrogen). It is based on the chemical description written on Biochemistry 2004, 3385 and Fortschr. Chem. Org. Naturst., 1979, 327. The approach relies on the established oxidation of an N-acyl α-amino ester to a highly reactive intermediate N-acyl α-imino ester, which then adds R5-containing nucleophiles (alcohols R'''OH wherein R'''O=R5). The various protecting groups R' and R'' would be removed subsequently (not shown in the scheme).

A-1-IVc) Similarly, for the case where azetidinone B contains alkoxy as R5 and both R3 and R2 are preferably independently selected from alkyl, alkenyl, alkynyl, optionally substituted phenyl and optionally substituted benzyl, an approach acccording to following scheme A-1-IVc may be used. By this scheme it is possible to prepare β-disubstituted N-protected amino acids 1000a following the synthetic pathway described in scheme A-1-Ia and scheme A-1-IIa.

Scheme A-1-IVb

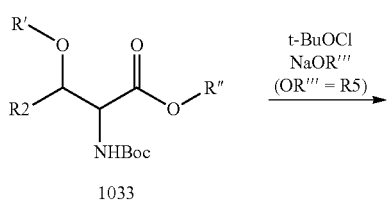

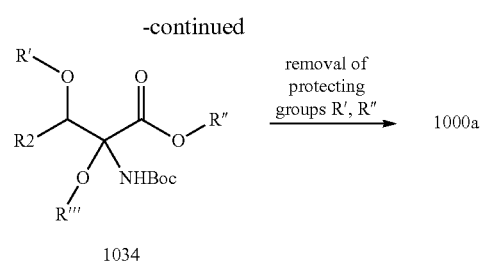

Scheme A-1-IVc

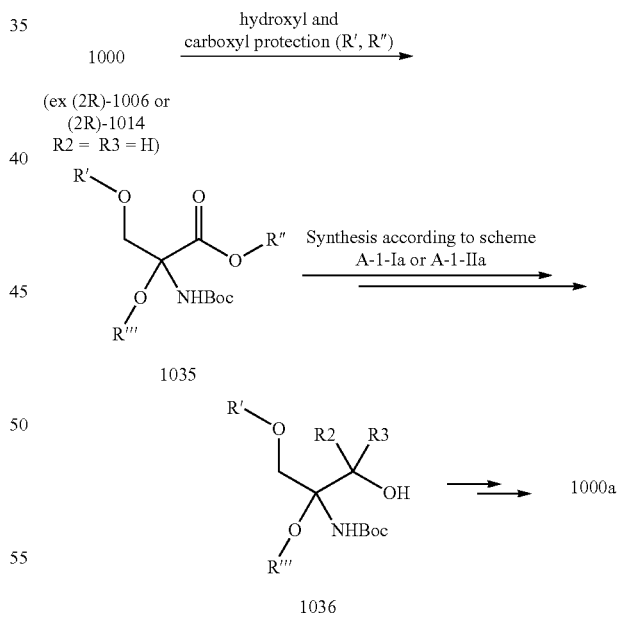

In above scheme A-1-IVc, the conversions 1000 to 1035 are analogous to the conversions of 1000 to 1034 in above scheme A-1-IVb.

A-2) A range of compounds B, where R2=CH$_2$X1 and R3=H, can be directly made in analogy to the procedure described in J. Antibiotics, 1983 1201 followed by standard functional group conversions (scheme A-2):

Scheme A-2

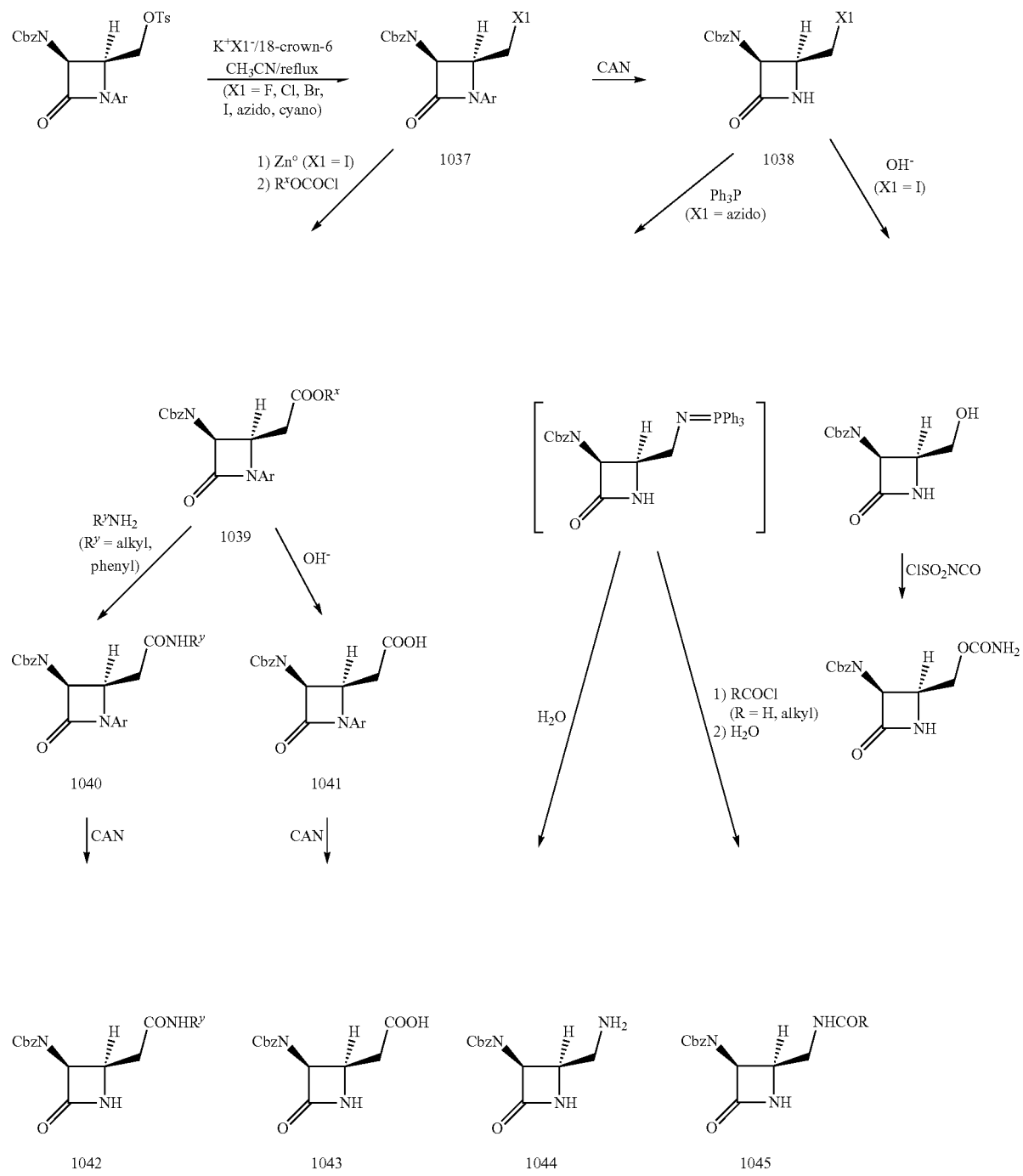

This scheme shows how to form compounds B where X1 is preferably selected from halogen, azido, amino, hydroxyl, cyano, carboxyl, alkoxycarbonyl, alkanoylamino, phenylaminocarbonyl, alkylaminocarbonyl, aminocarbonyl, carbamoyloxy, alkylaminosulfonyl and optionally substituted phenylaminosulfonyl. The common starting material shown in the upper left of scheme A-2 is known from J. Org. Chem. 1982. 2765. In this scheme, in all the obtained compounds B the final removal of the Cbz protecting group by hydrogenolysis is not shown.

B) Preparation of Compounds A

The preparation of compounds of general formula A required in schemes 1 and 2 can be carried out in a customary way by reacting an appropriately R6-substituted keto acid A3 with an appropriately R4-etherified hydroxylamine (schemes 6 and 7 below)

Scheme 6

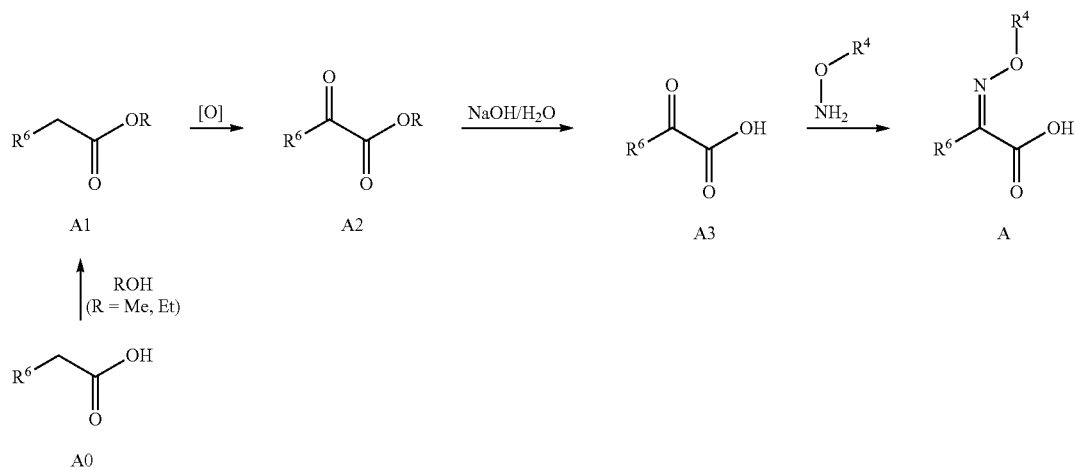

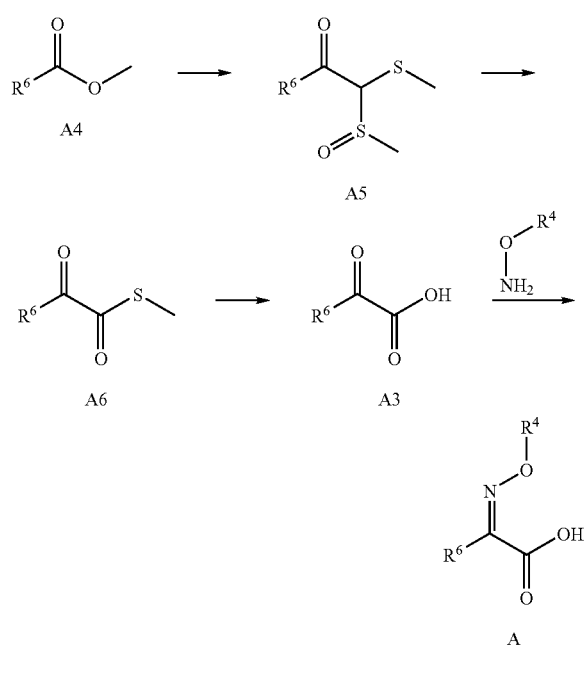

The R6-substituted keto acid A3 required in both schemes 6 and 7 can be prepared via 2 different synthetic pathways, as described in the following.

A3 may firstly be obtained by oxidation of an ester A1 leading to the glyoxalate derivative A2, followed by hydrolysis of the ester group (scheme 6). The oxidising agent used in the conversion from A1 to A2 is not critical. Examples of suited oxidising agents are $SeO_2$ (J. Antibiotics 1983, p. 1020ff.), DMSO, $X_2$ (Bull. Chem. Soc. Jpn. 1994, 1701), $X_2$ and pyridine-N-oxide (Biorg. Med. Chem. 2003, 591) where $X_2$ is a halogen; with $SeO_2$ being preferred.

The R6-substituted keto acid A3 can also be prepared via the condensation of methyl methylthiomethyl sulfoxide according to above scheme 7 (J. Antibiotics, 1984, 546, J. Antibiotics, 1984, 557) in a 4 step synthesis from the esters A4 $R6COOCH_3$ or R6COOEt. The methyl methylthiomethylsulfoxide is first condensed with A4 derivatives to give the methyl thioglyoxylate compound A6 after acidic treatment.

Examples of preparation of intermediates A0, A1 or A4 (scheme 6 and 7) are as outlined in the following subsections B-1-Ia) to B-2-Id). Some of these intermediates are also commercially available.

B-1-I) R6 can be a 5 membered heteroaromatic ring containing 1 to 4 heteroatoms such as N, O, S and which may be substituted with 1 to 4 substituents selected from alkyl, hydroxyl, alkoxy, amino, alkylamino, carbonylamino and halogen such as F, Cl, Br or I, preferably Cl.

B-1-Ia) Thiadiazole Derivatives

The preparation of derivatives A0, A1 or A4, where R6 is a thiadiazole, especially 1,2,4-thiadiazole, may be performed as described in Biorg. Med. Chem. 2006, 1644, included herein by reference. Examples of compounds A1, may be prepared starting from 3-amino-5-methoxyisoxazole or methyl amidine in presence of thioesters, potassium thiocyanate or isothiocyanate as outlined in scheme B-1-Ia (Bull Chem Soc Jpn. 1994, 1701, J. Antibiotics 1983, 1020). In this scheme, R is preferably selected from hydrogen, alkyl, alkoxy, amino, alkylamino and carbonylamino.

Scheme B-1-Ia

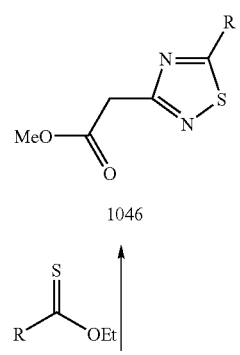

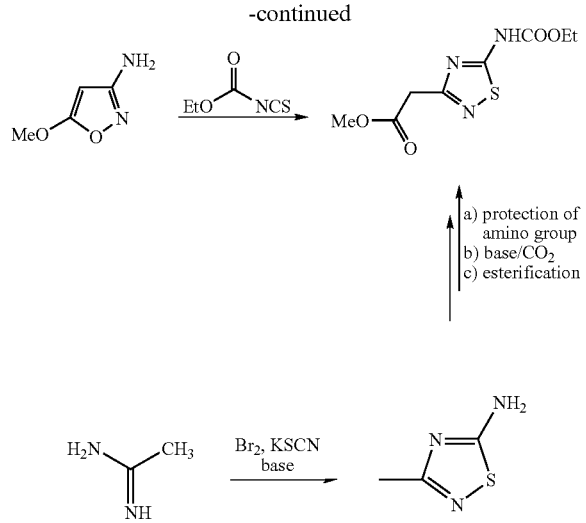

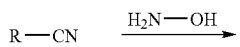

B-1-Ib) Scheme B-1-Ib outlines examples of starting materials A0, A1 and A4 (Helv. Chim. Acta 1982, 2606; Russ. J. Org. Chem. 2003; 1133, Tetrahedron Let. 1979, 2827) obtained from substituted thiohydrazines. Using BrCN and these as starting material, 1049 may by prepared and then can lead to 2-amino-(1,3,4-thiadiazol-5-yl)acetic acid 1050. In scheme B-1-Ib, R is preferably selected from hydrogen, alkyl, alkoxy, amino, alkylamino and carbonylamino.

In the above schemes B-1-Ia and B-1-Ib, the reaction with base/CO$_2$, optionally by silyl protection of the amino group, may be carried out according to J. Antibiotics, 1984, 532 already cited above.

B-1-Ic) 1,2,4-oxadiazole Derivatives

As outlined in the upper part of scheme B-1-Ic indicated below, amide oxime derivatives 1051, wherein R is preferably selected from hydrogen, alkyl and alkoxy may be reacted with compounds such as carboxylic acid, acyl chloride or cyano derivatives to form 1,2,4-oxadiazole rings 1052, which are new examples of heterocycles derivatives A1. The lower part of scheme B-1-Ic, wherein R' is preferably selected from hydrogen, alkyl, alkoxy, carbonylamino and halogen (in particular Cl), shows the synthesis of carboxylates 1054, 1056 of type A1 which are isomeric to 1052 (Tetrahedron Lett. 1998, 3931, J. Org. Chem. 1995, 3112, J. Med. Chem. 1990, 1128, J. Pep. Research 2003, 233, Z. Chem. 1975, 57). For instance, compound 1056 may be obtained from the condensation of 1055 with BrCN.

Scheme B-1-Ic

R—CN $\xrightarrow{H_2N-OH}$

Scheme B-1-Ib

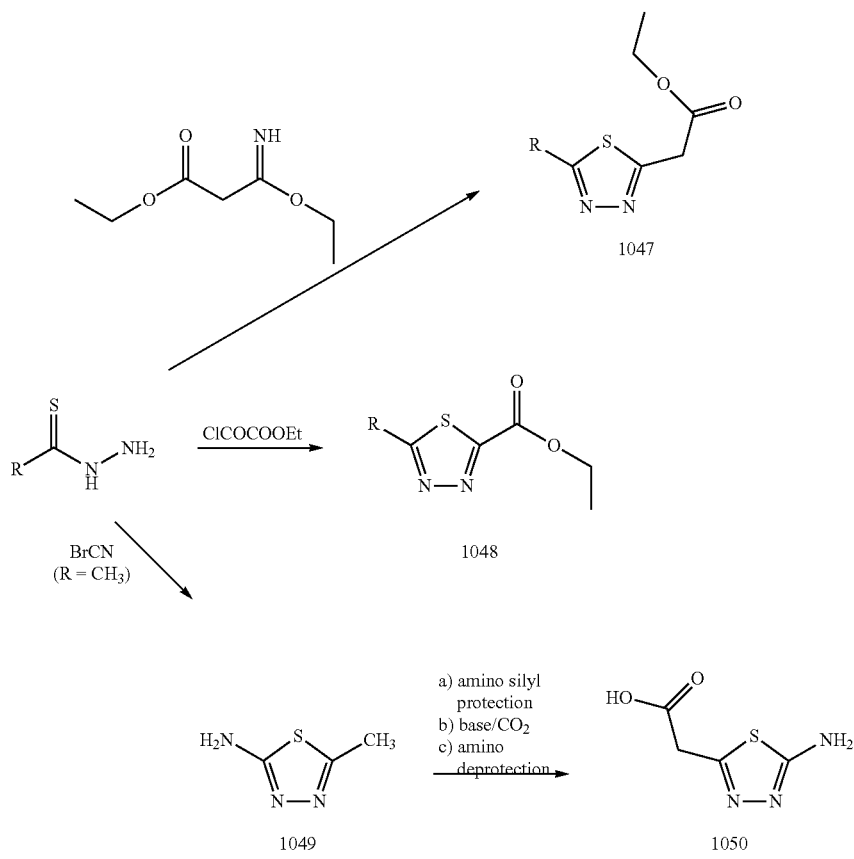

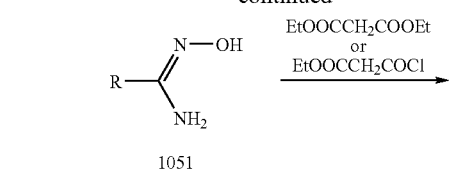

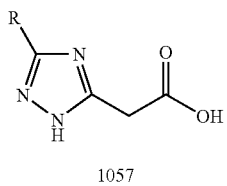

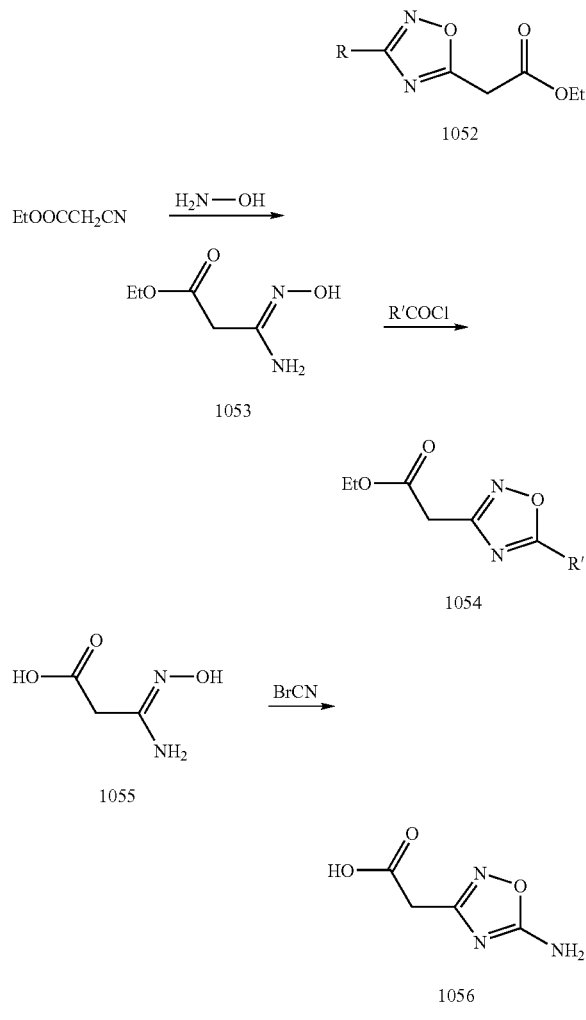

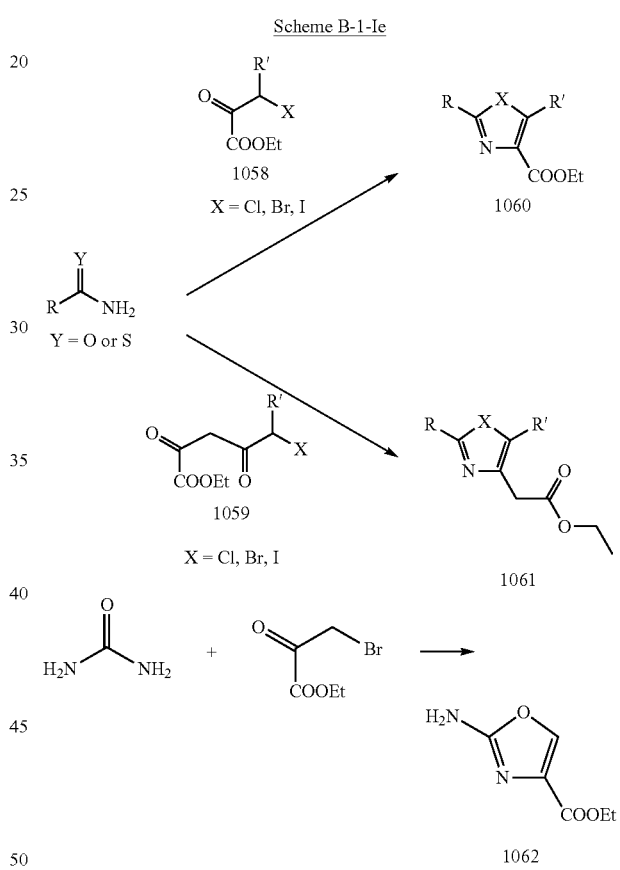

B-1-Ie) Thiazole and Oxazole Derivatives

A versatile way for forming intermediates A0, A1 or A4, wherein the residue R6 is an optionally substituted 1,3-thiazol-4-yl or 1,3-oxazol-4-yl, is according to the known reactions of a thioamide or amide with an α-haloketone derivatives, as outlined in scheme B-1-Ie):

B-1-Id) Triazole Derivatives

Other examples of acids A0 outlined in scheme B-1-Id shown below are triazolyl acetic acid derivatives, such as 1,2,4-triazolyl acetic acids 1057, which may optionally be substituted by one substituent R preferably selected from amino, alkyl, alkoxy and carbonylamino. The exemplary synthesis of 2-(5-amino-1,2,4-triazol-3-yl)acetic acid (R=NH$_2$) by this scheme is known from Russ. J. Org. Chem. 1995, 240.

In this scheme, R may preferably be selected from hydrogen, alkyl, alkoxy, amino, and alkylamino; and R' is preferably selected from hydrogen and alkyl. From substituted thioamides, and substituted ethyl halogeno pyruvate 1058 or compounds 1059 substituted 1,3-thiazol-4-yls 1060, 1061 may be obtained according to examples described in the literature such as Tetrahedron Lett. 2005, 66; J. Chem. Soc. 1966, 1357; J. Chem. Soc. 1960, 925; J. Med. Chem. 1971, 1075; J. Het. Chem. 1980, 1255; J. Med. Pharm. Chem. 1959, 577.

From similar keto ester derivatives 1059 in the presences of amide or thioamide derivatives, substituted 1,3-oxazol-4-yl acetic acid esters may be prepared as reported for instance in Bioorg. Med. Chem., 2003, 4325; Heterocycles, 2001, 689; Chem. Pharm. Bull. 1986, 2840; Tetrahedron Lett. 1992, Scheme B-1-Id

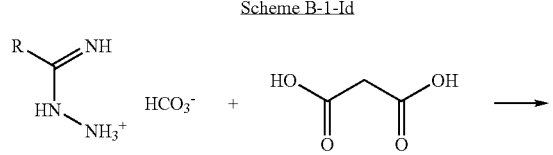

1937. The preparation of compounds 1062 from urea with ethyl bromo pyruvate is an example of preparation of 1,3-oxazole derivatives. If R' is hydrogen and X is sulphur, then the thiazole moiety in 1060 or 1061 may subsequently be chlorinated using the procedure as described in "Preparation 1" of EP-A-0 055 465.

B-1-If) Pyrazole Derivatives.

Another example of heterocyclic intermediates A0, A1 or A4 may be synthesised from substituted ethyl pyruvates in presence of hydrazine or substituted hydrazines according to the scheme B-1-If (J. Chem. Soc. 1945, 114; Helv. Chim. Acta 1955, 670, J. Am. Chem. Soc. 1959, 2456). In this scheme, R is preferably selected from hydrogen, alkyl and carbonylamino, and R' is preferably selected from hydrogen, alkyl, alkoxy, carbonylamino, hydroxyl, amino, alkylamino and halogen (in particular Cl).

Scheme B-1-If

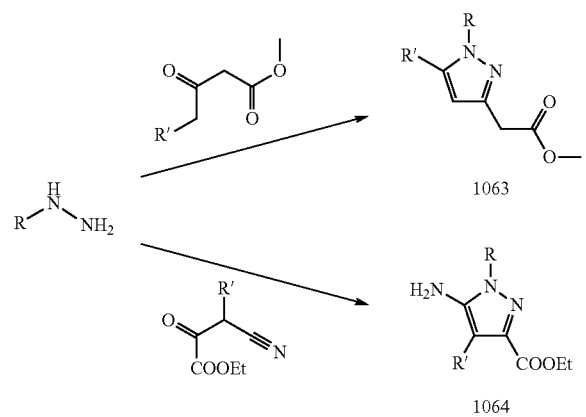

The reaction shown in the lower part of the scheme is analogous to a synthesis described in J. Org. Chem. 2004, 5168.

B-1-Ig) Isoxazole Derivatives

Many isoxazoles with a carboxyl substituent in the 3-position and with one or two substituents selected from amino, alkyl (in particular methyl and ethyl) and hydroxyl are commercially available. Similar commercially available isoxazoles with a methyl substituent in the 3-position and optionally one or two substituents R' and R" preferably independently selected from alkyl, alkoxy and halogen, may again be converted to corresponding carboxylate-containing isoxazoles by converting that 3-methyl substituent to carboxylate using base and carbon dioxide (scheme B-1-Ig). For example, in U.S. Pat. No. 4,394,504 3-amino-5-isoxazolyl-2-acetic acid 1065 was prepared from 3-amino-5-methylisoxazole in this way.

Scheme B-1-Ig

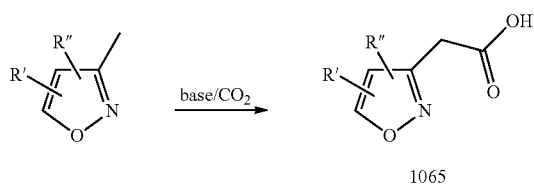

B-2) R6 can also be a phenyl ring which may be substituted with 1 to 5 substituents selected from alkyl, hydroxyl, alkoxy, amino, alkylamino, carbonylamino and halogen or a 6-membered heteroaromatic ring containing 1 to 5 heteroatoms such as N and which may be substituted with 1 to 5 substituents selected from alkyl, hydroxyl, alkoxy, amino, alkylamino, carbonylamino and halogen (such as F, Cl, Br, I, preferably Cl).

B-2-Ia) A very general way of obtaining keto acids A3 for above schemes 6 and 7 is by direct Friedel-Crafts acylation of an appropiately substituted corresponding phenyl or heterocycle R6-H, using excess oxalyl chloride. This way is feasible for all keto acids A3 where R6 is phenyl or a heterocycle which may be substituted by one to five substituents selected from alkyl, alkoxy, dialkylamino and halogen (in particular chloro), with the proviso that the phenyl or heterocycle has at least one unsubstituted carbon atom (the carbon atom that will carry the gyloxaloyl substituent). The appropriately substituted corresponding phenyl or heterocycle R6-H (where H is bonded to the said unsubstituted carbon atom) is reacted with excess oxalyl chloride under Friedel-Crafts conditions, followed by removal of excess oxalyl chloride and hydrolysis of the remaining free acyl chloride group of the introduced glyoxaloyl moiety. Friedel-Crafts acylation is also feasible for such phenyls or heterocycles where some of the one to five substituents are hydroxyl, amino, alkylamino. These substituents, however, are preferably protected as the before the acylation step and the subsequently deprotected.

B-2-Ib) Examples of intermediates A4 are commercially available pyridinecarboxylic acids, such as picoline (2-pyridinecarboxylic acids), nicotinic acid (3-pyridinecarboxylic acids) or isonicotinic acid (3-pyridinecarboxylic acids), which may optionally be substituted at the pyridyl by a substituent selected from alkoxy, halogen (in particular chloro) and amino.

B-2-Ic) Further examples of acids A0 are 2-pyridyl acetic acids, such as 2-(pyridyl-2) acetic acids 2-(pyridyl-3) acetic acids or 2-(pyridyl-4) acetic acids which may optionally be substituted at the pyridyl by a substituent selected from alkoxy, halogen (in particular chloro) and amino.

These can be obtained by deprotonating an appropriately substituted methylpyridine with a strong base such as N-BuLi or LDA and reacting the anion with carbon dioxide. In this reaction, the methyl substituent of the methylpyridine is at the position where the acetic acid will be. The optional amino substituent at the pyridine may have been appropriately protected beforehand, such as with TMS-Cl. An exemplary reaction of this type can be found in DE-OS-2848912 and J. Antibiotics 1984, 532.

B-2-Id) R6 can also be a pyrimidine derivative.

Scheme B-2-Id (below) shows that amidine derivatives (J. Org. Chem. 1962, 3608) can lead to either 2-substituted pyrimidine A1 or A4 (DE-OS-2848912, J. Antibiotics 1984, 546). Compounds 1068 (R=Cl) can easily be obtained by reaction with phosphoryl chloride from 1067. The chlorine can then easily be substituted by nucleophiles such as ammonia, alkylamines or alcohols and lead to compounds 1068 with R=amino, alkylamino or alkoxy (J. Antibiotics 1984, 546).

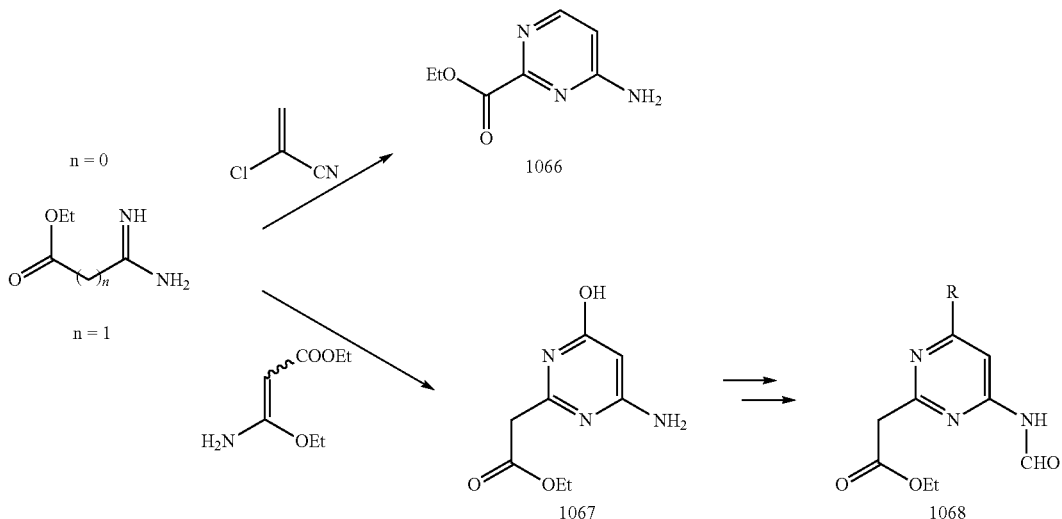

Scheme B-2-Id

Another group of commercially available or synthetically accessible esters A4 are pyrimidyl-4 (ethyl 5,6-diaminopyrimidine-4-carboxylate, ethyl 2-amino-5-chloropyrimidine-4-carboxylate), pyrimidyl-5 (ethyl 2,4-diaminopyrimidine-5-carboxylate, ethyl 2-chloro-4-amino-5-carboxylate, ethyl 2,4-dichloropyrimidine-5-carboxylate) or pyrimidyl-6 (ethyl 2-chloro-4-amino-pyrimidine-6-carboxylate, ethyl 4,5-diaminopyrimidine 6-carboxylate) which are also considered as examples of 6-membered heterocyclic rings as R6 (Tetrahedron Lett. 1967, 1099; Chem. Pharm. Bull. 1970, 1003. Justus Liebig Ann. Chem. 1954, 45).

B-3) The hydroxylamines required in both above schemes 6 and 7, can be prepared in several methods, as outlined in scheme 8 below.

These hydroxylamines may be prepared firstly according to J. Antibiotics, 2000, 1072 with N-hydroxyphthalimide via Mitsunobu reaction conditions in presence of the alcohols R4-OH or by alkylation of N-hydroxyphthalimide in presence of activated compounds R4-X (X can be halogens like Cl, Br, I, or activated sulfonate esters like mesylate, tosylate, triflate, etc.). When R4 has the structure C(Rx)(Ry)Z, with both Rx and Ry different from hydrogen, or is a tertiary alkyl, then N-hydroxyphthalimide may simply be treated with a stoichiometric amount of $BF_3 \cdot Et_2O$ with the corresponding alcohol R4-OH (Tetrahedron Lett., 2005, 6667). Formation of the final hydroxylamines may be performed in presence of either hydrazine or methyl hydrazine. The oxaziridine technology developed by Ellman can also been employed to give directly deprotected O-substituted hydroxylamines (J. Org. Chem. 1999, 6528). (scheme 8).

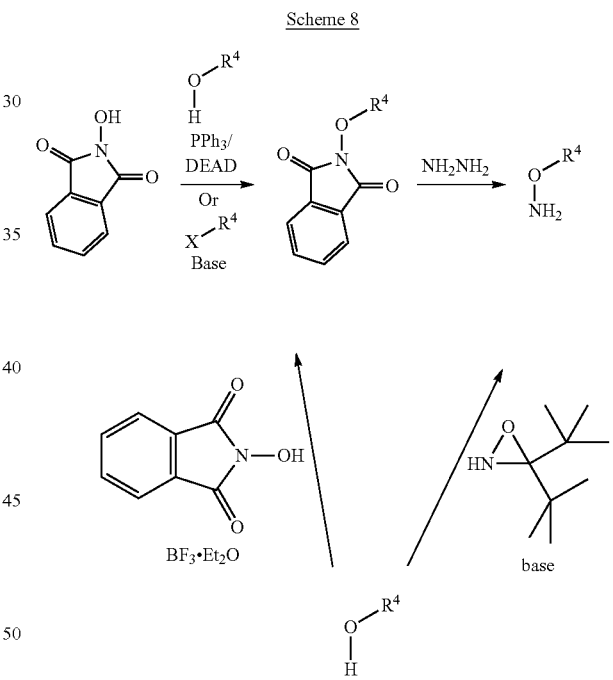

Scheme 8

Alcohols R4-OH or compounds R4-X are either commercially available or may be prepared as described in following sections B-3-Ia) to B-3-Ie).

B-3-Ia) A first method, where R4 is C(Rx) (Ry)Z, with Z=CH₂N(OH)COR', is outlined, as example, in the following scheme B-3-Ia, using α-halogenoalcohols 1069 or 1071 and N-Boc-O-(p-methoxybenzyl)hydroxylamine. The α-halogenoalcohols 1071 can be prepared from derivatized epoxides 1070 which can be opened in acidic conditions (Eur. J. Org. Chem. 2004, 2557). The α-halogenoalcohols 1069 can be obtained by chiral reduction of corresponding α-halogenoketones (Tetrahedron:Asymmetry 2005, 3955).

Scheme B-3-Ia

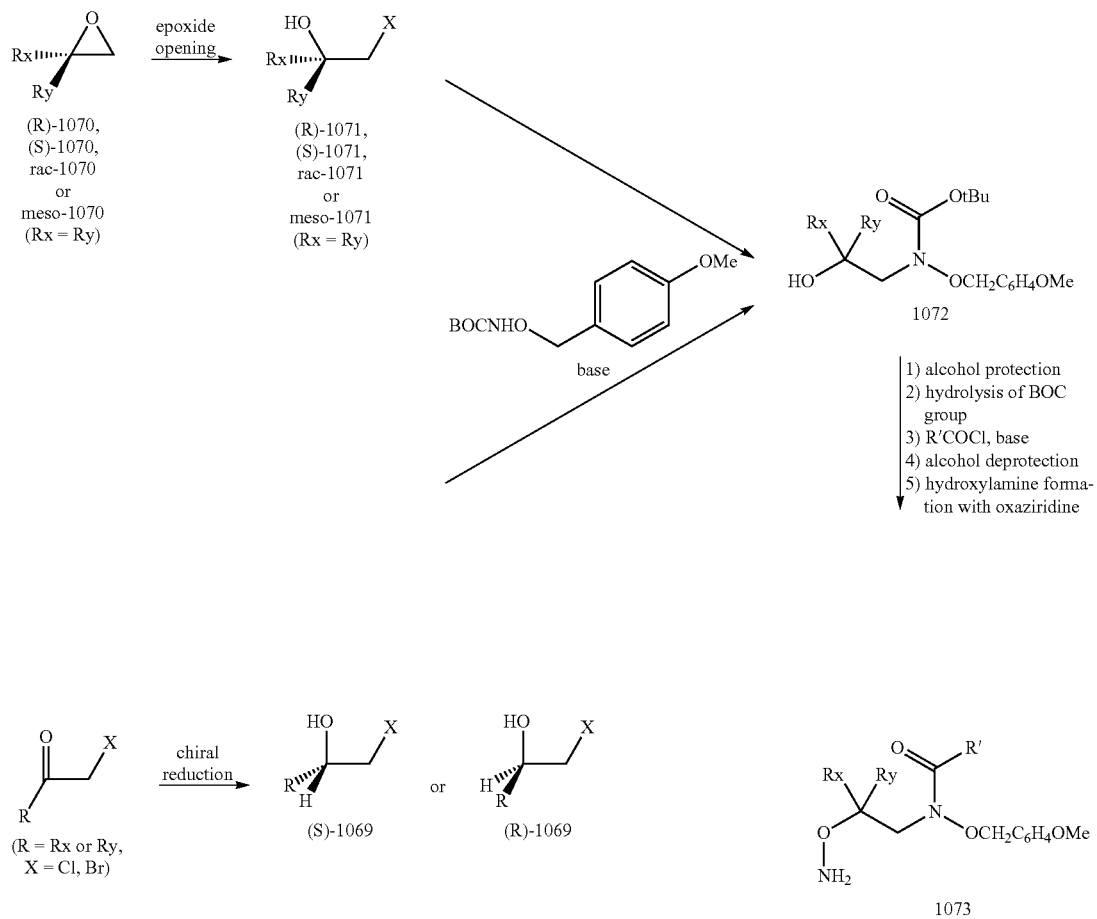

In the above scheme B-3-Ia, the epoxides meso-1070 may be made from a ketone with two identical residues Rx=Ry=R with trimethylsulfonium iodide and base. For the epoxides (R)-1070 and (S)-1070 the synthesis may start from a ketone with two different residues Rx≠Ry, using an asymmetric epoxide forming reaction such as the catalytic epoxidation developed by Aggarwal (Accounts of Chemical Research, 2004, 37, pp. 611ff.). The conversion of 1069 and 1071 to 1072 is analogous to the procedure of Bioorganic & Medicinal Chemistry Letters 1996, 6(17), 2077ff. In the conversion of 1072 to 1073, again the oxaziridine technology developed by Ellman can be employed to give the hydroxylamine (J. Org. Chem. 1999, 6528).

B-3-Ib) A second method, particular suited for hydroxylamines where R4 is C(Rx)(Ry)COOH, is outlined in the following scheme B-3-Ib. These hydroxylamines may be obtained from the corresponding alcohols R4-OH via Mitsunobu reaction conditions in presence of N-hydroxyphthalimide. The starting material R4-OH in turn may be obtained, as shown in the upper parts of scheme B-3-Ib, from an appropriately Rx,Ry-substituted ketone. To this ketone is added trimethylsilyl cyanide, either with or without a chiral catalyst, to obtain a silyl protected cyanohydrin 1074. The chiral thiourea catalyst indicated in scheme B-3-Ib, if used, and its conditions for use have been described in J. Am. Chem. Soc. 2005, 8964. The protected cyanohydrin is then reduced with LiAlH$_4$ to the corresponding aldehyde 1075 and then esterified to 1076. As an alternative to the Mitsunobu reaction using R4-OH, the hydroxyl group of N-hydroxyphthalimide can also be alkylated in presence of activated compounds R4-X (X can be halogens like Cl, Br, I, or activated sulfonate esters like mesylate, tosylate, triflate, etc; these are easily obtainable from the corresponding R4-OH). Formation of the desired hydroxylamine may be performed in presence of either hydrazine or methyl hydrazine, as shown in the lower part of scheme B-3-Ib, following the procedure described in J. Antibiotics, 2000, 1071.

Scheme B-3-Ib

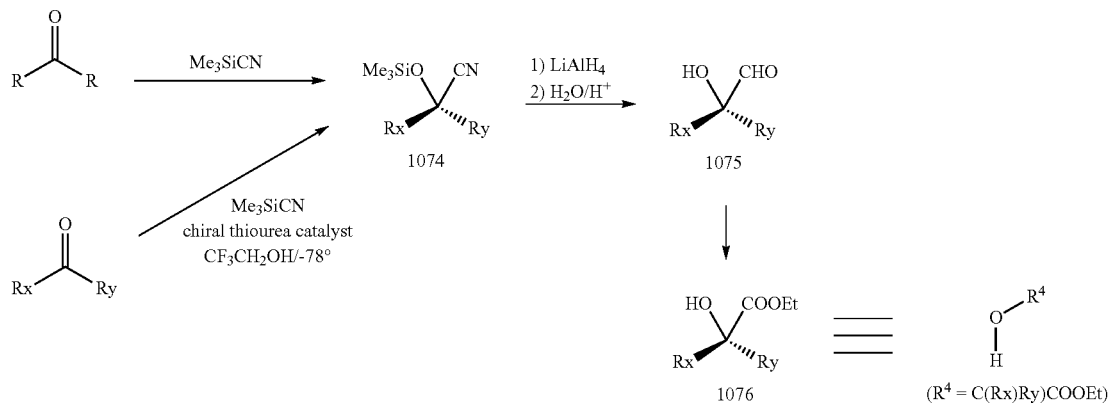

B-3-Ic) A further variant for the preparation of hydroxylamines where R4 is C(Rx)(Ry)COOH, may start with the epoxides 1070 shown in above scheme B-3-Ia. These epoxides may be opened, as is customary, with aqueous base to form a vicinal diol; in which the primary hydroxy group is then converted to the aldehyde and then to the ester as outlined in the above scheme B-3-Ib in the conversion of 1075 to 1076.

B-3-Id) For hydroxylamines where in R4Z is

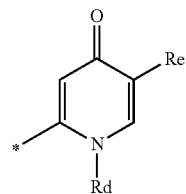

wherein Re and Rd are ORg (Rg being preferably selected from hydrogen, alkyl or optionally substituted benzyl for each Re and Rd), Rd is preferably hydrogen, alkyl, amino, monoalkylamino, optionally substituted benzyl, alkoxycarbonyl or ORg (wherein Rg is as for Re and Rd); and wherein Rx=Ry=H; the following synthetic scheme B-3-Id may be adopted:

Scheme B-3-Id

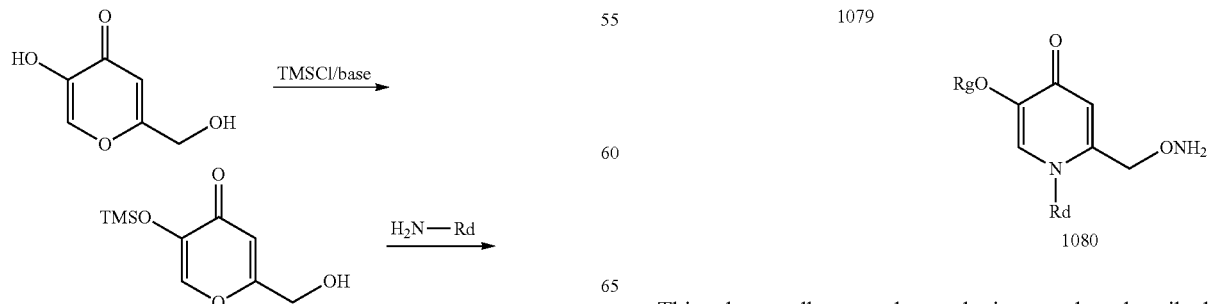

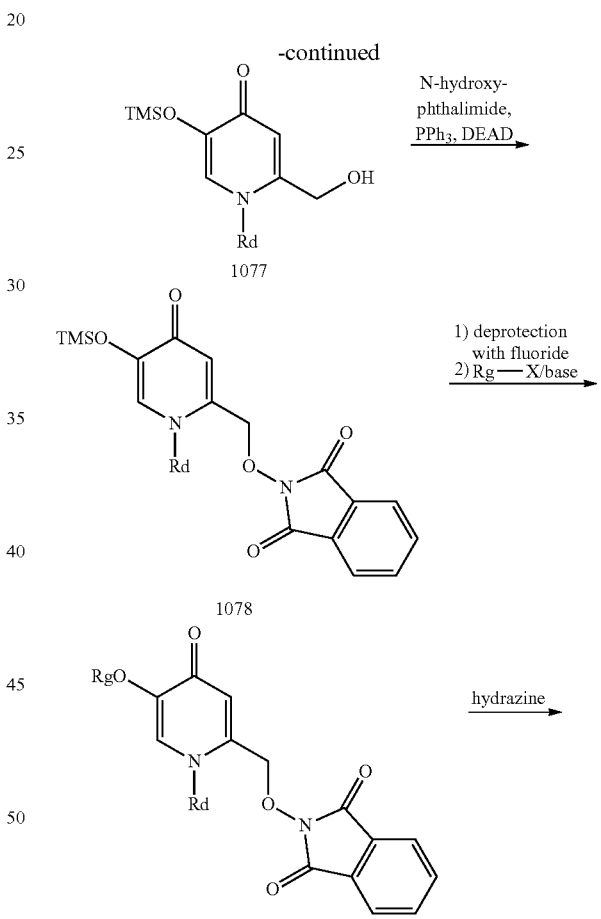

This scheme adheres to the synthetic procedure described in EP-A-0 251 299. The kojic acid used as the starting material is commercially available. In the conversion from the silyl-protected kojic acid to 1077 the reactands H₂N-Rd are amines, when Rd is hydrogen, alkyl or optionally substituted benzyl, they are hydrazines, when Rd is amino or monoalkylamino; they are carbamates, when Rd is alkoxycarbonyl; and when Rd is OR9, these reactands are hydroxylamines. In the conversion of 1078 to 1079, the reactands Rg-X are hydrogen halides, alkyl halides or benzyl halides, wherein X is preferably Br or I. These reactands Rg-X are known or easily made from the corresponding alcohols Rg-OH. In the above scheme, instead of trimethylsilyl other protecting groups could also be used, such as benzyl, diphenyl or trityl as reported in J. Antibiotics 1990, 1450.

B-3-Ie) For hydroxylamines where in R4 Z is

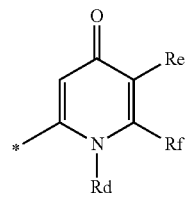

wherein Re and Rd are ORg (Rg being preferably selected from hydrogen, alkyl or optionally substituted benzyl for each Re and Rd), Rf is preferably alkoxycarbonyl or alkylaminocarbonyl; and wherein Rx=Ry=H; the following synthetic scheme B-3-Ie may be adopted:

The synthesis starts from kojic acid and is based on the known chemistry described in Biorg Med Chem Lett 2004, 3257; J. Med Chem 2002, 633; Bioorg Med. Chem. 2001 563 and J. Antibiotics 1990 1454. In the above scheme, the diphenylmethane protecting group in 1082 may subsequently be removed and, if desired, the free hydroxy group be reacted with an appropiate halide R—X, wherein R is alkyl or optionally substituted benzyl. These last steps are not shown in the above scheme.

B-3-If) For hydroxylamines where in R4 Z is

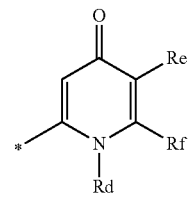

wherein Re and Rd are ORg (Rg being preferably selected from hydrogen, alkyl or optionally substituted benzyl for each Re and Rd), Rf is preferably alkyl; and wherein Rx=Ry=H; a gain starting from kojic acid and with adapted protecting group strategy, further examples of pyridone derivatives which can be prepared are according to following scheme B-3-If:

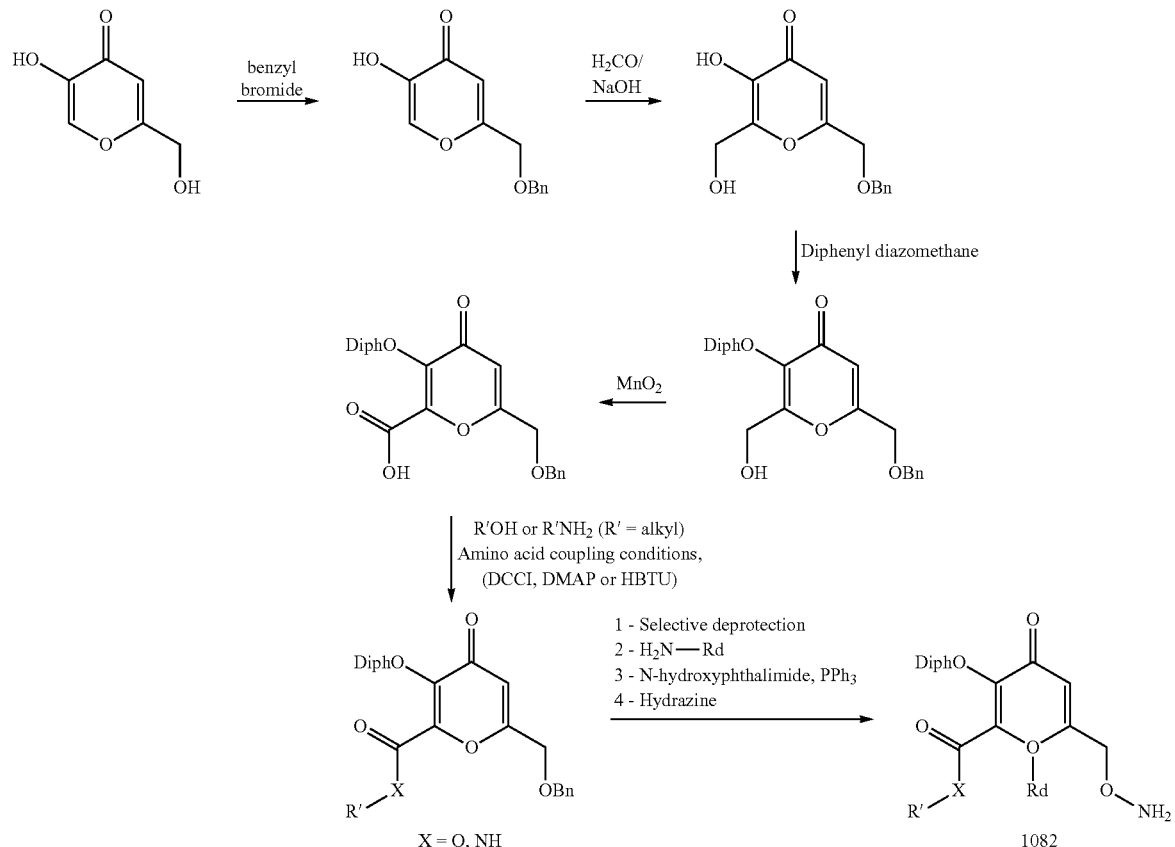

Scheme B-3-If

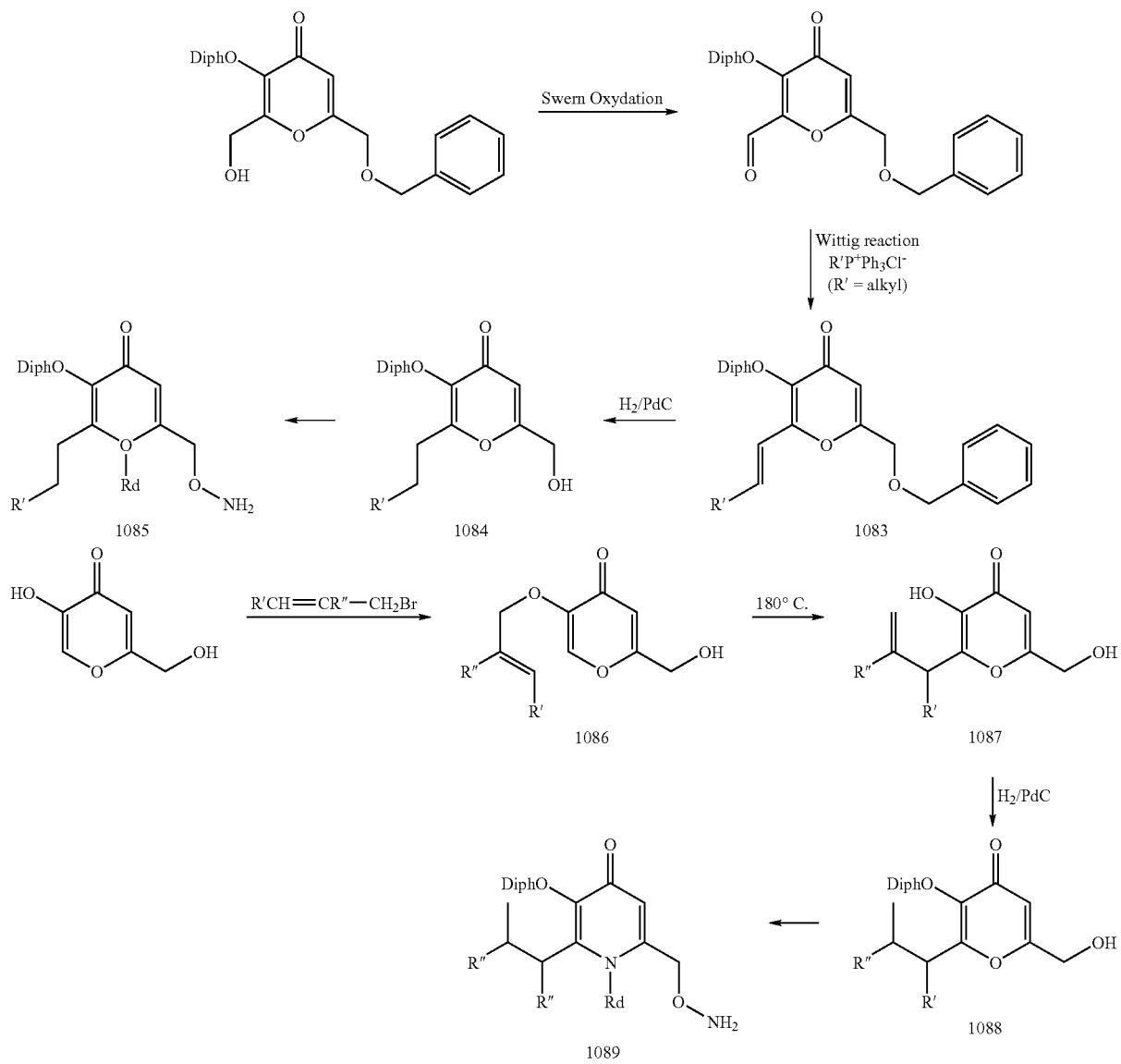

The upper part of scheme B-3-If is based on the possibility to run a Wittig reaction (J. Med. Chem. 2004, 6349) on the aldehyde obtained after Swern oxidation. The resulting product 1083 may be subjected to hydrogenolysis in presence of Pd/C similarly to the preparation of compound 10'j in J. Med. Chem. 2004, 6349. The resulting compound 1084 may then be treated as already outlined in above scheme 8 to obtain desired hydroxylamines 1085. The lower part of scheme B-3-If shows the preparation of hydroxylamines with linear or branched alkyl as Rf. In this part of scheme, R' and R" are preferably selected from alkyl (in particular methyl and ethyl) and hydrogen; more preferably one of R and R" is hydrogen, or both R' and R" are hydrogen. A thermal rearrangement of products 1086, obtainable by alkylation of the 4-hydroxyl group of koDic acid with appropiately R',R"-substituted allyl bromides (J. Am. Chem. Soc. 1956, 2816) leads to 6-substituted pyridones 1087. These may again be converted in the usual way to hydroxylamines 1089. In the above formed hydroxylamines 1085 and 1089 the diphenylmethane group may subsequently be removed and, if desired, the free hydroxy group be reacted with an appropiate halide R—X, wherein R is alkyl or optionally substituted benzyl. These last steps are not shown in the above scheme.

B-3-Ig) For hydroxylamines where in R4 Z is

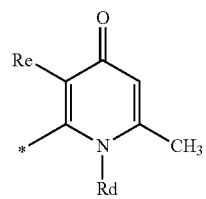

wherein Re is ORg (Rg being preferably selected from hydrogen, alkyl or optionally substituted benzyl), and Rd is preferably selected from hydrogen, alkyl, amino, monoalkylamino, optionally substituted benzyl or alkoxycarbonyl; and wherein Rx=Ry=H; a synthesis analogous to the scheme B-3-Ig shown below may be used. Details of the syntheses in the upper part of this scheme can be found in J. Med. Chem. 2004, 6349.

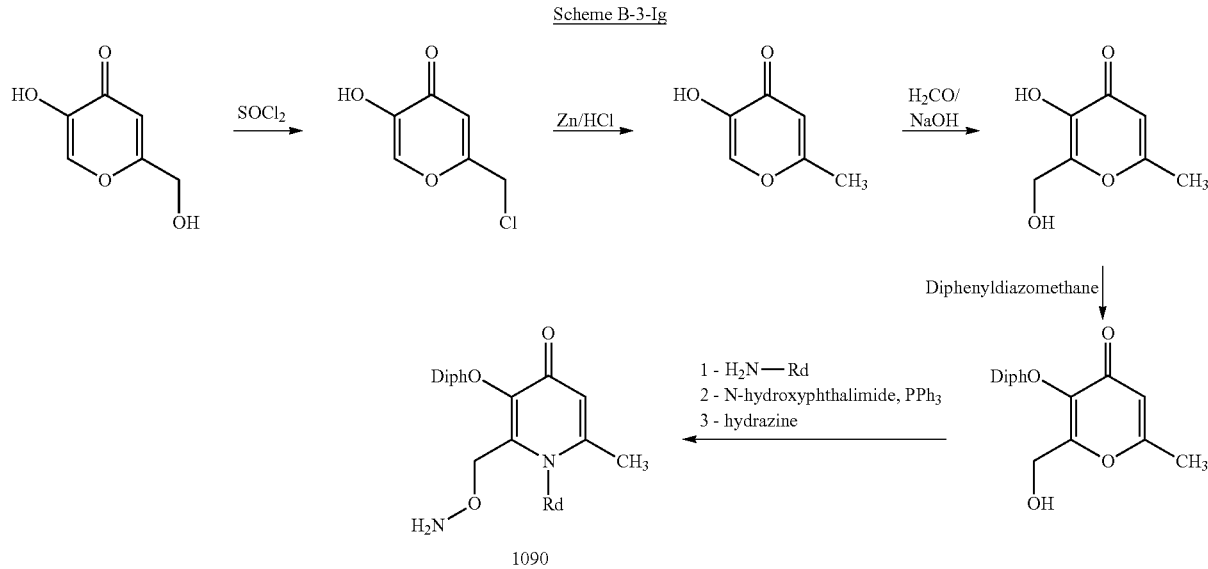

In the hydroxylamines 1090 obtained in above scheme B-3-Ig the diphenylmethane group may subsequently be removed and, if desired, the free hydroxy group be reacted with an appropriate halide R—X, wherein R is alkyl or optionally substituted benzyl. These last steps are not shown in the above scheme.

B-3-II) For hydroxylamines where z is

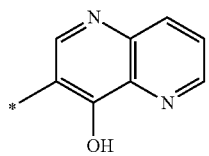

the following scheme B-3-II may be used. In this scheme, the naphthyridine hydroxylamine may be obtained from commercially available 4-hydroxy-1,5-naphthyridine-3-carboxylic ethyl ester after diphenyl protection of the hydroxyl group and reduction of ester group. Mitsunobu reaction in presence of N-hydroxyphthalimide and deprotection with hydrazine leads to the desired compound 1093.

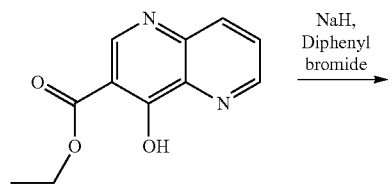

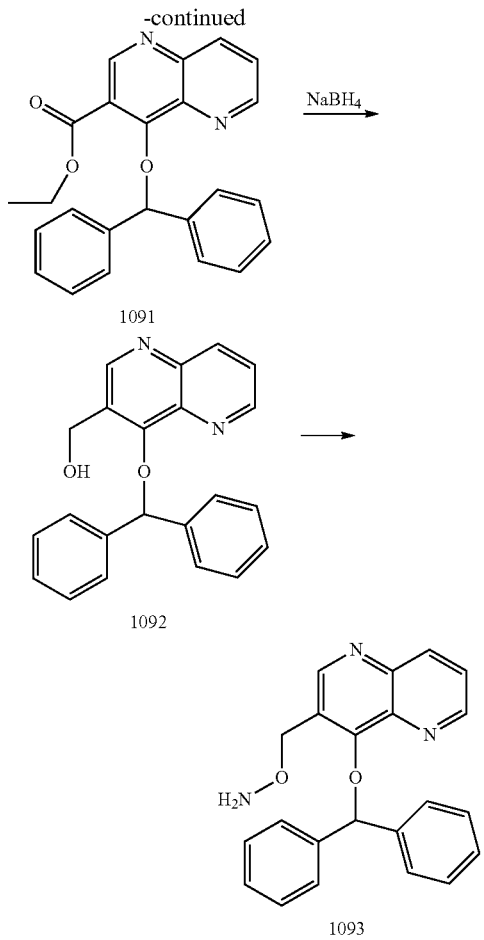

B-3-III) Further suited hydroxylamines are those where Z is selected from:

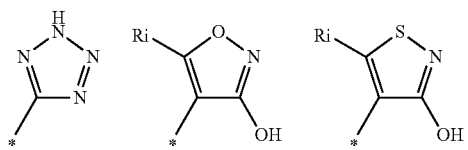

wherein Ri is as defined in claim 1. Those substituted 5-membered rings are known as bioisosteres (Curr. Med. Chem. 2004, 11, 945) of the carboxylic acid group. One particularly preferred hydroxylamine of this type, tetrazole methyl hydroxylamine 1094, may be obtained from commercially chloro methyl tetrazole with N-hydroxyphtalimide according to the method described in J. Antibiotics 2000, 1071 (scheme B-3-IIIa below).

Scheme B-3-IIIa

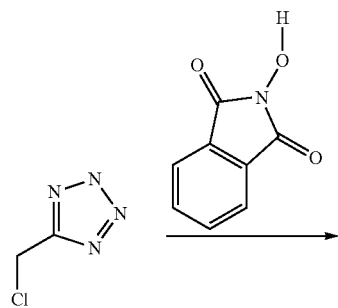

-continued

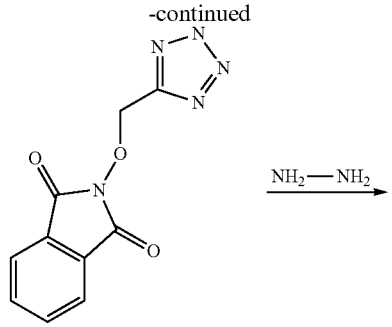

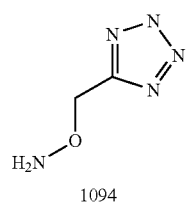

1094

Isoxazole analogs (J. Heterocyclic Chem. 1997, 345, J. Med. Chem. 1996, 183) or isothiazoles (J. Med. Chem. 1998, 930) are also known as bioisosteres of the carboxylic acid group and may be done in similar way as outlined in the scheme B-3-IIIb below based on the following literature (J. Chem. Soc., Perkin 1 1993, 2153; Synthesis 1996, 1177, Acta Chem. Scand. 1990, 96.

Scheme-B-3-IIIb

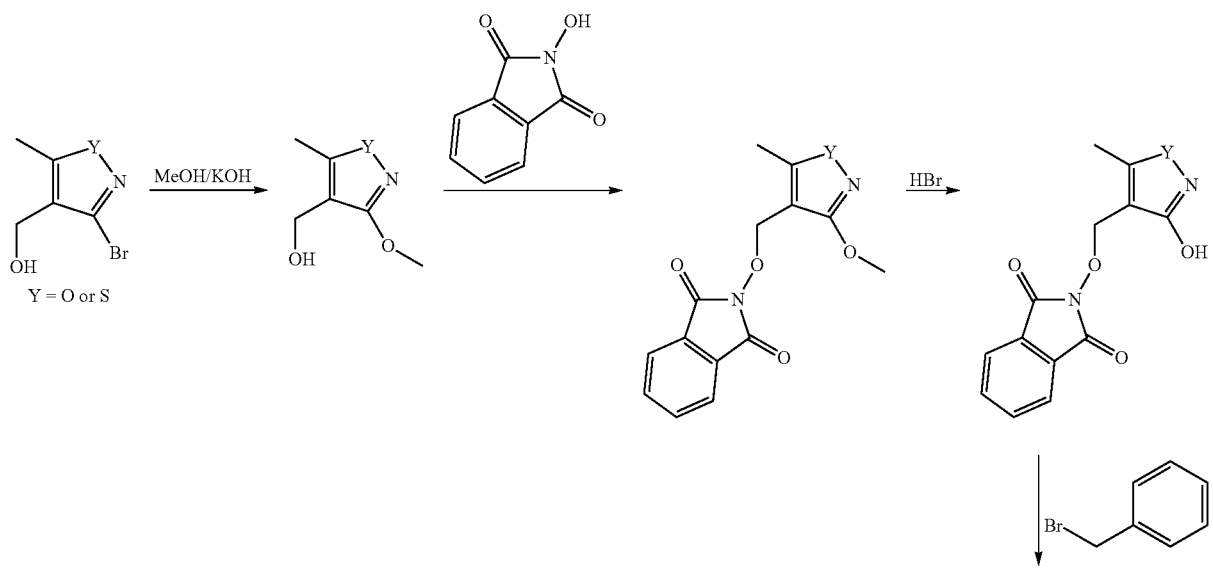

-continued

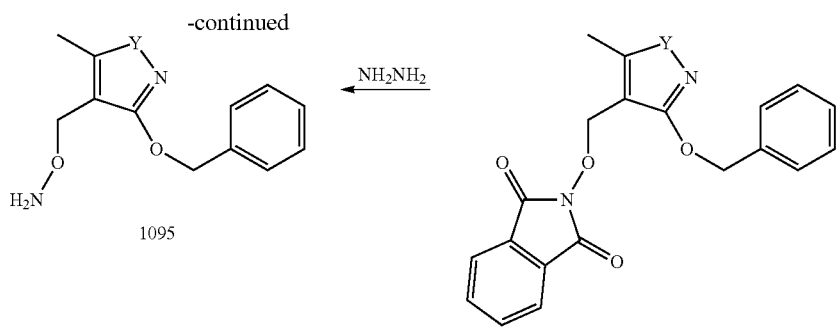

1095

In this scheme, the removal of the benzyl protecting group in the resulting hydroxylamine-containing isoxazoles and isothiazoles 1095 is not shown.

After formation of the ketoacid derivative A3, the condensation with O-substituted hydroxylamine (prepared or commercially available like O-methyl hydroxylamine) may be performed to lead to compounds of general formula A. The condensation of the hydroxylamines R4-ONH$_2$ with the keto acid derivatives A3 to form the compounds A may then follow the procedure described in J. Antibiotics 2000, 1071 and WO-A-02/22613.

B-4) As an alternative of preparing compounds A, the esters A1 may firstly be oxidised to form compounds A2 as shown in scheme 6, then reacted with hydroxylamine, followed by O-protection and ester hydrolysis, to lead to the intermediate C, which can be coupled to the azetidinone B. Substituents R4, can be introduced by alkylation. This alternate route is shown in the following scheme 9:

Scheme 9

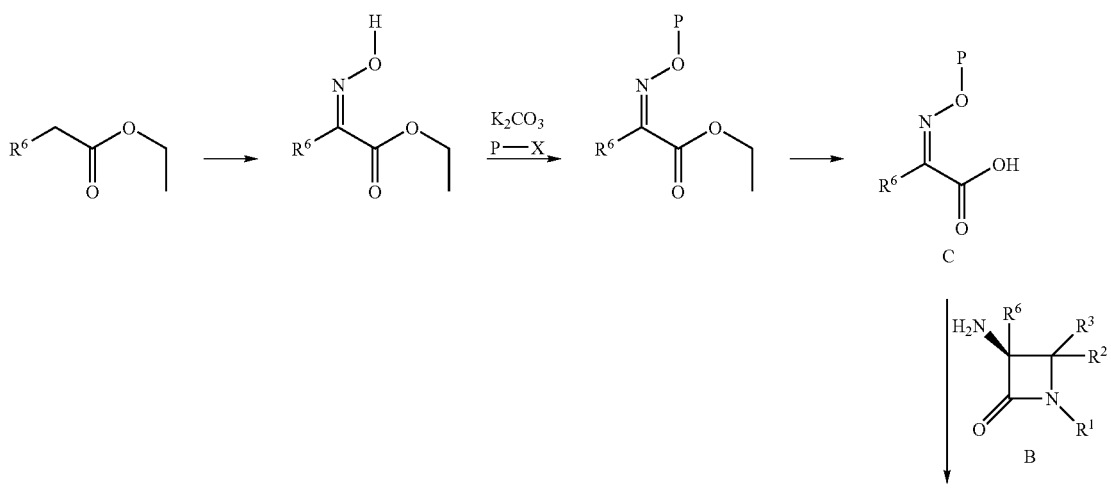

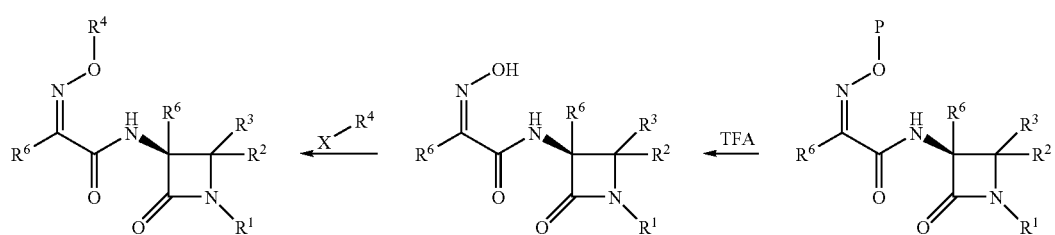

The compounds of formula II are compounds known from the above cited literature references (EP-A-0 508 284 and U.S. Pat. No. 6,566,355) or can be made in an analogous manner or can be made as described in the following scheme 10.

The intermediate compound D (J. Med. Chem. 1998, 3961 and EP-A-0 508 234) gives access to compounds of formula IIA, IIB or to IIC using different synthetic routes outlined in scheme 10.

Scheme 10

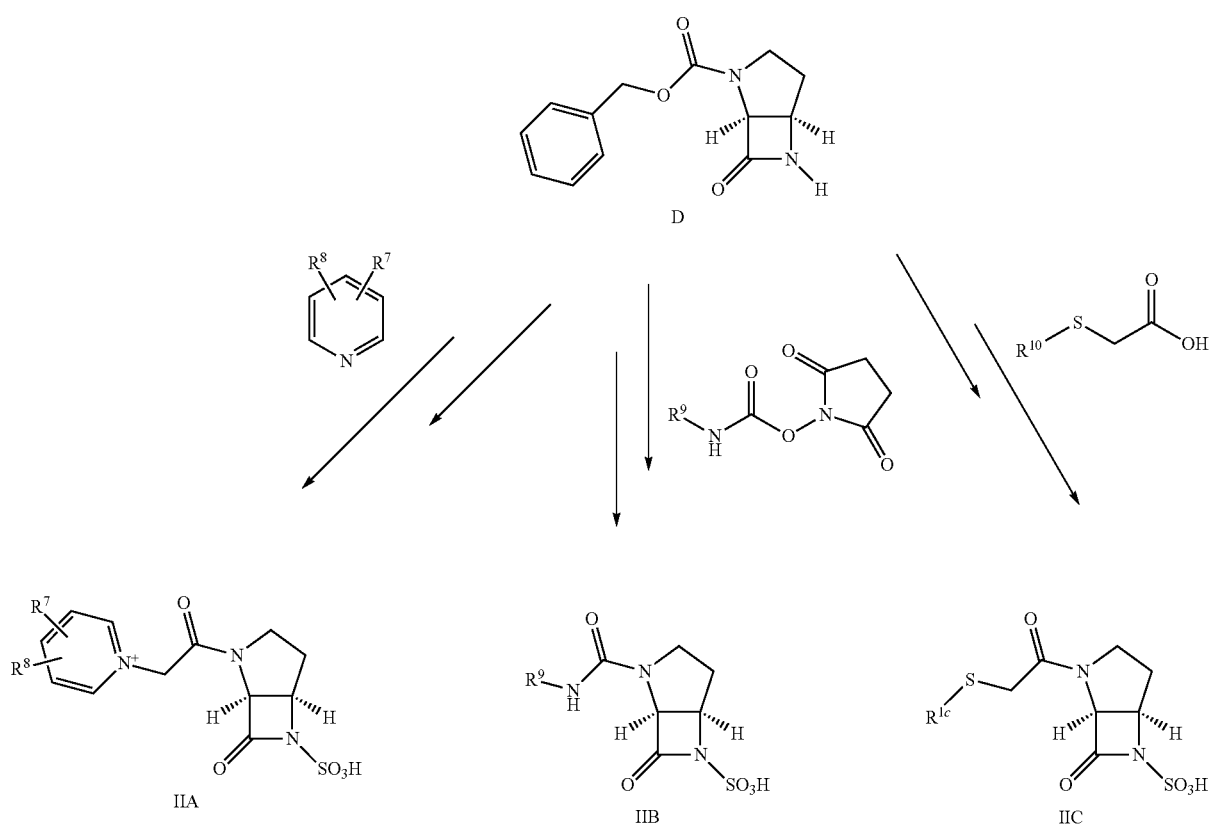

For the preparation of pyridinium carboxymethyl derivatives of formula IIA, two synthetic routes are possible (scheme 11):

First pathway: Compound F, prepared from compound D in presence of bromo acetyl bromide according to the procedures described in J. Med. Chem. 1998, 3961 and EP-A-0 508 234, may be sulfonated (J. Org. Chem. 1982, 5160). Pyridine derivatives, condensed at room temperature in dimethylformamide, are either commercially available or synthesized according to known literature procedures.

Second pathway: Compound D may be first hydrogenated in presence of $BOC_2O$ to afford the intermediate G (Tetrahedron Lett. 1988, 2983). Then sulfonation of compound G followed by removal of the BOC protecting group generates compound H (J. Med. Chem. 1998, 3961 and J. Org. Chem. 1982, 5160).

At that stage the pyridinium carboxymethyl derivatives (prepared by analogy according to the procedures described in Synthesis 2000, 1733 or J. Chem. Soc, Perkin Trans. I 1977, 1692) may be introduced to generate compounds IIA.

Scheme 11

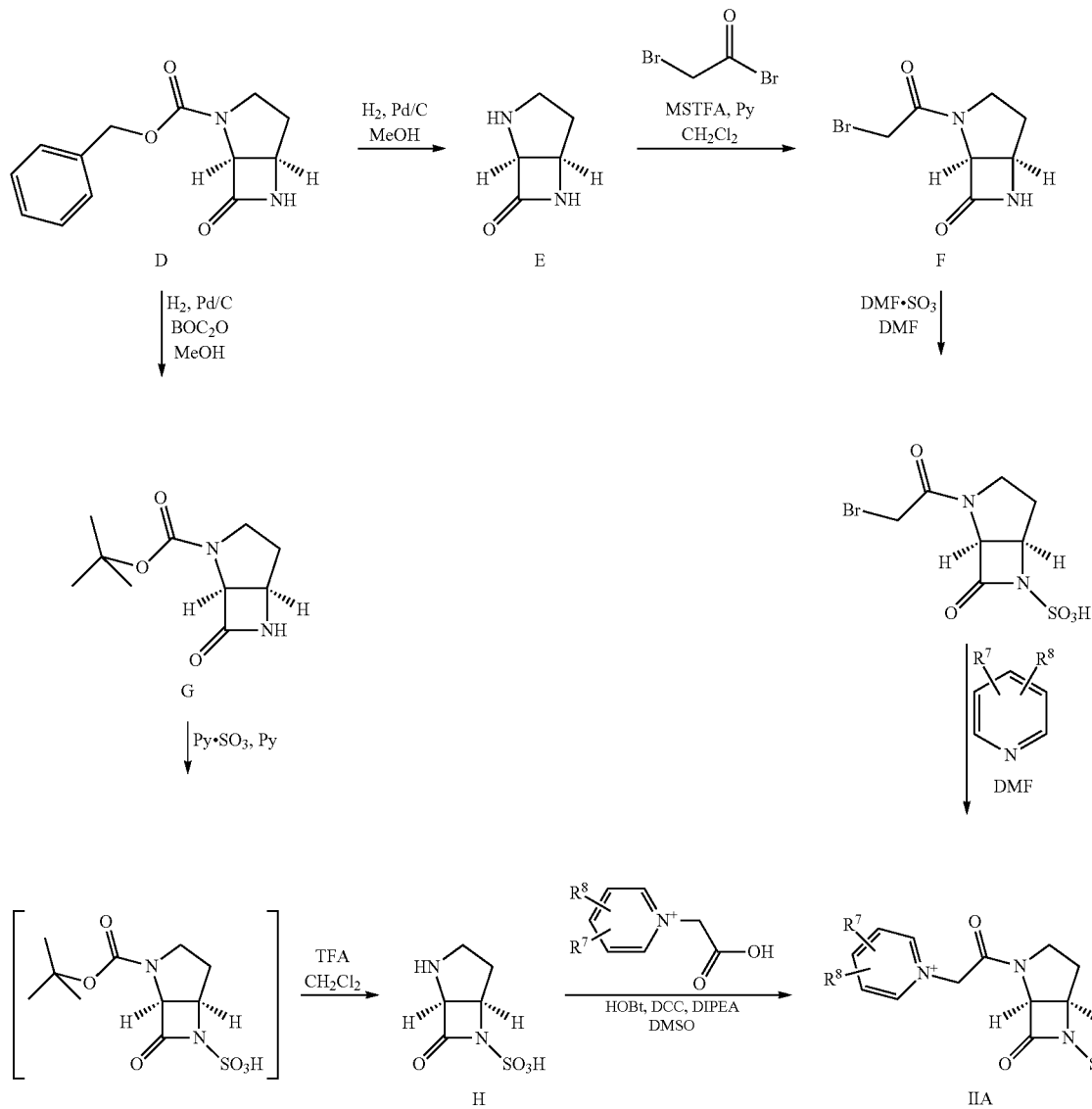

The compounds of formula IIB may be obtained from compound H and succinimidyl derivatives according to the following scheme 12:

Scheme 12

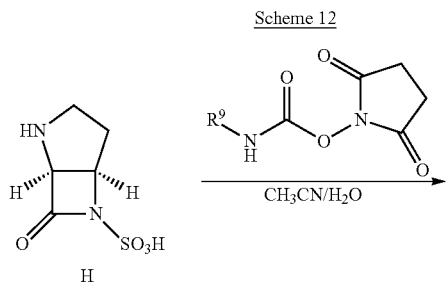

Compound H may be prepared as previously described in scheme 11. Then the succinimidyl derivatives may be synthesized and introduced according to the procedures described in J. Med. Chem. 1998, 3961.

Compounds of formula IIC may be obtained either from compound E or compound H according to the following scheme 13:

Scheme 13

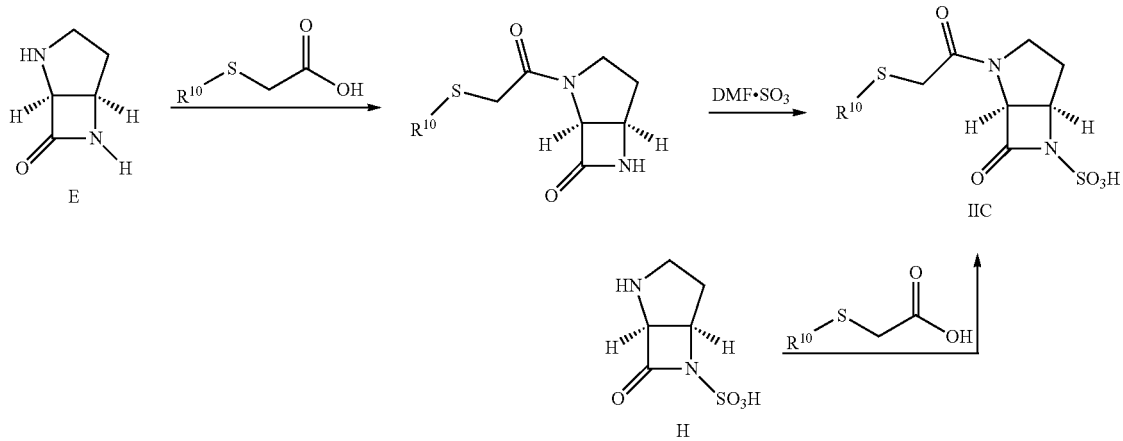

The compounds IIC may be synthesized via two different routes:
- either from compound E by first coupling with the thioacetic acid derivatives, followed by a sulfonation step (J. Med. Chem. 1998, 3961),
- or directly from compound H (see scheme 11) and thioacetic acid derivatives.

The preparation of sodium salt of compound of formula I and II can be performed either with the procedures described in WO-A-02/22613, U.S. Pat. No. 6,566,355, J. Med. Chem. 1998, 3961 or in J. Antibiotics, 1985, 346.

In the above descriptions, the reactants are reacted together with a suitable solvent at elevated or low temperatures for sufficient time to allow the reaction to proceed to completion. The reaction conditions will depend upon the nature and reactivity of the reactants. Wherever a base is used in a reaction, they are selected from e.g. triethylamine, tributylamine, trioctylamine, pyridine, 4-dimethylaminopyridine, diisopropylamine, 1,5-diazabicyclo[4,3,0]non-5-ene, 1,8-diazabicyclo[5,4,0]undec-7-ene, sodium carbonate, sodium dicarbonate, potassium carbonate, potassium bicarbonate or cesium carbonate.

The deprotection of functional groups may be carried out either by hydrogenation or hydrolysis with appropriate acids such as hydrochloric acid, formic acid, trifluoroacetic acid, acetic acid or p-toluenesulfonic acid; in solvents such as methanol, ethanol, propanol, ethyl acetate, acetonitrile, methylene chloride or ethylene chloride. The hydrogenation is usually carried out in the presence of a metal catalyst, such as Pd, Pt or Rh under normal to high pressure.

The solvents of choice for the reaction are selected based upon the reactants used and from solvents such as benzene, toluene, acetonitrile, tetrahydrofurane, ethanol, methanol, chloroform, ethyl acetate, methylene chloride, dimethyl formamide, dimethyl sulfoxide, hexamethyl phosphoric triamide or the like. Solvents mixtures may also be used.

Reaction temperatures would generally range from between −70° C. to 150° C. The preferred molar ratio of the reactants is 1:1 to 1:5. The reaction time range from 0.5 to 72 hours, depending on the reactants.

The compounds of formula I, Ia and Ib and their pharmaceutically compatible salts can be used in accordance with the invention in the control or prevention of illness in mammals, human and non-human, especially in combination with β-lactamase inhibitors.

Thereby, the compound of formula I or pharmaceutically compatible salts thereof with bases can be administered before, simultaneously with or after the administration or intake of one or more β-lactamase inhibitors of formula II-XIII. The products in accordance with the invention can be administered in the form of pharmaceutical compositions containing the combination of a compound of formula I or a pharmaceutically compatible salt thereof with a base, and one or more β-lactamase inhibitors of formula II-XIII; alternatively, they may also be administered separately from the β-lactamase inhibitors, simultaneously or sequentially, in which case the combination according to the invention may be present as a kit-of-parts. Articles with such pharmaceutical combinations are also an object of the present invention.

The compounds of formula I are active against a variety of bacterial organisms. They are active against aerobic Gram-negative bacteria that do not produce β-lactamases, including Enterobacteriaceae, for example *Escherichia coli, Enterobacter cloacae, Enterobacter aerogenes, Citrobacter freundii, Klebsiella pneumoniae, Klebsiella oxytoca, Proteus vulgaris, Providencia rettgeri; Pseudomonas* for example *P. aeruginosa; Acinetobacter* for example *A. baumannii; Burkholderia*, for example *B. cepacea; Stenotrophomonas* for example *S. maltophilia*. Combinations of compounds of formula I and formula II are active against strains of the above organisms that do produce β-lactamases and this activity can be increased by additionally combining compounds of formula III-XIII with the combination comprising compounds of formulae I and II.

Formulations

The pharmaceutical compositions and articles (kits-of-parts) according to the present invention are administered by any route, preferably in the form of a pharmaceutical composition, or kit-of-parts of individual compositions, adapted to such a route. Dosage and route of administration should be determined by susceptibility of the causative organisms, severity and site of infection, and the condition of the patient. The preferred types of pharmaceutical compositions are, for example, administered intravenously or by intramuscular injection.

Formulations for parenteral administration can be in the form of aqueous isotonic sterile injection solutions or suspensions. These solutions or suspensions can be prepared from sterile powders, granules or lyophilizates. The compounds can be dissolved in sterile water or in various sterile buffers that may contain sodium chloride, polyethylene glycol, propylene glycol, ethanol, sucrose, glucose, arginine, lysine, or lactic acid. The dry compositions can contain from 0.1% to 99% by weight, preferably 10%-60% by weight, of each of active ingredients. If the compositions contain dosage units, each unit preferably contains from 50 mg to 4 g of each active substance.

The ratio of β-lactam antibiotic (compounds of formula I or pharmaceutically compatible salts thereof with a base) and β-lactamase inhibitors (compounds of formula II and formula III-XIII, or pharmaceutically compatible salts thereof with a base) can also vary within wide limits and will be fitted to the individual requirements in each particular case. In general, a ratio of between 1 part of antibiotic of general formula I to 5 parts of any one β-lactamase inhibitor of general formula II or III-XIII and 20 parts of antibiotic of general formula I to 1 part of any one β-lactamase inhibitor of general formula II or III-XIII should be appropriate.

The dosage of the compound of formula I and of the pharmaceutically compatible salts thereof with bases can vary within wide limits and will be fitted in each particular case to the individual requirements and to the β-lactamase producing pathogen to be controlled. In general, a dosage of about 0.1 to about 2 g of antibiotic administered one to four times over a 24 hours period should be appropriate.

The present invention is further illustrated by the following non-limiting examples.

Example 1

(3S,4S)-3-{(2Z)-2-(2-amino(1,3-thiazol-4-yl))-3-[(5-hydroxy-1-methyl-4-oxo(2-hydropyridyl))methoxy]-3-azaprop-2-enoylamino}-4-methyl-2-oxoazetidinesulfonic acid (6)

Preparation of 5-(diphenylmethoxy)-2-(hydroxymethyl)-1-methylhydropyridin-4-one 5-(Diphenylmethoxy)-2-(hydroxymethyl)pyran-4-one (J. Antibiotics 1990, 189) (5.0 g, 16.22 mmol) and methyl amine (80.6 g, 1.04 mol) were stirred at room temperature overnight in presence of methanol (1 mL). The precipitate observed was filtered off and the mother liquor was extracted 3 times with ethyl acetate. The organic phases were dried and the solvent evaporated. The total amount of collected product was 2.1 g.

1H-NMR (DMSO-d6) d: 3.49 (s, 3H), 4.29 (s, 2H), 6.22 (s, 1H), 6.74 (s, 1H), 7.20-7.60 (m, 1H).

Preparation of 2-{[5-(diphenylmethoxy)-1-methyl-4-oxo-2-hydropyridyl]methoxy}benzo[c]azoline-1,3-dione In THF (10.0 mL), containing triphenylphosphine (0.470 g, 1.79 mmol) and N-hydroxyphthalimide (0.293 g, 1.79 mmol) was added 5-(diphenylmethoxy)-2-(hydroxymethyl)-1-methylhydropyridin-4-one (0.240 g, 0.75 mmol). After cooling the solution at 0° C., diethyl-azodicarboxylate (0.312 g, 1.79 mmol) was added dropwise and stirred for 30 min at this temperature. The solution was then warmed up to room temperature and stirred overnight. A suspension was observed, filtered off and washed to give 210 mg of the desired compound.

1H-NMR (DMSO-d6) d: 3.78 (s, 3H), 5.08 (s, 2H), 6.29 (s, 1H), 6.74 (s, 1H), 7.20-7.50 (m, 10H), 7.69 (s, 1H), 7.80-7.90 (m, 4H),

Preparation of 2-[(aminooxy)methyl]-5-(diphenylmethoxy)-1-methylhydro pyridin-4-one Hydrazine hydrate (0.023 mL, 0.47 mmol) was added to ethanol (10 mL) already containing 2-{[5-(diphenylmethoxy)-1-methyl-4-oxo-2-hydropyridyl]methoxy}benzo [c]azoline-1,3-dione (0.200 g, 043 mmol). The resulting solution was refluxed for 2 hours. After cooling at room temperature the precipitate was collected and the ethanol was evaporated. The resulting residue was triturated in ethyl acetate to give 130 mg of the expected compound.

1H-NMR (DMSO-d6) d: 3.51 (s, 3H), 4.43 (s, 2H), 6.21 (s, 1H), 6.29 (br s, 2H), 6.74 (s, 1H), 7.20-7.50 (m, 10H), 7.56 (s, 1H).

Preparation of (2Z)-3-{[5-(diphenylmethoxy)-1-methyl-4-oxo(2-hydropyridyl)]methoxy}-2-{2-[(triphenylmethyl)amino](1,3-thiazol-4-yl)}-3-azaprop-2-enoic acid In a mixture of ethanol (5 mL)/chloroform (3 mL), 2-[(aminooxy)methyl]-5-(diphenylmethoxy)-1-methylhydropyridin-4-one (0.076 g, 0.23 mmol) and 2-oxo-2-{2-[(triphenylmethyl)amino](1,3-thiazol-4-yl)}acetic acid (0.085 g, 0.21 mmol) were stirred at room temperature for 12 hours. The solvents were evaporated and ethyl acetate was added to the residue. The resulting suspension was filtered off to afford 77 mg of the desired compound.

1H-NMR (DMSO-d6) d: 3.49 (s, 3H), 5.00 (s, 2H), 6.24 (s, 1H), 6.72 (s, 2H), 6.83 (s, 1H), 7.15-7.50 (m, 25H), 7.57 (s, 1H), 8.85 (s, 1H).

Preparation of (3S,4S)-3-((2Z)-3-{[5-(diphenylmethoxy)-1-methyl-4-oxo(2-hydropyridyl)]methoxy}-2-{2-[(triphenylmethyl)amino](1,3-thiazol-4-yl)}-3-azaprop-2-enoylamino)-4-methyl-2-oxoazetidinesulfonic acid (2Z)-3-{([5-(diphenylmethoxy)-1-methyl-4-oxo(2-hydropyridyl)]methoxy}-2-{2-[(triphenyl methyl)amino](1,3-thiazol-4-yl)}-3-azaprop-2-enoic acid (0.380 g, 0.52 mmol), dicyclohexylcarbodiimide (0.160 g, 0.78 mmol) and 1-hydroxy-7-azabenzotriazole (0.106 g, 0.78 mmol) were stirred at room temperature for 3 hours. Then (3S,4S)-3-amino-4-methyl-2-oxoazetidinesulfonic acid (0.103 g, 1.04 mmol) and a catalytic amount of triethylamine were added to the previous solution which was stirred for 16 hours at room temperature. The solvent was evaporated in vacuo and the residue was purified by column chromatography (silica gel, eluent; dichloromethane and methanol, 95/5, v/v). 100 mg of desired compound was obtained.

1H-NMR (DMSO-d6) d: 1.35 (d, 3H, J=6.0 Hz), 3.55-3.60 (m, 1H) 3.83 (s, 3H), 4.34 (dd, 1H, J=2.5, 7.7 Hz), 5.21 (s, 2H), 6.75 (m, 1H), 6.77 (s, 1H), 7.00 (s br, 1H), 7.15-7.60 (m, 26H), 8.39 (s br, 1H) 8.83 (s, 1H), 9.33 (d, 1H, J=7.7 Hz).

(3S,4S)-3-{(2Z)-2-(2-amino(1,3-thiazol-4-yl))-3-[(5-hydroxy-1-methyl-4-oxo(2-hydropyridyl))methoxy]-3-azaprop-2-enoylamino}-4-methyl-2-oxoazetidinesulfonic acid (6)

(3S,4S)-3-((2Z)-3-{[5-(diphenylmethoxy)-1-methyl-4-oxo(2-hydropyridyl)]methoxy}-2-{2-[(triphenylmethyl)amino](1,3-thiazol-4-yl)}-3-azaprop-2-enoylamino)-4-methyl-2-oxoazetidinesulfonic acid (0.076 g, 0.08 mmol) was dissolved in dichloromethane (3 mL). Triethylsilane (0.021 mL, 0.25 mmol) was added at −10° C. and trifluoroacetic acid (0.327 mL, 4.25 mmol) was added dropwise and stirred for 1 h at the same temperature. The solution reacted at room temperature for 2 hours. Then dichloromethane was evaporated in vacuo and the residue was purified by preparative HPLC to give 35 mg of the desired compound.

Example 2

(3S,4S)-3-{(2Z)-2-(2-amino(1,3-thiazol-4-yl))-3-[(1,5-dihydroxy-4-oxo(2-hydropyridyl))methoxy]-3-azaprop-2-enoylamino}-4-methyl-2-oxoazetidinyl hydroxysulfonate (12)

The titled compound was prepared following scheme 1. (2Z)-3-{[1,5-bis(diphenylmethoxy)-4-oxo(2-hydropyridyl)]methoxy}-2-{2-[(triphenylmethyl)amino](1,3-thiazol-4-yl)}-3-azaprop-2-enoic acid was prepared according to the procedures described in J. Antibiotics, 1990, 1450 and WO-A-02/22613 and (3S,4S)-3-amino-4-methyl-2-oxoazetidinyl hydroxysulfonate was prepared according to the procedures described in J. Am. Chem. Soc, 1982, 6053 and J. Antibiotics, 1985, 1536.

Final assembly and deprotection steps were done similarly according to the method described for the example 1.

Example 3

(3S,4S)-3-{(2Z)-2-(4-aminopyrimidin-2-yl)-3-[(1,5-dihydroxy-4-oxo(2-hydropyridyl))methoxy]-3-azaprop-2-enoylamino}-4-methyl-2-oxoazetidinesulfonic acid (21)

The titled compound was prepared following scheme 8. (2Z)-3-{[1,5-bis(diphenylmethoxy)-4-oxo(2-hydropyridyl)]methoxy}-2-{4-[(triphenylmethyl)amino]pyrimidin-2-yl}-3-azaprop-2-enoic acid was prepared according to the procedures described in J. Antibiotics, 1984, 546 and (3S,4S)-3-amino-4-methyl-2-oxoazetidinesulfonic acid was prepared according to the procedures described in J. Org. Chem. 1980, 410.

Final assembly and deprotection steps were done similarly according to the method described for the example 1.

Example 4

2-((3S,4S)-3-{(2Z)-2-(2-amino(1,3-thiazol-4-yl))-3-[(1,5-dihydroxy-4-oxo(2-hydropyridyl))methoxy]-3-azaprop-2-enoylamino}-4-methyl-2-oxoazetidinyloxy)acetic acid (22)

The title compound was prepared following scheme 1. (2Z)-3-{[1,5-Bis(diphenylmethoxy)-4-oxo(2-hydropyridyl)]methoxy}-2-{2-[(triphenylmethyl)amino](1,3-thiazol-4-yl)}-3-azaprop-2-enoic acid was prepared according to the procedures described in J. Antibiotics, 1990, 1450 and WO-A-02/22613 and 2-((3S,4S)-3-amino-4-methyl-2-oxoazetidinyloxy)acetic acid was prepared according to the procedure described in J. Med. Chem. 1985, 1447 and J. Antibiotics, 1985, 813.

Final assembly and deprotection steps were done similarly according to the method described for the example 1.

Example 5

(2S)-2-((3S,4S)-3-{(2Z)-2-(2-amino(1,3-thiazol-4-yl))-3-[(1,5-dihydroxy-4-oxo(2-hydropyridyl))methoxy]-3-azaprop-2-enoylamino}-4-methyl-2-oxoazetidinyloxy)propanoic acid (23)

The titled compound was prepared following scheme 1. (2Z)-3-{[1,5-bis(diphenylmethoxy)-4-oxo(2-hydropyridyl)]methoxy}-2-{2-[(triphenylmethyl)amino](1,3-thiazol-4-yl)}-3-azaprop-2-enoic acid was prepared according to the procedures described in J. Antibiotics, 1990, 1450 and WO-A-02/22613 and (2S)-2-((3S,4S)-3-amino-4-methyl-2-oxoazetidinyloxy)propanoic acid was prepared according to the procedure described in J. Med. Chem. 1985, 1447 and J. Antibiotics, 1985, 813.

Final assembly and deprotection steps were done similarly according to the method described for the example 1.

Example 6

(3S)-3-{(2Z)-2-(2-amino(1,3-thiazol-4-yl))-3-[(1,5-dihydroxy-4-oxo(2-hydropyridyl))methoxy]-3-azaprop-2-enoylamino}-4,4-dimethyl-2-oxoazetidinyl hydroxysulfonate (26)

The title compound was prepared following scheme 1. (2Z)-3-{[1,5-bis(diphenylmethoxy)-4-oxo(2-hydropyridyl)]methoxy}-2-{2-[(triphenylmethyl)amino](1,3-thiazol-4-yl)}-3-azaprop-2-enoic acid was prepared according to the procedures described in J. Antibiotics, 1990, 43, 1450 and WO-A-02/22613 and (3S)-3-amino-4,4-dimethyl-2-oxoazetidinyl hydroxysulfonate was prepared according to the procedure described in J. Org. Chem. 2003, 177 and Tetrahedron Lett., 1986, 2789.

Final assembly and deprotection steps were done similarly according to the method described for the example 1.

Example 7

(3S,4S)-3-{(2Z)-2-(2-amino-5-chloro(1,3-thiazol-4-yl))-3-[(1,5-dihydroxy-4-oxo(2-hydropyridyl))methoxy]-3-azaprop-2-enoylamino}-4-methyl-2-oxoazetidinyl hydroxysulfonate (29)

The titled compound was prepared following scheme 1. (2Z)-3-{[1,5-bis(diphenylmethoxy)-4-oxo(2-hydropyridyl)]methoxy}-2-{5-chloro-2-[(triphenylmethyl)amino](1,3-thiazol-4-yl)}-3-azaprop-2-enoic acid was prepared according to the procedures described in J. Antibiotics, 1990, 1450 and WO-A-02/22613 and (3S,4S)-3-amino-4-methyl-2-oxoazetidinyl hydroxysulfonate was prepared according to the procedure described in J. Am. Chem. Soc, 1982, 6053 and J. Antibiotics, 1985, 1536.

Final assembly and deprotection steps were done similarly according to the method described for the example 1.

Example 8

(3S,4S)-3-{2-(2-amino(1,3-thiazol-4-yl))-3-[(5-hydroxy-1-methoxy-4-oxo(2-hydropyridyl))methoxy]-3-azaprop-2-enoylamino}-4-methyl-2-oxoazetidinesulfonic acid (5)

The title compound was prepared following scheme 1.
The alcohol derivative 5-(diphenylmethoxy)-2-(hydroxymethyl)-1-methoxyhydropyridin-4-one was obtained according to the following procedure;

5-(diphenylmethoxy)-2-(hydroxymethyl)-1-methoxyhydropyridin-4-one

To a solution of DMF (20 mL) containing 5-(diphenylmethoxy)-1-hydroxy-2-(hydroxymethyl)hydropyridin-4-one (J. Antibiotics 1990, 1450) (2.0 g, 6.19 mmol) at 0° C. was first added potassium tert-butoxyde (0.971 g, 8.66 mmol)

and then iodo methane (4.23 g, 8.66 mol). The resulting mixture was stirred for 30 min at 0° C. and then 2 h at room temperature. Then ethyl acetate (20 mL) and water (50 mL) was added. The observed precipitate was filtered off and the washed with additional ethyl acetate. The total of amount of collected product was 1.4 g.

1H-NMR (DMSO-d6) d: 3.87 (s, 3H), 4.38 (d, 2H, J=5.8 Hz), 5.55 (t, 1H, J=5.8 Hz) 6.13 (s, 1H), 6.69 (s, 1H), 7.20-7.50 (m, 10H), 7.88 (s, 1H).

The compound of formula A (2Z)-3-{[5-(diphenyl-methoxy)-1-methoxy-4-oxo(2-hydropyridyl)]methoxy}-2-{2-[(triphenylmethyl)amino](1,3-thiazol-4-yl)}-3-azaprop-2-enoic acid was prepared according to the procedures described in example 1 and (3S,4S)-3-amino-4-methyl-2-oxoazetidinesulfonic acid was prepared according to the procedures described in J. Org. Chem. 1980, 410.

Final assembly and deprotection steps were done similarly according to the method described for the example 1.

Example 9

(3S,4S)-3-{(2Z)-2-(2-amino(1,3-thiazol-4-yl))-3-[(1-hydroxy-5-methoxy-4-oxo(2-hydropyridyl))methoxy]-3-azaprop-2-enoylamino}-4-methyl-2-oxoazetidinesulfonic acid (7)

The titled compound was prepared following scheme 1.
2-(hydroxymethyl)-5-methoxypyran-4-one was prepared from kojic acid according to the procedure described in J. Org. Chem. 1950, 221

Then the preparation of the compound of formula A (2Z)-3-{[1-(diphenylmethoxy)-5-methoxy-4-oxo(2-hydropyridyl)]methoxy}-2-{2-[(triphenylmethyl)amino](1,3-thiazol-4-yl)}-3-azaprop-2-enoic acid was prepared according to the procedures described in example 1 and (3S,4S)-3-amino-4-methyl-2-oxoazetidinesulfonic acid was prepared according to the procedures described in J. Org. Chem. 1980, 410.

Final assembly and deprotection steps were done similarly according to the method described for the example 1.

Example 10

(3S,4S)-3-{(2Z)-2-(2-amino(1,3-thiazol-4-yl))-3-[2-(hydroxyacetylamino) ethoxy]-3-azaprop-2-enoylamino}-4-methyl-2-oxoazetidinesulfonic acid (10)

The titled compound was prepared following scheme 1.
The preparation of the compound of formula A (2Z)-3-(2-{N-[(4-methoxyphenyl)methoxy]acetylamino}ethoxy)-2-{2-[(triphenylmethyl)amino](1,3-thiazol-4-yl)}-3-azaprop-2-enoic acid was prepared according to the procedures described in Bioorg. Med. Chem. Lett. 1996, 2077 and (3S,4S)-3-amino-4-methyl-2-oxoazetidinesulfonic acid was prepared according to the procedures described in J. Org. Chem. 1980, 410.

Final assembly and deprotection steps were done similarly according to the method described for the example 1.

Example 11

(3S,4S)-3-{2-(2-amino(1,3-thiazol-4-yl))-3-[(1-amino-5-hydroxy-4-oxo(2-hydropyridyl))methoxy]-3-azaprop-2-enoylamino}-4-methyl-2-oxoazetidinesulfonic acid (11)

The titled compound was prepared following scheme 1.
1-[(1E)-2-(4-nitrophenyl)-1-azavinyl]-5-(diphenylmethoxy)-2-(hydroxymethyl)hydropyridin-4-one was prepared from kojic acid according to the procedure described in Helv. Chim. Acta 1960, 461

Compound of formula A 3-({1-[(1E)-2-(4-nitrophenyl)-1-azavinyl]-5-(diphenylmethoxy)-4-oxo(2-hydropyridyl)}methoxy)(2Z)-2-{2-[(triphenylmethyl)amino](1,3-thiazol-4-yl)}-3-azaprop-2-enoic acid was prepared according to the procedures described in example 1 and (3S,4S)-3-amino-4-methyl-2-oxoazetidinesulfonic acid was prepared according to the procedures described in J. Org. Chem. 1980, 410.

Final assembly and deprotection steps were done similarly according to the method described for the example 1.

Example 12

2-((3S,4S)-3-{(2Z)-2-(2-amino-5-chloro(1,3-thiazol-4-yl))-3-[(1,5-dihydroxy-4-oxo(2-hydropyridyl))methoxy]-3-azaprop-2-enoylamino}-4-[(aminocarbonyloxy)methyl]-2-oxoazetidinyloxy)acetic acid (42)

The titled compound was prepared following scheme 1.
The preparation of the compound of formula A (2Z)-3-{[1,5-bis(diphenylmethoxy)-4-oxo(2-hydropyridyl)]methoxy}-2-{5-chloro-2-[(triphenylmethyl)amino](1,3-thiazol-4-yl)}-3-azaprop-2-enoic acid was achieved according to the procedures described in J. Antibiotics, 1990, 1450 and WO-A-02/22613 using 2-{5-Chloro-2-[(triphenylmethyl)amino](1,3-thiazol-4-yl)}-2-oxoacetic acid (obtained from 2-oxo-2-{2-[(triphenylmethyl)amino](1,3-thiazol-4-yl)}acetic acid (DE2710902A1) and chlorination step achieved according to the procedures described in EP-A-0 055 465) and 2-[(aminooxy)methyl]-5-(diphenylmethoxy)-1-methylhydroxyridine-4-one (described in example 1).

The preparation of the compound of formula B 2-(trimethylsilyl)-ethyl {(3S,4S)-3-amino-4[(aminocarbonyloxy)methyl]-2-oxoazetidinyloxy}acetate was prepared as followed:

Preparation of 2-[(tert-butoxy)carbonylamino]-3,4-dihydroxy-N-(phenylmethoxy) butanamide To solution of tetrahydrofuran (THF, 6 L) and phosphoric acid buffer (0.025 M, $KH_2PO_4/Na_2HPO_4$; ratio 1/1, 2 L) containing ethyl 3-[(tert-butoxy)carbonylamino]-2-hydroxy-3-[N-(phenylmethoxy) carbamoyl]propanoate (compound prepared from diethyl tartrate according to the procedures described in Org. Synth., Coll. Vol. 1998, 220, J. Org. Chem. 1983, 3556 and U.S. Pat. No. 4,794,108) (120 g, 31.38 mmol), sodium borohydride (59.35 g, 156.9 mmol) was added portion wise at 0° C. over 1 h. The resulting mixture was stirred at 0° C. for an additional 1 h and at room temperature for 2 h. The micxture was cooled at 0° C. before addition of 1M aqueous solution containing $H_3PO_4$ until the pH reach 8. NaCl (100 g) was added to the mixture and the organic layer was separated. Extraction with ethyl acetate (3×1.5 L) was performed and the combined organic phases were washed with brine (1 L), dried over $MgSO_4$ and evaporated under vacuo. The residue as purified by column chromatography using hexane/acetone as eluent to get 50 g of white solid.

–ESI-MS spectrum: m/z: 339 [M–1]$^+$.

Preparation of 2-[(tert-butoxy)carbonylamino]-3-hydroxy-N-(phenylmethoxy)-4-(1,1,2,2-tetramethyl-1-silapropoxy)butanamide

[(Tert-butoxy)carbonylamino]-3,4-dihydroxy-N-(phenylmethoxy) butanamide (47 g, 138 mmol), imidazole (37.5 g, 552 mmol) and tert-butyldimethylsilyl chloride (57.7 g, 386.4 mmol) were stirred at 0° C. for 1 h and the room temperature for an additional 1 h in a mixture of dichloromethane (1.7 L) and dimethylformamide (17 mL). Water (250 mL) was added and after decantation, water (2×250 mL) and brine (250 mL) was used for washing the organic phases, which was dried over Na2SO4. After evaporation of the solvent, the residue was purified by column chromatography using a mixture of ethyl acetate/hexane (1/4) as eluent to get 28 g of the desired product.

1H-NMR (CDCl$_3$) δ: 0.06 (s, 6H), 0.88 (s, 9H), 1.42 (s, 9H), 3.65-3.70 (m, 1H), 3.75-3.85 (m, 2H), 4.05-4.15 (m, 1H), 4.90 (s, 2H), 5.65-5.75 (m, 1H), 7.30-7.50 (m, 5H).

Preparation of N-{(3S,4S)-2-oxo-1-(phenylmethoxy)-4-[(1,1,2,2-tetramethyl-1-silapropoxy)methyl]azetidin-3-yl}(tert-butoxy)carboxamide A solution of THF (1.5 L) containing 2-[(tert-butoxy)carbonylamino]-3-hydroxy-N-(phenylmethoxy)-4-(1,1,2,2-tetramethyl-1-silapropoxy)butanamide (9.8 g, 21.56 mmol), triphenylphosphine (17.5 g, 66.8 mmol) and diethyl azodicarboxylate (11.26 g, 64.7 mmol) was stirred at room temperature for 2 h. The solvent was evaporated in vacuo and the residue was purified under column chromatography using a mixture of ethyl acetate and hexane (1/4) as eluent to obtained 7.25 g of the desired product.

1H-NMR (CDCl$_3$) δ: 0.09 (s, 6H), 0.89 (s, 9H), 1.40 (s, 9H), 3.40-3.45 (m, 1H), 3.62 (d, 1H, J=7.2 Hz), 3.88 (d, 1H, J=7.2 Hz), 4.83 (m, 1H), 4.94 (s, 2H), 5.51 (d, 1H, J=6.5 Hz), 7.35-7.45 (m, 5H).

Preparation of N-[(3S,4S)-4-(hydroxymethyl)-2-oxo-1-(phenylmethoxy)azetidin-3-yl] (tert-butoxy)carboxamide N-{(3S,4S)-2-oxo-1-(phenylmethoxy)-4-[(1,1,2,2-tetramethyl-1-silapropoxy)methyl]azetidin-3-yl}(tert-butoxy)carboxamide (2.80 g, 6.41 mmol) was dissolved in THF (50 mL) and pyridine (5 mL). Pyridine-hydrofluoride complex (4.0 mL, 2.6 eq of pyridine, 24 eq of HF) was added at −20° C. After 10 min, the mixture was warmed up at room temperature and stirred for 3.5 h. Phosphoric acid buffer (0.025 M, KH$_2$PO$_4$/Na$_2$HPO$_4$; ratio 1/1, 400 mL) was added and the resulting solution was extracted with ethyl acetate (3×100 mL). The organic phase was dried over Na$_2$SO$_4$ and the solvent was evaporated in vacuo. 2.04 g of the desired product was obtained and used for the next step.

1H-NMR (DMSO-d6) δ: 1.38 (s, 9H), 3.50-3.60 (m, 2H), 3.95-4.05 (m, 1H), 4.70-4.80 (m, 1H), 4.94 (s, 2H), 5.00-5.10 (m, 1H), 7.20-7.30 (m, 1H), 7.35-7.50 (m, 5H).

Preparation of {(2S,3S)-3-[(tert-butoxy)carbonylamino]-4-oxo-1-(phenylmethoxy)azetidin-2-yl}methyl aminooate (reaction done according to procedures described in Chem., Eur. J. 2005, 1949)

In anhydrous dichloromethane (100 mL), N-[(3S,4S)-4-(hydroxymethyl)-2-oxo-1-(phenylmethoxy)azetidin-3-yl](tert-butoxy)carboxamide (1.0 g, 3.1 mmol) and trichloroacetyl chloride (1.11 mL, 9.3 mmol) were stirred at 5° C. for 30 min. Then aluminium oxide (9.6 g) was added and the solvent was remove in vacuo. After 2 h at room temperature, the residue was taking up with ethyl acetate (40 mL) and stirred for 30 min. The eluent was concentrated and the residue was purified by column chromatography using ethyl acetate/hexane (1/2) as eluent to afford 0.895 g of the desired compound.

1H-NMR (DMSO-d6) δ: 1.39 (s, 9H), 3.90-4.20 (m, 3H), 4.80-4.90 (m, 1H), 4.91 (s, 2H), 6.50-6.80 (broad band for NH$_2$, 2H), 7.30-7.50 (m, 5H), 7.55-7.60 (m, 1H).

Preparation of {(2S,3S)-3-[(tert-butoxy)carbonylamino]-1-hydroxy-4-oxoazetidin-2-yl}methyl aminooate {(2S,3S)-3-[(tert-butoxy)carbonylamino]-4-oxo-1-(phenylmethoxy)azetidin-2-yl}methyl aminooate (0.086 g, 0.24 mmol) was dissolved in a mixture of ethyl acetate (4 mL) and methanol (4 mL) under hydrogen atmosphere at room temperature in presence of Pd/C (10%, 25 mg). The reaction was stirred for 2 h and the mixture was filtrated over celite bed. The filtrate was evaporated in vacuo to give 0.055 g of the desired compound.

1H-NMR (DMSO-d6) δ: 1.39 (s, 9H), 3.95-4.10 (m, 3H), 4.75-4.80 (m, 1H), 6.45-6.70 (broad band for NH$_2$, 2H), 7.57 (d, 1H, J=6.0 Hz).

Preparation of (trimethylsilyl)-ethyl 2-{(3S,4S)-3-amino-4-[(aminocarbonyloxy)methyl]-2-oxoazetidinyloxy}acetate The titled compound was prepared from {(2S,3S)-3-[(tert-butoxy)carbonylamino]-1-hydroxy-4-oxoazetidin-2-yl}methyl aminooate according to the procedures described in J. Med. Chem. 1985, 1447 and J. Antibiotics, 1985, 813.

1H-NMR (CDCl$_3$) δ: 0.02 (s, 9H), 0.99 (t, 2H, J=8.6 Hz), 1.37 (s, 9H), 3.90-4.30 (m, 5H), 4.53 (dd, 2H, J=16.4, 21.6 Hz), 4.84 (dd, 1H, J=5.4, 9.4 Hz), 6.70-6.40 (broad band for NH$_2$, 2H), 7.48 (d, 1H, J=9.6 Hz)

Final assembly and deprotection steps were done similarly according to the method described for the example 1 and J. Med. Chem. 1985, 1447.

Example 13

((2S,3S)-3-{(2Z)-2-(5-amino(1,2,4-thiadiazol-3-yl))-3-[(1,5-dihydroxy-4-oxo(2-hydropyridyl))methoxy]-3-azaprop-2-enoylamino}-1-(hydroxysulfonyloxy)-4-oxoazetidin-2-yl)methyl aminooate (48)

The titled compound was prepared following scheme 1.

The preparation of the compound of formula A (2Z)-3-{[1,5-bis(diphenylmethoxy)-4-oxo(2-hydropyridyl)]methoxy}-2-{5-[(triphenylmethyl)amino] (1,2,4-thiadiazol-3-yl)}-3-azaprop-2-enoic acid was achieved according to the procedures described in example 1 from 2-oxo-2-{5-[(triphenylmethyl)amino](1,2,4-thiadiazol-3-yl)}acetic acid (EP-A-0 333 154 and GB-A-2102423).

The preparation of the compound of formula B [(2S,3S)-3-amino-1-(hydroxysulfonyloxy)-4-oxoazetidin-2-yl]methyl aminooate was achieved according to the procedures described in J. Antibiotics 1985, 1536 from {(2S,3S)-3-[(tert-butoxy)carbonylamino]-1-hydroxy-4-oxoazetidin-2-yl}methyl aminooate (example 12).

Final assembly and deprotection steps were done similarly according to the method described for the example 1 and J. Med. Chem. 1985, 1447.

Compound 8 was prepared in analogy to the procedures described in WO-A-02/22613. The corresponding hydroxylamine derivative (NH$_2$—O—R4) was prepared in analogy to the procedure described in J. Med. Chem. 2004, 6349.

Compound 9 was prepared in analogy to the procedures described in WO-A-02/22613. The corresponding azetidinone ring of formula B was prepared in analogy to the procedures described in J. Am. Chem. Soc. 1980, 7076 and J. Org. Chem. 1982, 5160.

Compound 13 was prepared in analogy to the procedures described in WO-A-02/22613. The corresponding azetidinone ring or formula B was prepared in analogy to the procedures described in J. Antibiotics 1986, 76.

Compound 14 was prepared in analogy to the procedures described in WO-A-02/22613. The corresponding azetidinone of formula B was prepared in analogy to the procedures described in DE-A-3229439.

Compound 15 was prepared in analogy to the procedures described in WO-A-02/22613. The corresponding heterocycle of the carboxylic acid derivative of formula A was prepared in analogy to the procedures described in Russ. J. Org. Chem. 1995, 240 and J. Antibiotics 1983 1020.

Compound 16 was prepared in analogy to the procedures described in WO-A-02/22613. The corresponding heterocycle of the carboxylic acid derivative of formula A was prepared in analogy to the procedures described in Z. Chem 1975, 233 and J. Antibiotics 1983, 1020.

Compound 17 was prepared in analogy to the procedures described in WO-A-02/22613. The corresponding heterocycle of the carboxylic acid derivative of formula A was prepared in analogy to the procedures described in U.S. Pat. No. 4,394,504 and J. Antibiotics 1983, 1020.

Compounds 18 and 19 were prepared in analogy to the procedures described in WO-A-02/22613. The corresponding heterocycles of the carboxylic acid derivatives of formula A was prepared in analogy to the procedures described in J. Am. Chem. Soc. 1959, 2452, WO-A-95/33724 and J. Antibiotics 1983, 1020 using respectively the methyl hydrazine and hydrazine as starting material.

Compound 20 was prepared in analogy to the procedures described in WO-A-02/22613. The corresponding heterocycle of the carboxylic acid derivative of formula A was prepared in analogy to the procedures described in U.S. Pat. No. 4,394,504 but using 2-amino-6-picoline as starting material.

Compound 24 was prepared in analogy to the procedures described in WO-A-02/22613. The corresponding azetidinone ring of formula B was prepared in analogy to the procedures described in example 13 and J. Antibiotics 1983, 1201.

Compound 25 was prepared in analogy to the procedures described in WO-A-02/22613. The corresponding azetidinone ring of formula B was prepared in analogy to the procedures described in example 13.

Compound 27 was prepared in analogy to the procedures described in WO-A-02/22613. The corresponding hydroxylamine derivative (NH$_2$—O—R4) was prepared according to the synthetic scheme B-3-II.

Compound 30 was prepared in analogy to the procedures described in example 7 using the same compound of formula B and the compound of formula A described in example 13.

Compound 31 was prepared in analogy to the procedures described in example 6 using the same compound of formula B and the compound of formula A described in example 12.

Compound 32 was prepared in analogy to the procedures described in example 6 using the same compound of formula B and the compound of formula A described in example 13.

Compound 35 was prepared in analogy to the procedures described in examples 4 and 6 for preparing the compound of formula B and of example 13 for preparing compound of formula A.

Compound 36 was prepared in analogy to the procedures described in example 4 using the same compound of formula B and the compound of formula A described in example 12.

Compound 37 was prepared in analogy to the procedures described in example 4 using the same compound of formula B and the compound of formula A described in example 13.

Compound 38 was prepared in analogy to the procedures described in example 6 and after reduction of the N-hydroxy group to NH (J. Am. Chem. Soc. 1980, 7076), the final sulfonylation was performed in analogy to example 3 to obtain the compound of formula B. Procedures of example 12 were used for preparing the compound of formula A.

Compound 39 was prepared in analogy to the procedures described in example 6 and after reduction of the N-hydroxy group to NH (J. Am. Chem. Soc. 1980, 7076), the final sulfonylation was performed in analogy to example 3 to obtain the compound of formula B.

Compound 40 was prepared in analogy to the procedures described in example 6 and after reduction of the N-hydroxy group to NH (J. Am. Chem. Soc. 1980, 7076), the final sulfonylation was performed in analogy to example 3 to obtain the compound of formula B. Procedures of example 13 were used for preparing the compound of formula A.

Compound 41 was prepared in analogy to the procedures described in example 12 for preparing the compound of formula B.

Compound 43 was prepared in analogy to the procedures described in example 12 for preparing the compound of formula B. Procedures of example 13 were used for preparing the compound of formula A.

Compound 44 was prepared in analogy to the procedures described in example 12 and J. Antibiotics 1983, 1201 for preparing the compound of formula B.

Compound 45 was prepared in analogy to the procedures described in example 12 and J. Antibiotics 1983, 1201 for preparing the compound of formula B. Procedures of example 12 were used for preparing the compound of formula A.

Compound 46 was prepared in analogy to the procedures described in example 12 and J. Antibiotics 1983, 1201 for preparing the compound of formula B. Procedures of example 13 were used for preparing the compound of formula A.

Compound 47 was prepared in analogy to the procedures described in example 12 for preparing the compound of formula B. Procedures of example 12 were used for preparing the compound of formula A.

In the following table X the analytical data for all compounds of formula (I) made are presented:

TABLE X

| Compound Number (Example Number) | 1H-NMR (DMSO-d6) δ in ppm | Mass m/z: |
|---|---|---|
| 5 (8) | 1.41 (d, 3H, J = 6.0 Hz), 3.70 (m, 1H), 3.5-6 (broad band for OH and NH$_2$), 4.20 (s, 3H), 4.43 (dd, 1H, J = 2.56-7.6 Hz), 5.32 (s, 2H), 6.85 (s, 1H), 6.98 (s, 1H), 8.52 (s, 1H), 9.46 (d, 1H, J = 7.6 Hz). | |

TABLE X-continued

| Compound Number (Example Number) | 1H-NMR (DMSO-d6) δ in ppm | Mass m/z: |
|---|---|---|
| 6 (1) | 1.41 (d, 3H, J = 6.0 Hz), 3.62 (s, 3H), 3.67 (m, 1H) 4.43 (dd, 1H, J = 2.5, 7.7 Hz), 5.06 (s, 2H), 6.26 (s, 1H), 6.75 (s, 1H), 7.23 (s br, 2H), 7.45 (s, 1H), 9.40 (d, 1H, J = 7.7 Hz). | |
| 7 (9) | 1.42 (d, 3H, J = 6.1 Hz), 3.71 (qd, 1H, J = 2.4 and 6.1 Hz), 4.47 (dd, 1H, J = 2.4 and 7.8 Hz), 5.32 (s, 2H), 6.87 (s, 1H), 7.09 (s, 1H), 7.2-7.5 (Broad Band for NH$_2$), 8.50 (s, 1H), 9.53 (d, 1H, J = 7.8 Hz). | |
| 9 | 3.33 (m, 1H), 3.67 (m, 1H), 4.98 (m, 1H), 5.28 (s, 2H), 6.85 (s, 1H), 6.99 (s, 1H), 7.16 (Broad Band for NH$_2$), 8.09 (s, 1H), 9.46 (d, 1H, J = 7.8 Hz). | |
| 10 (10) | 1.42 (d, 3H, J = 6.1 Hz), 1.99 (s, 3H), 3.67 (m, 1H), 3.79 (m, 2H), 4.23 (m, 2H), 4.43 (m, 1H), 6.86 (s, 1H), 9.15 (m, 1H), 9.93 (s broad, 1H). | |
| 11 (11) | 1.42 (d, 3H, J = 6.2 Hz), 3.74 (m, 1H), 4.48 (m, 1H), 5.41 (s, 2H), 6.94 (s, 1H), 7.20 (s, 1H), 8.29 (s, 1H), 9.59 (d, 1H, J = 7.7 Hz). | |
| 12 (2) | 1.39 (d, 3H, J = 6.2 Hz), 4.02 (m, 1H), 4.48 (m, 1H), 5.30 (s, 2H), 6.84 (s, 1H), 7.05 (s, 1H), 7.27 (br, s, 2H), 8.16 (s, 1H), 9.69 (d, 1H, J = 7.7 Hz). | |
| 13 | 1.61 (d, 3H, J = 6.2 Hz), 4.43 (m, 1H), 4.87 (m, 1H), 5.30 (s, 2H), 6.89 (s, 1H), 6.99 (s, 1H), 7.27 (br, s, 2H), 8.11 (s, 1H), 9.57 (d, 1H, J = 7.7 Hz). | |
| 14 | | 518 (M + 1) |
| 15 | 1.41 (d, 3H, J = 6.2 Hz), 3.65 (m, 1H), 4.44 (m, 1H), 5.34 (s, 2H), 7.06 (s, 1H), 8.17 (s, 1H), 9.47 (d, 1H, J = 7.7 Hz). | |
| 16 | 1.41 (d, 3H, J = 6.2 Hz), 3.62 (m, 1H), 4.44 (m, 1H), 5.27 (s, 2H), 6.76 (s, 1H), 7.83 (s, 1H), 8.10 (broad s, 2H), 9.64 (d, 1H, J = 7.7 Hz). | |
| 17 | 1.42 (d, 3H, J = 6.2 Hz), 3.10 (m, 1H), 4.47 (m, 1H), 5.31 (s, 2H), 6.10 (s, 1H), 8.86 (s, 1H), 7.90 (s, 1H), 9.72 (d, 1H, J = 7.7 Hz). | |
| 18 | 1.42 (d, 3H, J = 6.2 Hz), 3.51 (m, 3H), 3.65 (m, 1H), 4.42 (m, 1H), 5.17 (s, 2H), 5.47 (s, 1H), 6.10 (s, 1H), 6.85 (s, 1H), 7.20 (br, s, 2H), 7.95 (s, 1H), 9.28 (d, 1H, J = 7.7 Hz). | |
| 19 | 1.38 (d, 3H, J = 6.2 Hz), 3.68 (m, 1H), 4.39 (m, 1H), 5.17 (s, 1H), 5.31 (s, 2H), 6.78 (s, 1H), 7.89 (s, 1H), 9.24 (d, 1H, J = 7.7 Hz). | |
| 20 | 1.43 (d, 3H, J = 6.2 Hz), 3.73 (m, 1H), 4.48 (m, 1H), 5.38 (s, 2H), 6.72 (d, 1H, J = 5.7 Hz), 6.83 (d, 1H, J = 5.7 Hz), 6.98 (s, 1H), 7.62 (t, 1H, J = 5.7 Hz), 8.04 (s, 1H), 9.54 (d, 1H, J = 7.7 Hz). | |
| 21 (3) | 1.43 (d, 3H), 3.67 (m, 1H), 4.45 (m, 1H), 5.47 (s, 2H), 6.56 (s, 1H), 7.05 (s, 1H), 8.10-8.20 (m, 3H), 9.50 (d, 1H, J = 7.7 Hz) | |
| 22 (4) | 1.41 (d, 3H, J = 6.2 Hz), 4.01 (m, 1H), 4.37 (m, 1H), 4.52 (AB, 2H, J = 16.4 Hz), 5.18 (s, 2H), 6.73 (s, 1H), 6.81 (s, 1H), 7.28 (br, s, 2H), 7.84 (s, 1H), 9.44 (d, 1H, J = 7.7 Hz). | |
| 23 (5) | 1.35-1.45 (m, 5H), 3.91 (m, 1H), 4.42 (m, 1H), 4.53 (m, 1H), 5.29 (s, 2H), 6.84 (s, 1H), 6.99 (s, 1H), 7.37 (br, s, 2H), 8.16 (s, 1H), 9.51 (d, 1H, J = 7.7 Hz). | |
| 24 | 4.40-4.80 (m, 3H), 5.20 (m, 1H), 5.27 (s, 2H), 6.81 (s, 1H), 7.06 (s, 1H), 7.30 (br, s, 2H), 8.17 (s, 1H), 9.56 (d, 1H, J = 7.7 Hz). | |
| 25 | 4.15 (m, 2H), 4.42 (m, 1H), 5.20-5.30 (m, 3H), 6.40-6.60 (br, s, 2H), 6.82 (s, 1H), 6.91 (s, 1H), 7.20-7.40 (br, s, 2H), 7.99 (s, 1H), 9.42 (d, 1H, J = 7.7 Hz) | |
| 26 (6) | 1.22 (d, 3H), 1.42 (d, 3H), 4.63 (d, 1H, J = 7.7 Hz), 5.23 (s, 2H), 6.81 (s, 1H), 7.00 (s, 1H), 7.27 (br, s, 2H), 8.08 (s, 1H), 9.59 (d, 1H, J = 7.7 Hz) | |
| 27 | 1.38 (m, 3H), 3.72 (m, 1H), 4.44 (m, 1H), 5.12 (s, 2H), 6.81 (s, 1H), 7.00 (s, 1H), 7.27 (br, s, 2H), 8.08 (s, 1H), 9.59 (d, 1H, J = 7.7 Hz) | |
| 28 | | 488 (M + 1) |
| 29 (7) | 1.31 (d, 3H, J = 6.2 Hz), 3.96 (m, 1H), 4.44 (m, 1H), 5.27 (s, 2H), 6.80 (s, 1H), 7.40-7.60 (br, s, 2H), 7.82 (m, 1H), 8.11 (m, 1H), 8.22 (m, 1H), 8.75 (m, 1H), 9.39 (d, 1H, J = 7.7 Hz). | |
| 30 | 1.38 (d, 3H, J = 6.2 Hz), 3.90 (m, 1H), 4.46 (m, 1H), 5.21 (s, 2H), 6.69 (s, 1H), 7.74 (s, 1H), 8.15 (br, s, 2H), 9.68 (d, 1H, J = 7.7 Hz) | |

TABLE X-continued

| Compound Number (Example Number) | 1H-NMR (DMSO-d6) δ in ppm | Mass m/z: |
|---|---|---|
| 31 | 1.22 (s, 3H), 1.42 (s, 3H), 4.58 (d, 1H, J = 7.7 Hz), 5.17 (s, 2H), 6.87 (s, 1H), 7.40 (br, s, 2H), 7.88 (s, 1H), 9.56 (d, 1H, J = 7.7 Hz). | |
| 32 | 1.24 (s, 3H), 1.43 (s, 3H), 4.61 (d, 1H, J = 7.7 Hz), 5.38 (s, 2H), 7.09 (s, 1H), 8.16 (br, s, 2H), 8.21 (s, 1H), 9.63 (d, 1H, J = 7.7 Hz). | |
| 33 | 1.23 (s, 3H), 1.48 (s, 3H), 4.49 (AB, 2H, J = 16.0 Hz), 4.70 (d, 1H, J = 7.7 Hz), 5.28 (s, 2H), 6.85 (s, 2H), 7.04 (s, 1H), 8.16 (s, 1H), 9.55 (d, 1H, J = 7.7 Hz). | |
| 34 | 1.23 (s, 3H), 1.47 (s, 3H), 4.48 (AB, 2H, J = 16. Hz), 4.64 (d, 1H, J = 7.7 Hz), 5.26 (s, 2H), 7.04 (s, 1H), 7.42 (br, s, 2H), 8.16 (s, 1H), 9.49 (d, 1H, J = 7.7 Hz). | |
| 35 | 1.24 (s, 3H), 1.48 (s, 3H), 4.49 (AB, 2H, J = 16.0 Hz), 4.68 (d, 1H, J = 7.7 Hz), 5.30 (s, 2H), 6.88 (s, 2H), 7.98 (s, 1H), 8.17 (br, s, 2H), 9.54 (d, 1H, J = 7.7 Hz). | |
| 36 | 1.41 (d, 3H, J = 6.2 Hz), 3.90 (m, 1H), 4.42 (m, 1H), 4.52 (AB, 2H, J = 16.4 Hz), 5.28 (s, 2H), 7.00 (s, 1H), 7.44 (br, s, 2H), 8.11 (s, 1H), 9.42 (d, 1H, J = 7.7 Hz). | |
| 37 | 1.42 (d, 3H, J = 6.2 Hz), 3.89 (m, 1H) 4.42 (m, 1H), 4.52 (AB, 2H, J = 16.4 Hz), 5.33 (s, 2H), 6.91 (s, 1H), 8.05 (s, 1H), 8.17 (br, s, 2H), 9.43 (d, 1H, = 7.7 Hz). | |
| 38 | 1.24 (s, 3H), 1.46 (s, 3H), 4.58 (d, 1H, J = 7.7 Hz), 5.17 (s, 2H), 6.87 (s, 1H), 7.42 (br, s, 2H), 7.86 (s, 1H), 9.45 (d, 1H, J = 7.7 Hz). | |
| 39 | 1.25 (d, 3H), 1.49 (d, 3H), 4.64 (d, 1H, J = 7.7 Hz), 5.25 (s, 2H), 6.83 (s, 1H), 7.04 (s, 1H), 7.31 (br, s, 2H), 8.12 (s, 1H), 9.47 (d, 1H, J = 7.7 Hz). | |
| 40 | 1.25 (s, 3H), 1.48 (s, 3H), 4.61 (d, 1H, J = 7.7 Hz), 5.35 (s, 2H), 7.04 (s, 1H), 8.10-8.15 (m, 3H), 9.46 (d, 1H, J = 7.7 Hz). | |
| 41 | 3.50-3.60 (m, 2H), 4.00 (m, 1H), 4.23 (m, 1H), 4.36 (m, 1H), 4.50 (m, 2H), 5.20-5.30 (m, 3H), 6.50-6.70 (br, s, 2H), 6.83 (s, 1H), 6.95 (s, 1H), 7.27 (s, 2H), 8.06 (s, 1H), 9.35 (d, 1H, J = 7.7 Hz). | |
| 42 (12) | 3.50-3.60 (m, 2H), 3.95 (m, 1H), 4.20-4.40 (m, 2H), 4.45 (m, 2H), 5.17 (m, 1H), 5.27 (s, 2H); 6.50-6.70 (br, s, 2H), 6.92 (s, 1H), 7.38 (s, 2H), 7.98 (s, 1H), 9.33 (d, 1H, J = 7.7 Hz). | |
| 43 | 3.50-3.60 (m, 2H), 3.91 (m, 1H), 4.27 (m, 1H), 4.30 (m, 1H), 4.49 (m, 2H), 5.22 (m, 1H), 5.28 (s, 2H); 6.53 (br, s, 2H), 6.83 (s, 1H), 7.95 (s, 1H), 8.13 (s, 2H), 9.32 (d, 1H, J = 7.7 Hz). | |
| 47 | 4.06 (m, 1H), 4.27 (m, 1H), 4.40 (m, 1H), 5.12 (m, 1H), 5.25 (s, 2H), 6.40-6.60 (br, s, 2H), 6.98 (s, 1H), 7.40 (s, 1H), 8.03 (s, 1H), 9.34 (d, 1H, J = 7.7 Hz). | |
| 48 (13) | 4.07 (m, 1H), 4.27 (m, 1H), 4.42 (m, 1H), 5.15 (m, 1H), 5.36 (s, 2H), 6.30-6.50 (br, s, 2H), 7.03 (s, 1H), 8.13 (s, 1H), 8.17 (s, 1H), 9.36 (d, 1H, J = 7.7 Hz). | |

Example 14

(1S,5R)-2-[2-(3-carbamoyl-6-methylpyridinium) acetyl]-7-oxo-2,6-diazabicyclo[3.2.0]heptane-6-sulfonate, inner salt (111)

The titled compound was prepared following scheme 11.

a) Preparation of 5-carbamoyl-1-carboxymethyl-2-methyl-pyridinium bromide

A solution of 6-methyl nicotinamide (400 mg, 2.94 mmol, 1.0 eq) and bromoacetic acid (408 mg, 2.94 mmol, 1.0 eq) in DMF (10 mL) was stirred at room temperature for 6 days. The reaction mixture was monitored by LCMS. Solvent was then evaporated and the crude product was purified by preparative HPLC to afford 136 mg of the expected compound.

1H-NMR (DMSO-$d_6$) δ (ppm): 2.80 (s, 3H); 5.66 (s, 2H); 8.13 (s, 1H); 8.24 (d, J=8.3, 1H); 8.53 (s, 1H); 8.92 (dd, J=1.8 and 8.3, 1H); 9.47 (s, 1H).

b) (1S,5R)-2-[2-(3-carbamoyl-6-methylpyridinium) acetyl]-7-oxo-2,6-diazabicyclo[3.2.0]heptane-6-sulfonate, inner salt (111)

5-carbamoyl-1-carboxymethyl-2-methyl-pyridinium bromide (91 mg, 0.47 mmol, 1.0 eq) was added at room temperature to a stirred solution of (1S,5R)-7-oxo-2,6-diazabicyclo[3.2.0]heptane-6-sulfonic acid (J. Med. Chem. 1998, 3961) (90 mg, 0.47 mmol, 1.0 eq) in DMSO (4 mL), followed by 1-hydroxybenzotriazol (69 mg, 0.52 mmol, 1.1 eq), dicyclohexylcarbodiimide (106 mg, 0.52 mmol, 1.1 eq) and diisopropylethylamine (96 µL, 0.56 mmol, 1.2 eq). After stirring overnight at room temperature, the reaction mixture was filtered. The mother liquid was evaporated and the crude product was dissolved in CH$_2$Cl$_2$ (4 mL) and filtered. The resulting solid was purified by preparative HPLC to afford 46 mg of the expected compound.

1H-NMR (DMSO-d$_6$) δ (ppm): 1.82 (m, 1H); 2.42 (m, 1H); 2.73 (d, J=5.3, 3H); 3.25 and 3.55 (2m, 1H); 4.05 (m, 1H); 4.40 and 4.62 (2t, J=4.7, 1H); 5.19 and 5.31 (2d, J=4.3, 1H); 5.55-6.05 (AB part of a ABX system, the X part being in the $^{15}$N spectrum, 2H); 8.12 (d, J=7.0, 1H); 8.22 (d, J=8.3, 1H); 8.53 (d, J=10.0, 1H); 8.89 (dd, J=1.8 and 8.3, 1H); 9.36 (dd, J=1.8 and 10.0, 1H).

Example 15

(1S,5R)-2-{2-[3-(N-methylcarbamoyl)pyridinium] acetyl}-7-oxo-2,6-diazabicyclo[3.2.0]heptane-6-sulfonate, inner salt (101)

The titled compound was prepared following scheme 11 and in analogy to example 14 using (1S,5R)-7-oxo-2,6-diazabicyclo[3.2.0]heptane-6-sulfonic acid (compound H) and the commercially available N-methyl nicotinamide as starting materials.

+ESI-MS spectrum: m/z: 289 [M+H—SO$_3$]$^+$.

Example 16

(1S,5R)-2-[2-(4-aminopyridinium)acetyl]-7-oxo-2,6-diazabicyclo[3.2.0]heptane-6-sulfonate, inner salt (103)

The titled compound was prepared following scheme 11 and in analogy to example 14 using (1S,5R)-7-oxo-2,6-diazabicyclo[3.2.0]heptane-6-sulfonic acid (compound H) and the commercially available 4-aminopyridine as starting materials.

+ESI-MS spectrum: m/z: 326 [M]$^+$.

Example 17

(1S,5R)-2-(2-(2-isoquinolinium)acetyl)-7-oxo-2,6-diazabicyclo[3.2.0]heptane-6-sulfonate, inner salt (104)

The titled compound was prepared following scheme 11 and in analogy to example 14 using (1S,5R)-7-oxo-2,6-diazabicyclo[3.2.0]heptane-6-sulfonic acid (compound H) and the commercially available isoquinoline as starting materials.

−ESI-MS spectrum: m/z: 360 [M−1]$^+$.

Example 18

(1S,5R)-2-[2-(4-carbamoylpyridinium)acetyl]-7-oxo-2,6-diazabicyclo[3.2.0]heptane-6-sulfonate, inner salt (105)

The titled compound was prepared following scheme 11 and in analogy to example 14 using (1S,5R)-7-oxo-2,6-diazabicyclo[3.2.0]heptane-6-sulfonic acid (compound H) and the commercially available isonicotinamide as starting materials.

1H-NMR (DMSO-d$_6$): 1.78 (m, 1H); 2.40 (m, 1H); 3.20 and 3.50 (2m, 1H); 4.05 and 4.12 (2m, 1H); 4.43 and 4.60 (2t, J=4.7, 1H); 5.21 and 5.29 (2d, J=4.3, 1H); 5.55-6.00 (AB part of a ABX system, the X part being in the $^{15}$N spectrum, 2H); 8.27 (m, 1H); 8.46 (m, 2H); 8.65 (m, 1H); 9.12 (m, 2H).

Example 19

(1S,5R)-7-oxo-2-(2-(2-5,6,7,8-tetrahydroisoquinolinium)acetyl)-2,6-diazabicyclo[3.2.0]heptane-6-sulfonate, inner salt (106)

The titled compound was prepared following scheme 11 and in analogy to example 14 using (1S,5R)-7-oxo-2,6-diazabicyclo[3.2.0]heptane-6-sulfonic acid (compound H) and the commercially available 5,6,7,8-tetrahydroisoquinoline as starting materials.

+ESI-MS spectrum: m/z: 365 [M]$^+$.

Example 20

(1S,5R)-2-[2-(3-aminopyridinium)acetyl]-7-oxo-2,6-diazabicyclo[3.2.0]heptane-6-sulfonate, inner salt (107)

The titled compound was prepared following scheme 11 and in analogy to example 14 using (1S,5R)-7-oxo-2,6-diazabicyclo[3.2.0]heptane-6-sulfonic acid (compound H) and the commercially available 3-aminopyridine as starting materials.

+ESI-MS spectrum: m/z: 326 [M]$^+$.

Example 21

(1S,5R)-2-(2-{3-[N-(carbamoylmethyl)carbamoyl] pyridinium}acetyl)-7-oxo-2,6-diazabicyclo[3.2.0] heptane-6-sulfonate, inner salt (108)

The titled compound was prepared following scheme 11 and in analogy to example 14 using (1S,5R)-7-oxo-2,6-diazabicyclo[3.2.0]heptane-6-sulfonic acid (compound H) and 3-[N-(carbamoylmethyl)carbamoyl]pyridine as starting materials.

+ESI-MS spectrum: m/z: 411 [M]$^+$.

3-[N-(carbamoylmethyl)carbamoyl]pyridine was prepared by reacting the commercially available nicotinyl chloride hydrochloride with glycinamide hydrochloride.

Example 22

(1S,5R)-2-{2-[3-(N-cyclopropylcarbamoyl)pyridinium]acetyl}-7-oxo-2,6-diazabicyclo[3.2.0]heptane-6-sulfonate, inner salt (109)

The titled compound was prepared following scheme 11 and in analogy to example 14 using (1S,5R)-7-oxo-2,6-diazabicyclo[3.2.0]heptane-6-sulfonic acid (compound H) and the commercially available nicotinoyl chloride hydrochloride and cyclopropylamine as starting materials.

1H-NMR (DMSO-d$_6$): 0.60 (m, 2H); 0.78 (m, 2H); 1.77 (m, 1H); 2.40 (m, 1H); 2.92 (m, 1H); 3.23 and 3.50 (2m, 1H); 4.01 and 4.10 (2m, 1H); 4.41 and 4.61 (2t, J=4.7, 1H); 5.20 and 5.29 (2d, J=4.3, 1H); 5.58-6.05 (AB part of a ABX system, the X part being in the $^{15}$N spectrum, 2H); 8.30 (m, 1H); 8.95 (m, 1H); 9.01-9.13 (m, 2H); 9.36 (m, 1H).

Example 23

(1S,5R)-2-{2-[4-(dimethylamino)pyridinium] acetyl}-7-oxo-2,6-diazabicyclo[3.2.0]heptane-6-sulfonate, inner salt (112)

The titled compound was prepared following scheme 11 and in analogy to example 14 using (1S,5R)-7-oxo-2,6-diazabicyclo[3.2.0]heptane-6-sulfonic acid (compound H) and the commercially available 4-(dimethylamino)pyridine as starting materials.

1H-NMR (DMSO-$d_6$): 1.22 (s, 3H); 1.26 (s, 3H); 1.74 (m, 1H); 2.38 (m, 1H); 3.20-3.50 (m, 1H); 3.98 and 4.08 (2dd, J=8.6 and 11.2, 1H); 4.38 and 4.48 (2t, J=4.7, 1H); 5.00-5.45 (m, 3H); 7.02 and 7.07 (2d, J=7.9, 2H); 8.11 and 8.16 (2d, J=7.9, 2H).

Example 24

2-(2-{3-[N-((3S)pyrrolidin-3-yl)carbamoyl] pyridinium}acetyl)(1S,5R)-7-oxo-2,6-diazabicyclo [3.2.0]heptane-6-sulfonate, inner salt (122)

Preparation of sodium (1S,5R)-2-(2-bromoacetyl)-7-oxo-2,6-diazabicyclo[3.2.0]heptane-6-sulfonate A solution of sulphur trioxide.DMF complex (4.92 g, 32.10 mmol, 1.5 eq) in DMF (10 mL) was added at 0° C. to a stirred solution of (5S,1R)-4-(2-bromoacetyl)-4,7-diazabicyclo[3.2.0]heptan-6-one (compound F, 5.25 g, 21.40 mmol, 1.0 eq) in DMF (110 mL). After 5 hours stirring at 0° C., the reaction mixture was concentrated. The remaining oil was dissolved in a minimum amount of $H_2O$ and the pH was adjusted to 6 with saturated $NaHCO_3$ solution. The mixture was then concentrated under reduced pressure to afford 8.3 g of the expected sodium (1S,5R)-2-(2-bromoacetyl)-7-oxo-2,6-diazabicyclo[3.2.0]heptane-6-sulfonate as a brown oil.

Preparation of tert-butyl (3S)-3-(3-pyridylcarbonylamino)pyrrolidinecarboxylate

Nicotinoyl chloride hydrochloride (286 mg, 1.61 mmol, 1.0 eq) was added at room temperature to a stirred solution of (S)-3-amino-1-N—BOC-pyrrolidine (300 mg, 1.61 mmol, 1.0 eq) in $CH_2Cl_2$ (9 mL), followed by triethylamine (337 µL, 2.42 mmol, 1.5 eq). After stirring overnight at room temperature, the reaction mixture was extracted and the organic layer was dried over $Na_2SO_4$, filtered and evaporated to afford 457 mg of the expected compound.

Preparation of 2-{2-[3-(N-{(3S)-1-[(tert-butyl)oxycarbonyl]pyrrolidin-3-yl}carbamoyl)pyridinium] acetyl}(1S,5R)-7-oxo-2,6-diazabicyclo[3.2.0]heptane-6-sulfonate, inner salt A solution of (1S,5R)-2-(2-bromoacetyl)-7-oxo-2,6-diazabicyclo[3.2.0]heptane-6-sulfonic acid (200 mg, 0.64 mmol, 1.0 eq) and tert-butyl (3S)-3-(3-pyridylcarbonylamino)pyrrolidinecarboxylate (149 mg, 0.51 mmol, 0.8 eq) in DMF (2 mL) was stirred at room temperature for 3 days. The reaction was monitored by LCMS. Then DMF was evaporated to afford 330 mg the expected crude product which was directly used in the next step.

Preparation of 2-(2-{(3-[N-((3S)pyrrolidin-3-yl)carbamoyl]pyridinium}acetyl)-(1S,5R)-7-oxo-2,6-diazabicyclo[3.2.0]heptane-6-sulfonate, inner salt (122)

A solution of 2-{2-[3-(N-{(3S)-1-[(tert-butyl)oxycarbonyl]pyrrolidin-3-yl}carbamoyl)pyridinium]acetyl}(1S,5R)-7-oxo-2,6-diazabicyclo[3.2.0]heptane-6-sulfonate, inner salt in DMF (4 mL) was cooled to 0° C. before the addition of trifluoroacetic acid (729 µL, 9.45 mmol, 15.0 eq). After stirring overnight at room temperature, the reaction mixture was concentrated and the crude was purified by preparative HPLC to afford 37 mg of the expected compound.

1H-NMR (DMSO-$d_6$): 1.80 (m, 1H); 2.05 (m, 1H); 2.23 (m, 1H); 2.40 (m, 1H); 3.33 (m, 5H); 4.01 and 4.10 (2m, 1H); 4.13 and 4.61 (2t, J=4.7, 1H); 4.56 (m, 1H); 5.18 and 5.30 (2d, J=4.1, 1H); 5.60-6.05 (AB part of an ABX system, the X part being in the $^{15}N$ spectrum, 2H); 8.35 (m, 1H); 9.07 (m, 3H); 9.38 (m, 1H); 9.44 (s, 1H).

Example 25

(1S,5R)-2-[2-(3-carbamoylpyridinium)acetyl]-7-oxo-2,6-diazabicyclo[3.2.0]heptane-6-sulfonate, inner salt (102)

The titled compound was prepared following scheme 11 and in analogy to example 24 using (SS,1R)-4-(2-bromoacetyl)-4,7-diazabicyclo[3.2.0]heptan-6-one (compound F) which was first sulfonated (J. Org. Chem. 1982, 5160) and the commercially available nicotinamide as starting materials.

1H-NMR (DMSO-$d_6$): 1.78 (m, 1H); 2.40 (m, 1H); 3.23 and 3.50 (2m, 1H); 4.03 and 4.13 (2dd, J=8.6 and 11.0, 1H); 4.42 and 4.63 (2t, J=4.7, 1H); 5.20 and 5.32 (2d, J=4.3, 1H); 5.55-6.05 (AB part of a ABX system, the X part being in the $^{15}N$ spectrum, 2H); 8.18 (d, J=3.7, 1H); 8.33 (q, J=6.2 and 7.9, 1H); 8.57 and 8.62 (2s, 1H); 9.02-9.12 (m, 2H); 9.42 (d, J=6.5, 1H).

Example 26

(1S,5R)-2-[2-(3,4-dicarbamoylpyridinium)acetyl]-7-oxo-2,6-diazabicyclo[3.2.0]heptane-6-sulfonate, inner salt (110)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3,4-pyridine dicarboxamide as starting materials.

1H-NMR (DMSO-$d_6$): 1.74 (m, 1H); 2.40 (m, 1H); 3.25 and 3.49 (2m, 1H); 4.03 and 4.11 (2m, 1H); 4.41 and 4.62 (2t, J=4.7, 1H); 5.22 and 5.29 (2d, J=4.3, 1H); 5.55-6.00 (AB part of a ABX system, the X part being in the $^{15}N$ spectrum, 2H); 8.04 (m, 1H); 8.14 (d, J=10.8, 1H); 8.24 (m, 2H); 8.45 (d, J=9.1, 1H); 9.10 (m, 1H); 9.24 (2s, 1H).

Example 27

(1S,5R)-2-{2-[4-(isopropyl)pyridinium]acetyl}-7-oxo-2,6-diazabicyclo[3.2.0]heptane-6-sulfonate, inner salt (113)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 4-isopropyl pyridine as starting materials.

1H-NMR (DMSO-$d_6$): 1.28 and 1.30 (2d, J=2.3, 6H); 1.77 (m, 1H); 2.42 (m, 1H); 3.10-3.55 (m, 2H); 4.00 and 4.10 (2m, 1H); 4.40 and 4.60 (2t, J=4.7, 1H); 5.19 and 5.29 (2d, J=4.2, 1H); 5.45-5.90 (AB part of a ABX system, the X part being in the $^{15}N$ spectrum, 2H); 8.11 (m, 2H); 8.81 (d, J=6.7, 1H); 8.87 (d, J=7.1, 1H).

Example 28

(1S,5R)-2-{2-[3-(methoxycarbonyl)-5-methylpyridinium]acetyl}-7-oxo-2,6-diazabicyclo[3.2.0]heptane-6-sulfonate, inner salt (114)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available methyl-5-methylnicotinate as starting materials.

1H-NMR (DMSO-$d_6$): 1.77 (m, 1H); 2.41 (m, 1H); 2.58 (d, J=5.9, 3H); 3.24 and 3.49 (2m, 1H); 3.98 (d, J=2.5, 3H); 4.02 and 4.12 (2m, 1H); 4.41 and 4.61 (2t, J=4.7, 1H); 5.20 and 5.29 (2d, J=4.3, 1H); 5.55-6.00 (AB part of a ABX system, the X part being in the $^{15}$N spectrum, 2H); 8.95 (m, 1H); 9.06 and 9.15 (2s, 1H); 9.41 and 9.45 (2s, 1H).

Example 29

(1S,5R)-2-{2-[3-(methoxycarbonyl)-2-methylpyridinium]acetyl}-7-oxo-2,6-diazabicyclo[3.2.0]heptane-6-sulfonate, inner salt (115)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 2-methyl nicotinic acid methyl ester as starting materials.

1H-NMR (DMSO-$d_6$): 1.82 (m, 1H); 2.40 (m, 1H); 2.81 (d, J=2.8, 3H); 3.29 and 3.57 (2m, 1H); 3.96 (s, 3H); 4.06 (m, 1H); 4.40 and 4.62 (2t, J=4.8, 1H); 5.20 and 5.34 (2d, J=4.3, 1H); 5.65-6.05 (AB part of a ABX system, the X part being in the $^{15}$N spectrum, 2H); 8.17 (m, 1H); 8.91 (m, 1H); 9.08 (m, 1H).

Example 30

(1S,5R)-2-{2-[3-(methoxycarbonyl)pyridinium]acetyl}-7-oxo-2,6-diazabicyclo[3.2.0]heptane-6-sulfonate, inner salt (116)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3-carboxypyridine methyl ester as starting materials.

1H-NMR (DMSO-$d_6$): 1.80 (m, 1H); 2.39 (m, 1H); 3.22 and 3.52 (2m, 1H); 3.98 (d, J=2.3, 3H); 4.01 and 4.12 (2m, 1H); 4.41 and 4.61 (2t, J=4.7, 1H); 5.20 and 5.29 (2d, J=4.2, 1H); 5.65-6.05 (AB part of a ABX system, the X part being in the $^{15}$N spectrum, 2H); 8.35 (m, 1H); 9.07 (m, 1H); 9.13 and 9.21 (2m, 1H); 9.57 and 9.62 (2s, 1H); 12.75 (br, 1H).

Example 31

(1S,5R)-7-oxo-2-[2-(4-propanoylpyridinium)acetyl]-2,6-diazabicyclo[3.2.0]heptane-6-sulfonate, inner salt (117)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 4-propionyl pyridine as starting materials.

1H-NMR (DMSO-$d_6$): 1.13 (dt, J=2.5 and 7.1, 3H); 1.80 (m, 1H); 2.41 (m, 1H); 3.15-3.55 (m, 3H); 4.02 and 4.11 (2dd, J=8.8 and 11.1, 1H); 4.41 and 4.61 (2t, J=4.7, 1H); 5.20 and 5.29 (2d, J=4.3, 1H); 5.60-6.05 (AB part of a ABX system, the X part being in the $^{15}$N spectrum, 2H); 8.53 and 8.56 (2d, J=7.1, 2H); 9.11 and 9.18 (2d, J=7.1, 2H).

Example 32

(1S,5R)-2-{2-[4-(aminothioxomethyl)pyridinium]acetyl}-7-oxo-2,6-diazabicyclo[3.2.0]heptane-6-sulfonate, inner salt (118)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 4-pyridine carbothioamide as starting materials.

1H-NMR (DMSO-$d_6$): 1.79 (m, 1H); 2.39 (m, 1H); 3.24 and 3.49 (2m, 1H); 4.00 and 4.10 (2m, 1H); 4.41 and 4.61 (2t, J=4.7, 1H); 5.21 and 5.28 (2d, J=4.3, 1H); 5.55-5.95 (AB part of a ABX system, the X part being in the $^{15}$N spectrum, 2H); 8.28 (dd, J=6.8 and 10.8, 2H); 8.96 and 9.02 (2d, J=6.8, 2H); 10.31 and 10.74 (2br, 2H); 12.7 (br, 1H).

Example 33

(1S,5R)-2-(2-{3-[(ethoxycarbonyl)methyl]pyridinium}acetyl)-7-oxo-2,6-diazabicyclo[3.2.0]heptane-6-sulfonate, inner salt (119)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available ethyl-3-pyridyl acetate as starting materials.

1H-NMR (DMSO-$d_6$): 1.22 (dt, J=0.9 and 7.1, 3H); 1.75 (m, 1H); 2.41 (m, 1H); 3.22 and 3.49 (2m, 1H); 4.05 (m, 3H); 4.15 (dq, J=0.9 and 7.1, 2H); 4.40 and 4.61 (2t, J=4.6, 1H); 5.20 and 5.30 (2d, J=4.3, 1H); 5.50-5.95 (AB part of a ABX system, the X part being in the $^{15}$N spectrum, 2H); 8.19 (m, 1H); 8.61 (m, 1H); 8.87 and 8.92 (2m, 1H); 8.89 and 8.97 (2s, 1H).

Example 34

(1S,5R)-7-oxo-2-{2-[3-(trifluoromethyl)pyridinium]acetyl}-2,6-diazabicyclo[3.2.0]heptane-6-sulfonate, inner salt (120)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3-(trifluoromethyl)pyridine as starting materials.

1H-NMR (DMSO-$d_6$): 1.80 (m, 1H); 2.40 (m, 1H); 3.24 and 3.51 (2m, 1H); 4.04 and 4.12 (2m, 1H); 4.42 and 4.62 (2t, J=4.7, 1H); 5.21 and 5.29 (2d, J=4.1, 1H); 5.65-6.05 (AB part of a ABX system, the X part being in the $^{15}$N spectrum, 2H);

8.47 (m, 1H); 9.17 (m, 1H); 9.24 and 9.30 (2d, J=6.2, 1H); 9.67 and 9.76 (2s, 1H); 12.7 (br, 1H).

Example 35

(1S,5R)-2-[2-(3,4-dimethylpyridinium)acetyl]-7-oxo-2,6-diazabicyclo[3.2.0]heptane-6-sulfonate, inner salt (121)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3,4-lutidine as starting materials.

1H-NMR (DMSO-$d_6$): 1.78 (m, 1H); 2.40 (d, J=3.7, 3H); 2.47 (m, 1H); 2.55 (d, J=3.6, 3H); 3.21 and 3.49 (2m, 1H); 4.06 (m, 1H); 4.40 and 4.60 (2t, J=4.7, 1H); 5.20 and 5.28 (2d, L=4.3, 1H); 5.40-5.85 (AB part of a ABX system, the X part being in the $^{15}$N spectrum, 2H); 7.97 (m, 1H); 8.70 (m, 2H).

Example 36

(1S,5R)-7-oxo-2-{2-[3-benzylpyridinium]acetyl}-2,6-diazabicyclo[3.2.0]heptane-6-sulfonate, inner salt (123)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3-benzylpyridine as starting materials.

1H-NMR (DMSO-$d_6$): 1.78 (m, 1H); 2.40 (m, 1H); 3.21 and 3.41 (2m, 1H); 4.01 and 4.10 (2m, 1H); 4.21 (d, J=7.3, 2H); 4.40 and 4.60 (2t, J=4.7, 1H); 5.20 and 5.28 (2d, J=4.2, 1H); 5.50-5.95 (AB part of a ABX system, the X part being in the $^{15}$N spectrum, 2H); 7.31 (m, 5H); 8.12 (m, 1H); 8.55 (t, J=7.6, 1H); 8.80 and 8.85 (2d, J=6.3, 1H); 8.90 and 9.00 (2s, 1H).

Example 37

(1S,5R)-7-oxo-2-[2-(3-phenylpyridinium)acetyl]-2,6-diazabicyclo[3.2.0]heptane-6-sulfonate, inner salt (124)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3-phenyl pyridine as starting materials.

1H-NMR (DMSO-$d_6$): 1.80 (m, 1H); 2.40 (m, 1H); 3.23 and 3.51 (2m, 1H); 4.10 (m, 1H); 4.42 and 4.62 (2t, J=4.7, 1H); 5.21 and 5.33 (2d, J=4.2, 1H); 5.60-6.00 (AB part of a ABX system, the X part being in the $^{15}$N spectrum, 2H); 7.62 (m, 3H); 7.88 (m, 2H); 8.28 (m, 1H); 8.93 (2d, J=6.3, 1H); 8.99 (m, 1H); 9.41 and 9.48 (2s, 1H).

Example 38

2-(2-{3-[N-((3R)pyrrolidin-3-yl)carbamoyl]pyridinium}acetyl)(1S,5R)-7-oxo-2,6-diazabicyclo[3.2.0]heptane-6-sulfonate, inner salt (125)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available nicotinoyl chloride hydrochloride and (R)-3-amino-1-N—BOC-pyrrolidine as starting materials.

+ESI-MS spectrum: m/z: 423 [M]$^+$.

Example 39

(1S,5R)-2-[2-(4-amino-3-carbamoylpyridinium)acetyl]-7-oxo-2,6-diazabicyclo[3.2.0]heptane-6-sulfonate, inner salt (126)

The titled compound was prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and a the commercially available 4-amino-3-pyridinecarboxamide as starting materials.

1H-NMR (DMSO-$d_6$): 1.75 (m, 1H); 2.40 (m, 1H); 3.22 and 3.45 (2m, 1H); 4.01 and 4.10 (2dd, J=8.6 and 11.3, 1H); 4.40 and 4.60 (2t, J=4.8, 1H); 4.95-5.50 (m, 3H); 7.03 (dd, J=7.4 and 9.4, 1H); 7.83 (br, 1H); 8.05 (m, 1H); 8.15 (br, 1H); 8.65 (m, 1H); 8.99 and 9.04 (2br, 2H).

Example 40

(1S,5R)-2-[2-(3-carbamoyl-5-methylpyridinium)acetyl]-7-oxo-2,6-diazabicyclo[3.2.0]heptane-6-sulfonate, inner salt (127)

The titled compound has been prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 5-methyl nicotinamide as starting materials.

1H-NMR (DMSO-$d_6$): 1.78 (m, 1H); 2.39 (m, 1H); 2.54 (m, 3H); 3.23 and 3.49 (2m, 1H); 4.05 (m, 1H); 4.41 and 4.61 (2t, J=4.7, 1H); 5.20 and 5.29 (2d, J=4.3, 1H); 5.50-6.00 (AB part of a ABX system, the X part being in the $^{15}$N spectrum, 2H); 8.52 (d, J=16.0, 1H); 8.89 (d, L=7.2, 1H); 8.95 and 9.04 (2s, 1H); 9.24 (m, 2H); 12.6 (br, 1H).

Example 41

(1S,5R)-2-{2-[3-(aminocarbonylamino)pyridinium]acetyl}-7-oxo-2,6-diazabicyclo[3.2.0]heptane-6-sulfonate, inner salt (128)

The titled compound has been prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and 3-pyridylcarbamide.

1H-NMR (DMSO-$d_6$): 1.78 (m, 1H); 2.40 (m, 1H); 3.23 and 3.49 (2m, 1H); 3.98 and 4.10 (2m, 1H); 4.40 and 4.59 (2t, J=4.7, 1H); 5.20 and 5.28 (2d, J=4.2, 1H); 5.40-6.00 (AB part of a ABX system, the X part being in the $^{15}$N spectrum, 2H); 6.51 (br, 2H); 8.00 (m, 1H); 8.28 (m, 1H); 8.49 (m, 1H); 9.20 (m, 1H); 9.67 (d, J=12.2, 1H).

3-Pyridylcarbamide was prepared according to the procedure described in Heterocycles 1983, 1899.

Example 42

(1S,5R)-2-[2-(5-amino-3-carbamoylpyridinium) acetyl]-7-oxo-2,6-diazabicyclo[3.2.0]heptane-6-sulfonate, inner salt (129)

The titled compound has been prepared following scheme 11 and in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 5-amino-3-pyridinecarboxamide as starting materials.

1H-NMR (DMSO-$d_6$): 1.78 (m, 1H); 2.41 (m, 1H); 3.22 and 3.46 (2m, 1H); 3.98 and 4.09 (2m, 1H); 4.40 and 4.59 (2t, J=4.6, 1H); 5.20 and 5.26 (2d, J=4.1, 1H); 5.40-5.85 (AB part of a ABX system, the X part being in the $^{15}$N spectrum, 2H); 6.88 (d, J=11.5, 2H); 7.95 (m, 1H); 8.07 (m, 2H); 8.41 (m, 2H).

Example 43

(1S,5R)-2-[N-(4-{[(2-aminoethyl)amino] carbonylamino}phenyl)carbamoyl]-7-oxo-2,6-diazabicyclo[3.2.0]heptane-6-sulfonic acid (324)

Preparation of (tert-butoxy)-N-{4-[(fluoren-9-ylmethoxy)carbonylamino]phenyl}carboxamide Triethylamine (7.36 mL, 52.82 mmol, 1.1 eq) was added at 0° C. to a stirred solution of N—BOC-1,4-phenylene diamine (10.00 g, 48.02 mmol, 1.0 eq) in CH$_3$CN (240 mL), followed by 9-fluorenylmethyloxycarbonyl chloride (14.90 g, 57.62 mmol, 1.2 eq). The resulting mixture was allowed to come at room temperature. After 4 hours stirring at room temperature, the reaction mixture was filtered to afford 20.60 g of the crude expected product as a white powder which was used in the next step without any further purification.

1H-NMR (DMSO-$d_6$): 1.46 (s, 9H); 4.29 (t, J=6.6, 1H); 4.44 (d, J=6.3, 2H); 7.30-7.45 (m, 8H); 7.75 (d, J=7.4, 2H); 7.91 (d, J=7.4, 2H); 9.22 (br, 1H); 9.59 (br, 1H)

Preparation of N-(4-aminophenyl)(fluoren-9-ylmethoxy)carboxamide

TFA (55.30 mL, 717.76 mmol, 15.0 eq) was added at 0° C. to a stirred solution of (tert-butoxy)-N-{4-[(fluoren-9-ylmethoxy)carbonylamino]phenyl}carboxamide (20.60 g, 47.85 mmol, 1.0 eq) in CH$_2$Cl$_2$ (900 mL). The resulting solution was allowed to come at room temperature. After stirring overnight at room temperature, the reaction mixture was concentrated to dryness and the residue was triturated in water. Then the mixture was filtered to afford 15.80 g of the expected crude product as a white powder.

1H-NMR (DMSO-$d_6$): 4.30 (t, J=6.4, 1H); 4.49 (d, J=6.4, 2H); 7.06 (d, J=7.7, 2H); 7.40 (m, 6H); 7.74 (d, J=7.4, 2H); 7.91 (d, J=7.4, 2H); 8.95 (br, 2H); 9.73 (br, 1H).

Preparation of N-{4-[(2,5-dioxoazolidinyloxy)carbonylamino]phenyl}(fluoren-9-ylmethoxy)carboxamide N,N'-Disuccinimidylcarbonate (16.20 g, 63.26 mmol, 1.1 eq) was added at room temperature to a stirred solution of N-(4-aminophenyl)(fluoren-9-ylmethoxy)carboxamide (20.00 g, 60.53 mmol, 1.0 eq) in CH$_3$CN (1100 mL). After stirring overnight at room temperature, the reaction mixture was filtered to afford 28.50 g of the expected crude product as a white powder. 1H-NMR (DMSO-$d_6$): 2.83 (br, 4H); 4.31 (t, J=6.4, 1H); 4.48 (m, 2H); 7.20-7.50 (m, 8H); 7.5 (d, j=7.4, 2H); 7.91 (d, J=7.4, 2H); 9.72 (br, 1H); 10.67 (br, 1H).

Preparation of N-{4-[({2-[(tert-butoxy)carbonylamino]ethyl}amino)carbonylamino]phenyl}(fluoren-9-ylmethoxy)carboxamide A solution of N-{4-[(2,5-dioxoazolidinyloxy)carbonylamino]phenyl}(fluoren-9-ylmethoxy)carboxamide (16.10 g, 34.15 mmol, 1.0 eq) in H$_2$O/CH$_3$CN (1/1, v/v, 360 mL) was reacted at room temperature with NaHCO$_3$ (2.86 g, 34.15 mmol, 1.0 eq) and N—BOC-ethylene diamine (5.47 g, 34.15 mmol, 1.0 eq). After stirring overnight at room temperature, the reaction mixture was filtered to afford 16.36 g of the expected crude product as a white solid.

1H-NMR (DMSO-d6): 1.37 (s, 9H); 2.98 (m, 2H); 3.11 (m, 2H); 4.29 (t, J=6.4, 1H); 4.44 (d, J=6.4, 2H); 6.10 (m, 1H); 6.85 (m, 1H); 7.30-7.50 (m, 8H); 7.74 (d, J=7.4, 2H); 7.90 (d, J=7.4, 2H); 8.40 (s, 1H); 9.53 (br, 1H).

Preparation of N-(4-aminophenyl)({2-[(tert-butoxy)carbonylamino]ethyl}amino) carboxamide Piperidine (9.68 mL, 97.75 mmol, 5.0 eq) was added at room temperature to a stirred solution of N-{4-[({2-[(tert-butoxy)carbonylamino]ethyl}amino)carbonylamino]phenyl}(fluoren-9-ylmethoxy)carboxamide (10.10 g, 19.55 mmol, 1.0 eq) in DMF (140 mL). After 2 hours stirring at room temperature, water was added to the reaction mixture and precipitation α-cured. The resulting mixture was filtered, and the liquid phase was concentrated to afford 6.75 g of the expected product as an orange oil:

1H-NMR (DMSO-$d_6$): 1.37 (s, 9H); 2.98 (m, 2H); 3.11 (m, 2H); 4.69 (s, 2H); 6.00 (t, J=5.5, 1H); 6.44 (d, J=8.6, 2H); 6.81 (t, J=5.3, 1H); 6.97 (d, J=8.6, 2H); 8.00 (s, 1H).

Preparation of ({2-[(tert-butoxy)carbonylamino]ethyl}amino)-N-{4-[(2,5-dioxoazolidinyloxy)carbonylamino]phenyl}carboxamide N,N'-Disuccinimidylcarbonate (5.49 g, 21.44 mmol, 1.1 eq) was added at room temperature to a stirred solution of N-(4-aminophenyl)({2-[(tert-butoxy)carbonylamino]ethyl}amino)carboxamide (6.75 g, 19.49 mmol, 1.0 eq) in CH$_3$CN (350 mL). After stirring overnight at room temperature, the reaction mixture was filtered and to afford 9.70 g of the expected crude product as a light brown solid.

1H-NMR (DMSO-d6): 1.37 (s, 9H); 2.82 (br, 4H); 2.99 (m, 2H); 3.11 (m, 2H); 6.12 (t, J=5.2, 1H); 6.85 (t, J=5.5, 1H); 7.27 (d, J=8.9, 2H); 7.36 (d, J=8.9, 2H); 7.95 (s, 1H); 8.53 (s, 1H).

Preparation of [(2-aminoethyl)amino]-N-{4-[(2,5-dioxoazolidinyloxy) carbonylamino] phenyl}carboxamide TFA (11.59 mL, 150.54 mmol, 5.0 eq) was added at room temperature to a stirred suspension of ({2-[(tert-butoxy)carbonylamino]ethyl}amino)-N-{4-[(2,5-dioxoazolidinyloxy)carbonylamino]phenyl}carboxamide (13.8 g, 30.11 mmol, 1.0 eq) in CH$_2$Cl$_2$ (165 mL). After stirring overnight at room temperature, solvent was evaporated and the crude product was triturated with Et$_2$O to afford 14.2 g of the expected crude product as a beige solid and as the trifluoroacetic acid salt.

1H-NMR (DMSO-d$_6$): 2.82 (br, 4H); 2.88 (m, 2H); 3.30 (m, 2H); 6.51 (t, J=5.6, 1H); 7.30 (d, J=8.9, 2H); 7.40 (d, J=8.9, 2H); 7.77 (br, 3H); 8.85 (s, 1H); 10.61 (s, 1H)

Preparation of (1S,5R)-2-[N-(4-{[(2-aminoethyl)amino]carbonylamino}phenyl) carbamoyl]-7-oxo-2,6-diazabicyclo[3.2.0]heptane-6-sulfonic acid (324)

(1S,5R)-7-oxo-2,6-diazabicyclo[3.2.0]heptane-6-sulfonic acid (compound H, 2.0 g, 10.41 mmol, 1.0 eq) was dissolved in H$_2$O (12.5 mL). Then CH$_3$CN (100 mL) was added at room temperature to the solution, followed by NaHCO$_3$ (1.57 g, 18.73 mmol, 1.8 eq) and [(2-aminoethyl)amino]-N-{4-[(2,5-dioxoazolidinyloxy)carbonylamino]phenyl}carboxamide (6.89 g, 14.57 mmol, 1.4 eq). After stirring overnight at room temperature, the reaction mixture was filtered to afford 3.27 g of the expected (1S,5R)-2-[N-(4-{[(2-aminoethyl)amino]carbonylamino}phenyl)carbamoyl]-7-oxo-2,6-diazabicyclo[3.2.0]heptane-6-sulfonic acid as a white solid.

1H-NMR (DMSO-d$_6$): 1.65 (m, 1H); 2.30 (dd, J=5.8 and 13.5, 1H); 2.90 (m, 2H); 3.18 (m, 1H); 3.30 (m, 2H); 3.98 (m, 1H); 4.41 (t, J=4.7, 1H); 5.22 (d, J=4.3, 1H); 6.23 (t, J=5.7, 1H); 7.28 (d, J=8.2, 2H); 7.33 (d, J=8.2, 2H); 7.65 (br, 3H); 8.38 (s, 1H); 8.53 (s, 1H).

Example 44

Sodium (1S,5R)-2-[N-(3,4-dihydroxyphenyl)carbamoyl]-7-oxo-2,6-diazabicyclo[3.2.0]heptane-6-sulfonate (306)

The titled compound was prepared following scheme 12 and in analogy to example 43 using (1S,5R)-7-oxo-2,6-diazabicyclo[3.2.0]heptane-6-sulfonic acid (compound H) and the commercially available 4-amino-1,2-benzenediol as starting materials.

1H-NMR (DMSO-d$_6$): 1.64 (m, 1H); 2.29 (dd, J=5.8 and 13.6, 1H); 3.13 (m, 1H); 3.93 (dd, J=8.3 and 11.0, 1H); 4.37 (t, J=4.8, 1H); 5.20 (d, J=4.3, 1H); 6.50-6.70 (m, 2H); 6.97 (m, 1H); 7.84 and 8.15 (2s, 1H); 8.35 and 8.43 (2s, 1H); 8.77 and 8.82 (2s, 1H).

Example 45

Sodium (1S,5R)-2-{N-[3-(acetylamino)phenyl]carbamoyl}-7-oxo-2,6-diazabicyclo[3.2.0]heptane-6-sulfonate (307)

The titled compound was prepared following scheme 12 and in analogy to example 43 using (1S,5R)-7-oxo-2,6-diazabicyclo[3.2.0]heptane-6-sulfonic acid (compound H) and the commercially available 1-acetamido-3-aminobenzene as starting materials.

1H-NMR (DMSO-d$_6$): 1.66 (m, 1H); 2.02 (s, 3H); 2.31 (dd, J=5.8 and 13.6, 1H); 3.17 (m, 1H); 3.98 (dd, J=8.3 and 11.0, 1H); 4.40 (t, J=4.8, 1H); 5.27 (d, J=4.3, 1H); 7.05-7.25 (m, 3H); 7.64 (m, 1H); 8.54 (s, 1H); 9.86 (s, 1H).

Example 46

Sodium (1S,5R)-7-oxo-2-[N-(3-sulfamoylphenyl)carbamoyl]-2,6-diazabicyclo[3.2.0]heptane-6-sulfonate (308)

The titled compound was prepared following scheme 12 and in analogy to example 43 using (1S,5R)-7-oxo-2,6-diazabicyclo[3.2.0]heptane-6-sulfonic acid (compound H) and the commercially available 3-aminobenzene sulfonamide as starting materials.

1H-NMR (DMSO-d$_6$): 1.68 (m, 1H); 2.32 (dd, J=5.8 and 13.5, 1H); 3.21 (m, 1H); 4.02 (dd, J=8.5 and 11.2, 1H); 4.43 (t, J=4.7, 1H); 5.28 (d, J=4.2, 1H); 7.31 (br, 2H); 7.38-7.46 (m, 2H); 7.72 and 7.74 (2t, J=1.9, 1H); 8.05 (t, J=1.7, 1H); 8.89 (br, 1H).

Example 47

Sodium (1S,5R)-2-{N-[4-(dimethylamino)phenyl]carbamoyl}-7-oxo-2,6-diazabicyclo[3.2.0]heptane-6-sulfonate (309)

The titled compound was prepared following scheme 12 and in analogy to example 43 using (1S,5R)-7-oxo-2,6-diazabicyclo[3.2.0]heptane-6-sulfonic acid (compound H) and the commercially available 4-(dimethylamino)aniline as starting materials.

+ESI-MS spectrum: m/z: 354 [M+H]$^+$

Example 48

Sodium (1S,5R)-2-[N-(4-{N-[2-(dimethylamino)ethyl]carbamoyl}phenyl)carbamoyl]-7-oxo-2,6-diazabicyclo[3.2.0]heptane-6-sulfonate (310)

The titled compound was prepared following scheme 12 and in analogy to example 43 using (1S,5R)-7-oxo-2,6-diazabicyclo[3.2.0]heptane-6-sulfonic acid (compound H) and the commercially available 4-aminobenzoic acid and 2-(dimethylamino)ethylamine as starting materials.

+ESI-MS spectrum: m/z: 425 [M+H].

Example 49

Sodium (1SR)-2-(N-{4-[N-(carbamoylmethyl)carbamoyl]phenyl}carbamoyl)-7-oxo-2,6-diazabicyclo[3.2.0]heptane-6-sulfonate (312)

The titled compound was prepared following scheme 12 and in analogy to example 43 using (1S,5R)-7-oxo-2,6-diazabicyclo[3.2.0]heptane-6-sulfonic acid (compound H) and the commercially available 4-aminobenzoic acid and glycinamide hydrochloride as starting materials.

1H-NMR (DMSO-d$_6$): 1.68 (m, 1H); 2.32 (dd, J=5.8 and 13.5, 1H); 3.21 (m, 1H); 3.78 (d, J=5.7, 2H); 4.02 (dd, J=8.3 and 11.1, 1H); 4.42 (t, J=4.7, 1H); 5.28 (d, J=4.6, 1H); 7.02 (br, 1H); 7.23 (br, 1H); 7.58 (d, J=9.1, 2H); 7.79 (d, J=9.1, 2H); 8.50 (t, J=5.8, 1H); 8.78 (s, 1H).

Example 50

Sodium (1S,5R)-2-[N-(3-(1,3-oxazol-5-yl)phenyl)carbamoyl]-7-oxo-2,6-diazabicyclo[3.2.0]heptane-6-sulfonate (318)

The titled compound was prepared following scheme 12 and in analogy to example 43 using (1S,5R)-7-oxo-2,6-diazabicyclo[3.2.0]heptane-6-sulfonic acid (compound H) and the commercially available 3-(1,3-oxazol-5-yl)aniline as starting materials.

1H-NMR (DMSO-d$_6$): 1.68 (m, 1H); 2.33 (dd, J=5.8 and 13.7, 1H); 3.21 (m, 1H); 4.02 (dd, J=8.1 and 11.0, 1H); 4.42

(t, J=4.7, 1H); 5.27 (d, J=4.3, 1H); 7.30-7.40 (m, 2H); 7.52 (m, 1H); 7.60 (S, 1H); 7.91 (s, 1H); 8.44 (S, 1H); 8.72 (br, 1H).

Example 51

Sodium (1S,5R)-7-oxo-2-[N-(2-oxo(3-hydrobenzimidazol-5-yl))carbamoyl]-2,6-diazabicyclo[3.2.0]heptane-6-sulfonate (319)

The titled compound was prepared following scheme 12 and in analogy to example 43 using (1S,5R)-7-oxo-2,6-diazabicyclo[3.2.0]heptane-6-sulfonic acid (compound H) and the commercially available 5(6)-aminobenzoimidazolone as starting materials.

1H-NMR (DMSO-$d_6$): 1.65 (m, 1H); 2.30 (dd, J=5.8 and 13.5, 1H); 3.17 (m, 1H); 3.96 (dd, J=8.3 and 11.0, 1H); 4.39 (t, J=4.7, 1H); 5.22 (d, J=4.3, 1H); 6.78 (m, 1H); 6.95 (m, 1H); 7.22 (m, 1H); 8.07 and 8.37 (2s, 1H); 10.34 and 10.39 (2s, 1H); 10.46 and 10.50 (2s, 1H).

Example 52

Sodium (1S,5R)-2-{N-[3-(ethoxycarbonyl)phenyl]carbamoyl}-7-oxo-2,6-diazabicyclo[3.2.0]heptane-6-sulfonate (320)

The titled compound was prepared following scheme 12 and in analogy to example 43 using (1S,5R)-7-oxo-2,6-diazabicyclo[3.2.0]heptane-6-sulfonic acid (compound H) and the commercially available 3-aminobenzoic acid ethyl ester as starting materials.

1H-NMR (DMSO-$d_6$): 1.32 (t, J=7.1, 3H); 1.68 (m, 1H); 2.32 (dd, J=5.8 and 13.5, 1H); 3.20 (m, 1H); 4.02 (dd, J=8.3 and 11.0, 1H); 4.31 (q, J=7.1, 2H); 4.42 (t, J=4.7, 1H); 5.27 (d, J=4.5, 1H); 7.39 (t, J=8.0, 1H); 7.56 (2dd, J=1.2 and 1.6, 1H); 7.82 (m, 1H); 8.14 (t, J=1.9, 1H); 8.81 (br, 1H).

Example 53

Sodium (1S,5R)-2-{N-[3-(hydroxymethyl)phenyl]carbamoyl}-7-oxo-2,6-diazabicyclo[3.2.0]heptane-6-sulfonate (321)

The titled compound was prepared following scheme 12 and in analogy to example 43 using (1S,5R)-7-oxo-2,6-diazabicyclo[3.2.0]heptane-6-sulfonic acid (compound H) and the commercially available 3-(hydroxymethyl)aniline as starting materials.

1H-NMR (DMSO-$d_6$): 1.67 (m, 1H); 2.31 (dd, J=5.8 and 13.5, 1H); 3.18 (m, 1H); 3.99 (dd, J=8.3 and 11.4, 1H); 4.41 (t, J=4.7, 1H); 4.45 (d, J=5.8, 2H); 5.15 (t, J=5.6, 1H); 5.27 (d, J=4.3, 1H); 6.90 (m, 1H); 7.18 (t, J=7.8, 1H); 7.39 (m, 1H); 7.45 (m, 1H); 8.52 (br, 1H).

Example 54

(1S,5R)-2-{N-[4-({[2-(2-aminoethoxy)ethyl]amino}carbonylamino)phenyl]carbamoyl}-7-oxo-2,6-diazabicyclo[3.2.0]heptane-6-sulfonic acid (323)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine and 2,2'-oxydiethylamine dihydrochloride (Eur. J. Org. Chem. 2002, 3004) as starting materials.

1H-NMR (DMSO-$d_6$): 1.65 (m, 1H); 2.30 (dd, J=5.8 and 13.5, 1H); 2.99 (m, 2H); 3.16 (m, 1H); 3.29 (m, 2H); 3.49 (t, J=5.7, 2H); 3.60 (t, J=5.2, 2H); 3.95 (m, 1H); 4.39 (t, J=4.7, 1H); 5.20 (d, J=4.3, 1H); 6.13 (t, J=5.7, 1H); 7.24 (d, J=8.2, 2H); 7.31 (d, J=8.2, 2H); 7.73 (br, 3H); 8.35 (s, 1H); 8.37 (s, 1H).

Example 55

(1S,5R)-7-oxo-2-(N-{4-[(4-piperidylamino)carbonylamino]phenyl}carbamoyl)-2,6-diazabicyclo[3.2.0]heptane-6-sulfonic acid (325)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine and 1-BOC-4-amino-piperidine hydrochloride as starting materials.

1H-NMR (DMSO-$d_6$): 1.52 (m, 2H); 1.68 (m, 1H); 1.98 (m, 2H); 2.31 (dd, J=6.0 and 13.6, 1H); 3.00 (m, 2H); 3.17 (m, 1H); 3.23 (m, 3H); 3.72 (m, 1H); 3.97 (dd, J=8.3 and 11.0, 1H); 4.40 (t, J=4.8, 1H); 5.21 (d, J=4.2, 1H); 6.28 (d, J=7.5, 1H); 7.23 (d, J=9.2, 2H); 7.32 (d, J=9.2, 2H); 8.12 (s, 1H); 8.28 (br, 1H); 8.38 (s, 1H).

Example 56

(1S,5R)-7-oxo-2-{N-[4-(piperazinylcarbonylamino)phenyl]carbamoyl}-2,6-diazabicyclo[3.2.0]heptane-6-sulfonic acid (326)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine and 1-BOC-piperazine as starting materials.

1H-NMR (DMSO-$d_6$): 1.65 (m, 1H); 2.32 (dd, J=5.7 and 13.6, 1H); 3.13 (m, 4H); 3.19 (m, 1H); 3.62 (m, 4H); 3.97 (dd, J=8.3 and 11.2, 1H); 4.40 (t, J=4.7, 1H); 5.31 (d, J=4.3, 1H); 7.28 (d, J=9.2, 2H); 7.36 (d, J=9.2, 2H); 8.42 (S, 1H); 8.58 (s, 1H); 8.63 (br, 1H).

Example 57

Sodium (1S,5R)-2-[N-(4-aminophenyl)carbamoyl]-7-oxo-2,6-diazabicyclo[3.2.0]heptane-6-sulfonate (327)

The titled compound was prepared following scheme 12 and in analogy to example 43 using (1S,5R)-7-oxo-2,6-diazabicyclo[3.2.0]heptane-6-sulfonic acid (compound H) and the commercially available N—BOC-1,4-phenylene diamine as starting materials.

+ESI-MS spectrum: m/z: 326 [M+H]$^+$.

Example 58

Sodium (1S,5R)-2-[N-(2-carbamoylphenyl)carbamoyl]-7-oxo-2,6-diazabicyclo[3.2.0]heptane-6-sulfonate (328)

The titled compound was prepared following scheme 12 and in analogy to example 43 using (1S,5R)-7-oxo-2,6-diazabicyclo[3.2.0]heptane-6-sulfonic acid (compound H) and the commercially available 2-aminobenzamide as starting materials.

1H-NMR (DMSO-$d_6$): 1.67 (m, 1H); 2.36 (dd, J=6.0 and 13.8, 1H); 3.23 (m, 1H); 3.97 (m, 1H); 4.42 (t, J=4.7, 1H); 5.24 (d, J=4.2, 1H); 7.00 (m, 1H); 7.45 (m, 1H); 7.72 (br, 1H); 7.79 (dd, J=1.2 and 7.9, 1H); 7.91 (s, 1H); 8.28 (br, 1H); 8.37 (dd, J=1.2 and 8.4, 1H).

Example 59

Sodium (1S,5R)-7-oxo-2-[N-(4-{2-[(phenyl-methoxy)carbonylamino]acetylamino}phenyl)carbamoyl]-2,6-diazabicyclo[3.2.0]heptane-6-sulfonate (329)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine and N-carbobenzoxyglycine as starting materials.
1H-NMR (DMSO-$d_6$): 1.66 (m, 1H); 2.31 (m, 1H); 3.18 (m, 1H); 3.78 (d, J=6.1, 2H); 3.98 (dd, J=8.0 and 11.1, 1H); 4.40 (t, J=4.8, 1H); 5.03 (s, 2H); 5.23 (d, J=4.5, 1H); 7.22-7.58 (m, 10H); 8.49 (s, 1H); 9.83 (s, 1H).

Example 60

(1S,5R)-2-[N-(4-{[(2-morpholin-4-ylethyl)amino]carbonylamino}phenyl)carbamoyl]-7-oxo-2,6-diazabicyclo[3.2.0]heptane-6-sulfonic acid (330)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine and N-(2-aminoethyl)morpholine as starting materials.
1H-NMR (DMSO-$d_6$): 1.67 (m, 1H); 2.31 (dd, J=6.1 and 13.7, 1H); 3.00-3.25 (m, 5H); 3.40-3.75 (m, 6H); 3.97 (m, 3H); 4.41 (t, J=4.7, 1H); 5.22 (d, J=4.2, 1H); 6.28 (br, 1H); 7.28 (d, J=9.2, 2H); 7.33 (d, J=9.2, 2H); 8.39 (s, 1H); 8.50 (s, 1H); 9.47 (br, 1H).

Example 61

(1S,5R)-2-[N-(4-{[(2-{[(2-morpholin-4-ylethyl)amino]carbonylamino}ethyl)amino]carbonylamino}phenyl) carbamoyl]-7-oxo-2,6-diazabicyclo[3.2.0]heptane-6-sulfonic acid (331)

The titled compound was prepared following scheme 12 and in analogy to example 43 using (1S,5R)-7-oxo-2,6-diazabicyclo[3.2.0]heptane-6-sulfonic acid (compound H) and the commercially available 1,4-benzene diamine, N-(2-aminoethyl)morpholine and ethylenediamine as starting materials.
1H-NMR (DMSO-$d_6$): 1.66 (m, 1H); 2.31 (dd, J=6.1 and 13.7, 1H); 3.00-3.22 (m, 11H); 3.49 (m, 2H); 3.61 (m, 2H); 3.96 (m, 3H); 4.39 (t, J=4.7, 1H); 5.22 (d, J=4.5, 1H); 6.11 (t, J=5.8, 1H); 6.32 (m, 2H); 7.24 (d, J=9.1, 2H); 7.33 (d, J=9.1, 2H); 8.38 (d, J=4.4, 1H); 9.53 (br, 1H).

Example 62

(1S,5R)-2-(N-{4-[N-(2-aminoethyl)carbamoyl]phenyl}carbamoyl)-7-oxo-2,6-diazabicyclo[3.2.0]heptane-6-sulfonic acid (332)

The titled compound was prepared following scheme 12 and in analogy to example 43 using (1S,5R)-7-oxo-2,6-diazabicyclo[3.2.0]heptane-6-sulfonic acid (compound H) and the commercially available 4-aminobenzamide and 2-bromoethanamine as starting materials.
1H-NMR (DMSO-$d_6$): 1.69 (m, 1H); 2.33 (dd, J=5.8 and 13.7, 1H); 2.97 (m, 2H); 3.22 (m, 1H); 3.48 (m, 2H); 4.01 (dd, J=8.2 and 11.0, 1H); 4.43 (t, J=4.7, 1H); 5.27 (d, J=4.5, 1H); 7.61 (d, J=9.1, 2H); 7.75 (m, 5H); 8.43 (m, 1H); 8.81 (s, 1H).

Example 63

Sodium (1S,5R)-2-(N-{4-[(tert-butoxy)carbonylamino]phenyl}carbamoyl)-7-oxo-2,6-diazabicyclo[3.2.0]heptane-6-sulfonate (333)

The titled compound was prepared following scheme 12 and in analogy to example 43 using (1S,5R)-7-oxo-2,6-diazabicyclo[3.2.0]heptane-6-sulfonic acid (compound H) and the commercially available N—BOC-1,4-benzene diamine as starting materials.
1H-NMR (DMSO-$d_6$): 1.46 (s, 9H); 1.64 (m, 1H); 2.30 (dd, J=5.8 and 13.5, 1H); 3.16 (m, 1H); 3.97 (dd, J=8.5 and 11.3, 1H); 4.39 (t, J=4.8, 1H); 5.22 (d, J=4.3, 1H); 7.25-7.35 (m, 4H); 8.41 (s, 1H); 9.17 (s, 1H).

Example 64

Sodium (1S,5R)-2-{N-[(3,4-dihydroxyphenyl)methyl]carbamoyl}-7-oxo-2,6-diazabicyclo[3.2.0]heptane-6-sulfonate (303)

The titled compound was prepared following scheme 12 and in analogy to example 43 using (1S,5R)-7-oxo-2,6-diazabicyclo[3.2.0]heptane-6-sulfonic acid (compound H) and commercially available 3,4-dihydroxybenzylamine.
−ESI-MS spectrum: m/z: 356 [M−H]$^+$.

Example 65

(1S,5R)-2-{N-[4-(morpholin-4-ylmethyl)phenyl]carbamoyl}-7-oxo-2,6-diazabicyclo[3.2.0]heptane-6-sulfonic acid (334).

The titled compound has been prepared following scheme 12 and in analogy to example 43 using (1S,5R)-7-oxo-2,6-diazabicyclo[3.2.0]heptane-6-sulfonic acid (compound H) and the commercially available 4-(morpholinomethyl)aniline as starting materials.
1H-NMR (DMSO-$d_6$): 1.67 (m, 1H); 2.30 (dd, J=5.8 and 13.6, 1H); 3.12 (m, 2H); 3.25 (m, 3H); 3.60 (t, J=11.8, 2H); 3.97 (m, 3H); 4.26 (br, 2H); 4.42 (t, J=4.7, 1H); 5.25 (d, J=4.3, 1H); 7.36 (d, J=8.2, 2H); 7.60 (d, J=8.2, 2H); 8.74 (br, 1H); 9.61 (br, 1H).

Example 66

(1S,5R)-2-[N-(4-morpholin-4-ylphenyl)carbamoyl]-7-oxo-2,6-diazabicyclo[3.2.0]heptane-6-sulfonic acid (335)

The titled compound has been prepared following scheme 12 and in analogy to example 43 using (1S,5R)-7-oxo-2,6-diazabicyclo[3.2.0]heptane-6-sulfonic acid (compound H) and the commercially available 4-morpholinoaniline as starting materials.
1H-NMR (DMSO-$d_6$): 1.67 (m, 1H); 2.32 (dd, J=5.8 and 13.6, 1H); 3.19 (m, 1H); 3.32 (br, 4H); 3.85 (br, 4H); 3.98 (m, 1H); 4.42 (t, J=4.7, 1H); 5.25 (d, J=4.3, 1H); 7.24 (br, 2H); 7.50 (d, J=8.6, 2H); 8.60 (br, 1H).

Example 67

(1S,5R)-2-[N-(3-morpholin-4-ylphenyl)carbamoyl]-7-oxo-2,6-diazabicyclo[3.2.0]heptane-6-sulfonic acid (336).

The titled compound has been prepared following scheme 12 and in analogy to example 43 using (1S,5R)-7-oxo-2,6-diazabicyclo[3.2.0]heptane-6-sulfonic acid (compound H) and the commercially available 3-morpholino-4-ylaniline as starting materials.
1H-NMR (DMSO-$d_6$): 1.67 (m, 1H); 2.32 (dd, J=5.8 and 13.6, 1H); 3.19 (m, 1H); 3.26 (br, 4H); 3.82 (br, 4H); 3.99 (m, 1H); 4.42 (t, J=4.7, 1H); 5.25 (d, J=4.3, 1H); 6.84 (d, J=7.5, 1H); 7.15 (d, j=8.1, 1H); 7.23 (t, J=8.1, 1H); 7.48 (br, 1H); 8.60 (br, 1H).

Example 68

(1S,5R)-7-oxo-2-{N-[3-(piperazinylmethyl)phenyl]carbamoyl}-2,6-diazabicyclo[3.2.0]heptane-6-sulfonic acid (337)

The titled compound has been prepared following scheme 12 and in analogy to example 43 using (1S,5R)-7-oxo-2,6-diazabicyclo[3.2.0]heptane-6-sulfonic acid (compound H) and the commercially available tert-butyl 4-(3-aminobenzyl)piperazine-1-carboxylate as starting materials. The final deprotection step, using trifluoroacetic acid, has been performed in analogy to example 1.
1H-NMR (DMSO-$d_6$): 1.67 (m, 1H); 2.32 (dd, J=5.8 and 13.6, 1H); 2.58 (br, 4H); 3.09 (br, 4H); 3.19 (m, 1H); 3.49 (br, 2H); 3.98 (m, 1H); 4.41 (t, J=4.7, 1H); 5.25 (d, J=4.3, 1H); 6.89 (d, J=7.5, 1H); 7.21 (t, J=8.1, 1H); 7.37 (t, J=8.1, 1H); 7.52 (br, 1H); 8.44 (br, 2H); 8.55 (br, 1H).

Example 69

2-[N-((3S)pyrrolidin-3-yl)carbamoyl](1S,5R)-7-oxo-2,6-diazabicyclo[3.2.0]heptane-6-sulfonic acid (338)

The titled compound has been prepared following scheme 12 and in analogy to example 43 using (1S,5R)-7-oxo-2,6-diazabicyclo[3.2.0]heptane-6-sulfonic acid (compound H) and commercially available (S)-3-amino-1-N—BOC-pyrrolidine as starting materials. The final depretotion step, using trifluoroacetic acid, has been performed in analogy to example 1.
+ESI-MS spectrum: m/z: 305 [M+H]$^+$.

Example 70

2-[N-(4-{[((3S)pyrrolidin-3-yl)amino]carbonylamino}phenyl) carbamoyl](1S,5R)-7-oxo-2,6-diazabicyclo[3.2.0]heptane-6-sulfonic acid (339)

The titled compound has been prepared following scheme 12 and in analogy to example 43 using (1S,5R)-7-oxo-2,6-diazabicyclo[3.2.0]heptane-6-sulfonic acid (compound H) and the commercially available 1,4-benzene diamine and also commercially available (S)-3-amino-1-N—BOC-pyrrolidine as starting materials. The final depretotion step, using trifluoroacetic acid, has been performed in analogy to example 1.
1H-NMR (DMSO-$d_6$): 1.65 (m, 1H); 1.82 (m, 1H); 2.17 (m, 1H); 2.31 (dd, J=5.8 and 13.6, 1H); 3.06 (dd, J=5.1 and 11.8, 1H); 3.19 (m, 2H); 3.29 (m, 2H); 3.96 (dd, J=8.3 and 11.1, 1H); 4.22 (m, 1H); 4.40 (t, J=4.7, 1H); 5.22 (d, J=4.3, 1H); 6.40 (d, J=6.0, 1H); 7.26 (d, J=9.2, 2H); 7.33 (d, J=9.2, 2H); 8.37 (s, 1H); 8.41 (s, 1H); 8.70 (br, 2H)

Example 71

(1S,5R)-2-{N-[4-(2-morpholin-4-ylethoxy)phenyl]carbamoyl}-7-oxo-2,6-diazabicyclo[3.2.0]heptane-6-sulfonic acid (340)

The titled compound has been prepared following scheme 12 and in analogy to example 43 using (1S,5R)-7-oxo-2,6-diazabicyclo[3.2.0]heptane-6-sulfonic acid (compound H) and the commercially available 4-(2-morpholin-4-ylethoxy)aniline as starting materials.
1H-NMR (DMSO-$d_6$): 1.66 (m, 1H); 2.31 (dd, J=5.8 and 13.6, 1H); 3.18 (m, 3H); 3.54 (m, 4H); 3.70 (m, 2H); 3.96 (m, 3H); 4.29 (m, 2H); 4.41 (t, J=4.7, 1H); 5.21 (d, J=4.3, 1H); 6.93 (d, J=9.0, 2H); 7.41 (d, J=9.0, 2H); 8.44 (s, 1H); 9.81 (br, 1H).

Example 72

(1S,5R)-2-{N-[3-(2-morpholin-4-ylethoxy)phenyl]carbamoyl}-7-oxo-2,6-diazabicyclo[3.2.0]heptane-6-sulfonic acid (341).

The titled compound has been prepared following scheme 12 and in analogy to example 43 using (1S,5R)-7-oxo-2,6-diazabicyclo[3.2.0]heptane-6-sulfonic acid (compound H) and the commercially available 3-(2-morpholin-4-ylethoxy)aniline as starting materials.
1H-NMR (DMSO-$d_6$): 1.66 (m, 1H); 2.31 (dd, J=5.8 and 13.6, 1H); 3.18 (m, 3H); 3.54 (m, 4H); 3.70 (m, 2H); 3.98 (m, 3H); 4.29 (m, 2H); 4.41 (t, J=4.7, 1H); 5.23 (d, J=4.3, 1H); 6.61 (dd, J=1.9 and 8.1, 1H); 7.04 (dd, J=1.1 and 8.1, 1H); 7.19 (t, J=8.1, 1H); 7.38 (s, 1H); 8.57 (s, 1H); 9.81 (br, 1H).

Example 73

(1S,5R)-7-oxo-2-[N-(4-piperidylphenyl)carbamoyl]-2,6-diazabicyclo[3.2.0]heptane-6-sulfonic acid (342)

The titled compound has been prepared following scheme 12 and in analogy to example 43 using (1S,5R)-7-oxo-2,6-diazabicyclo[3.2.0]heptane-6-sulfonic acid (compound H) and the commercially available 4-(1-piperidino)aniline as starting materials.
1H-NMR (DMSO-$d_6$): 1.40-2.00 (m, 7H); 2.30 (dd, J=5.8 and 13.5, 1H); 3.22 (m, 1H); 3.45 (br, 4H); 3.98 (dd, J=8.3 and 11.0, 1H); 4.42 (t, J=4.7, 1H); 5.24 (d, J=4.3, 1H); 7.50-7.75 (m, 4H); 8.85 (br, 1H); 10.80 (s, 1H).

Example 74

(1S,5R)-2-[N-(6-morpholin-4-yl(3-pyridyl))carbamoyl]-7-oxo-2,6-diazabicyclo[3.2.0]heptane-6-sulfonic acid (343).

The titled compound has been prepared following scheme 12 and in analogy to example 43 using (1S,5R)-7-oxo-2,6-diazabicyclo[3.2.0]heptane-6-sulfonic acid (compound H) and the commercially available 6-morpholinopyridine-3-amine as starting materials.

1H-NMR (DMSO-d$_6$). 1.70 (m, 1H); 2.34 (dd, J=5.8 and 13.5, 1H); 3.22 (m, 1H); 3.54 (m, 4H); 3.76 (m, 4H); 3.98 (dd, J=8.3 and 11.0, 1H); 4.42 (t, J=4.7, 1H); 5.19 (d, J=4.4, 1H); 7.38 (d, J=9.7, 1H); 8.06 (dd, J=2.4 and 9.7, 1H); 8.29 (d, J=2.4, 1H); 8.88 (br, 1H).

Example 75

(1S,5R)-2-{N-[4-(4-methylpiperazinyl)phenyl]carbamoyl}-7-oxo-2,6-diazabicyclo[3.2.0]heptane-6-sulfonic acid (344)

The titled compound has been prepared following scheme 12 and in analogy to example 43 using (1S,5R)-7-oxo-2,6-diazabicyclo[3.2.0]heptane-6-sulfonic acid (compound H) and the commercially available 4-(4-methylpiperazino) aniline as starting materials.

1H-NMR (DMSO-d$_6$): 1.65 (m, 1H); 2.31 (dd, J=5.8 and 13.6, 1H); 2.69 (m, 2H); 2.99 (m, 2H); 3.05-3.25 (m, 8H); 3.96 (dd, J=8.3 and 11.0, 1H); 4.39 (t, J=4.7, 1H); 5.31 (d, J=4.3, 1H); 6.91 (d, J=9.0, 2H); 7.35 (d, J=9.0, 2H); 8.36 (s, 1H)

Example 76

(1S,5R)-2-{2-[1-(dimethylamino)-2-oxohydropyrimidin-4-ylthio]acetyl}-7-oxo-2,6-diazabicyclo[3.2.0]heptane-6-sulfonic acid (203)

The titled compound was prepared following scheme 12 in analogy to example 14 using (5S,1R)-4,7-diazabicyclo[3.2.0]heptan-6-one (compound E) and 2-[1-(dimethylamino)-2-oxohydropyrimidin-4-ylthio]acetic acid. The resulting compound was then sulfonated according to the procedure described in J. Org. Chem. 1982, 5160.

+ESI-MS spectrum: m/z: 404 [M+H]$^+$.

2-[1-(dimethylamino)-2-oxohydropyrimidin-4-ylthio] acetic acid was prepared from the 3-(dimethylamino)-6-sulfanyl-3-hydropyrimidin-2-one (U.S. Pat. No. 4,348,518) and bromoacetic acid according to the procedures described in Russian J. Org. Chem. 2000, 761.

Example 77

(1S,5R)-7-oxo-2-{2-[4-(2-pyridiniumacetylamino) phenylthio]acetyl}-2,6-diazabicyclo[3.2.0]heptane-6-sulfonate, inner salt (204)

The titled compound was prepared following scheme 13 in analogy to example 14 using (5S,1R)-4,7-diazabicyclo[3.2.0]heptan-6-one (compound E) and the 2-[4-(2-pyridylacetylamino)phenylthio]acetic acid as starting materials. The resulting compound was then sulfonated according to the procedure described in J. Org. Chem. 1982, 5160.

+ESI-MS spectrum: m/z: 397 [M+H—SO$_3$]$^+$.

Example 78

(1S,5R)-2-(2-{1-[2-(dimethylamino)ethyl](1,2,3,4-tetraazol-5-ylthio)}acetyl)-7-oxo-2,6-diazabicyclo[3.2.0]heptane-6-sulfonic acid (205)

The titled compound was prepared following scheme 13 in analogy to example 14 using (5S,1R)-4,7-diazabicyclo[3.2.0]heptan-6-one (compound E) and 2-{1-[2-(dimethylamino)ethyl]-1,2,3,4-tetraazol-5-ylthio}acetic acid as starting materials. The resulting compound was then sulfonated according to the procedure described in J. Org. Chem. 1982, 5160.

2-{1-[2-(dimethylamino)ethyl]-1,2,3,4-tetraazol-5-ylthio}acetic acid was prepared from commercially available 1-(2-dimethylaminoethyl)-5-mercapto-1,2,3,4-tetrazole and bromo acetic acid according to the procedures described in Russian J. Org. Chem. 2000, 761.

+ESI-MS spectrum: m/z: 406 [M+H]$^+$.

Example 79

Sodium (1S,5R)-2-[2-(1-methyl(1,3,4-thiadiazol-2-ylthio))acetyl]-7-oxo-2,6-diazabicyclo[3.2.0]heptane-6-sulfonate (202)

The titled compound was prepared following scheme 13 in analogy to example 14 using (5S,1R)-4,7-diazabicyclo[3.2.0] heptan-6-one (compound E) and the commercially available 2-(5-methyl-1,3,4-thiadiazol-2-ylthio)acetic acid as starting materials. The resulting compound was then sulfonated according to the procedure described in J. Org. Chem. 1982, 5160.

−ESI-MS spectrum: m/z: 363 [M−H]$^+$.

Example 80

(1S,5R)-2-[2-(4-{N-[2-(dimethylamino)ethyl] carbamoyl}phenylthio)acetyl]-7-oxo-2,6-diazabicyclo[3.2.0]heptane-6-sulfonic acid (207).

[5-(2-Dimethylamino-ethylcarbamoyl)phenylthio] acetic acid

To a suspension of commercially available 4-mercapto benzoic acid (1.54 g, 10 mmol) in water was added NaOH (0.88 g, 22 mmol). The resulting solution was stirred at room temperature for 30 min and then bromo acetic acid ethyl ester (1.67 g, 10 mmol) was slowly added to the previous solution. After stirring at room temperature for 2 hours, an aqueous solution containing HCl (1M) was added. The obtained precipitate was filtrated, washed with water and dried to afford 1.5 g of 4-ethoxycarbonylmethylthio benzoic acid.

−ESI-MS spectrum: m/z: 239 [M−H]$^+$.

Then the corresponding acid chloride of 4-ethoxycarbonylmethylthio benzoic acid was prepared in analogy to the procedure described in Synthesis, 1985, 517 and the condensation of the commercially available 2-dimethylaminoethyl amine and the hydrolysis of the ester group were performed in analogy to the procedure described in Bioorg. Med. Chem. Lett. 2003, 1517.

+ESI-MS spectrum: m/z: 283 [M+H]$^+$ (1S,5R)-2-[2-(4-{N-[2-(dimethylamino)ethyl] carbamoyl}phenylthio)acetyl]-7-oxo-2,6-diazabicyclo[3.2.0]heptane-6-sulfonic acid (207)

[5-(2-Dimethylamino-ethylcarbamoyl)phenylthio]acetic acid (144 mg, 0.49 mmol, 1.0 eq) was added at room temperature to a stirred solution of (1S,5R)-7-oxo-2,6-diazabicyclo[3.2.0]heptane-6-sulfonic acid (compound H, 100 mg, 0.49 mmol, 1.0 eq) in DMSO (4 mL), followed by O-(benzotriazo-yl)-1,1,3,3-tetramethyluronium hexafluorophosphate (HBTU) (225 mg, 0.59 mmol, 1.2 eq) and triethylamine (83 μL, 0.59 mmol, 1.2 eq). After 4 hours stirring at room temperature, DMSO was evaporated, the crude was treated with acetonitrile. The resulting mixture was filtered to afford the crude product as a yellow solid which was purified by preparative HPLC: 74 mg (30%).

1H-NMR (DMSO-$d_6$): 1.70 (m, 1H); 2.32 (m, 1H); 2.83 (s, 6H); 3.14 and 3.38 (2m, 1H); 3.26 (m, 2H); 3.57 (m, 2H); 3.96-4.23 (m, 3H); 4.34 and 4.51 (2t, J=4.7, 1H); 5.16 and 5.31 (2d, J=4.3, 1H); 7.43 (dd, J=8.5 and 12.6, 2H); 7.78 (dd, J=2.4 and 8.5, 2H); 8.62 (m, 1H); 9.18 (br, 1H).

Example 81

(1S,5R)-2-[2-(5-{N-[2-(dimethylamino)ethyl]carbamoyl}(2-pyridylthio)) acetyl]-7-oxo-2,6-diazabicyclo[3.2.0]heptane-6-sulfonic acid (208)

The titled compound has been prepared following scheme 13 and in analogy to example 80 using (1S,5R)-7-oxo-2,6-diazabicyclo[3.2.0]heptane-6-sulfonic acid (compound H) and [5-(2-dimethylaminoethylcarbamoyl)pyridin-2-ylthio]acetic acid as starting materials.

1H-NMR (DMSO-$d_6$): 1.66 (m, 1H); 2.33 (m, 1H); 2.82 (s, 3H); 2.85 (s, 3H); 3.15 and 3.48 (2m, 1H); 3.26 (m, 2H); 3.61 (m, 2H); 3.98-4.55 (m, 4H); 5.16 and 5.35 (2t, J=4.3, 1H); 7.48 (d, J=8.4, 1H); 8.02 (m, 1H); 8.75 (m, 1H); 8.85 (dd, J=1.8 and 7.5, 1H); 9.16 (br, 1H).

[5-(2-Dimethylamino-ethylcarbamoyl)pyridin-2-ylthio]acetic acid was prepared in analogy to the procedure described in Bioorg. Med. Chem. Lett. 2003, 1517 using bromo acetic acid ethyl ester and commercially available 2-dimethylaminoethyl amine.

Example 82

(1S,5R)-2-(2-[({4-N-(2-aminoethyl)carbamoyl]phenylthio}acetyl)-7-oxo-2,6-diazabicyclo[3.2.0]heptane-6-sulfonic acid (209)

The titled compound has been prepared following scheme 13 and in analogy to example 80 using (1S,5R)-7-oxo-2,6-diazabicyclo[3.2.0]heptane-6-sulfonic acid (compound H) and [4-(2-tert-butoxycarbonylaminoethylcarbamoyl)phenylthio]acetic acid as starting materials. The final deprotection step, using trifluoroacetic acid, has been performed in analogy to example 1.

1H-NMR (DMSO-$d_6$): 1.72 (m, 1H); 2.33 (m, 1H); 2.97 (t, J=6.0, 2H); 3.14 and 3.38 (2m, 1H); 3.48 (q, J=6.0, 2H); 3.95-4.24 (m, 3H); 4.34 and 4.51 (2t, J=4.8, 1H); 5.17 and 5.32 (2d, J=4.3, 1H); 7.42 (dd, J=8.5 and 13.1, 2H); 7.78 (dd, J=2.5 and 8.5, 2H); 8.55 (m, 1H).

[4-(2-Tert-butoxycarbonylaminoethylcarbamoyl)phenylthio]acetic acid was prepared in analogy to the procedure described in example 80 using 4-ethoxycarbonylmethylthiobenzoic acid and commercially available (2-aminoethyl)carbamic acid tert-butyl ester.

Example 83

(1S,5R)-2-(2-{4-[N-(2-aminoethyl)-N-methylcarbamoyl]phenylthio}acetyl)-7-oxo-2,6-diazabicyclo[3.2.0]heptane-6-sulfonic acid (210).

The titled compound has been prepared following scheme 13 and in analogy to example 80 using (1S,5R)-7-oxo-2,6-diazabicyclo[3.2.0]heptane-6-sulfonic acid (compound H) and {4-[(2-tert-butoxycarbonylaminoethyl)methylcarbamoyl]phenylthio}acetic acid as starting materials. The final deprotection step, using trifluoroacetic acid, has been performed in analogy to example 1.

–ESI-MS spectrum: m/z: 441 [M–H]$^+$

{4-[(2-Tert-butoxycarbonylaminoethyl)methylcarbamoyl]phenylthio}acetic acid was prepared in analogy to the procedure described in example 80 using 4-ethoxycarbonylmethylsulfanylbenzoic acid and commercially available (2-methylamino-ethyl)carbamic acid tert-butyl ester.

Example 84

(1S,5R)-2-[2-(4-{N-[2-(methylamino)ethyl]carbamoyl}phenylthio)acetyl]-7-oxo-2,66-diazabicyclo[3.2.0]heptane-6-sulfonic acid (211)

The titled compound has been prepared following scheme 13 and in analogy to example 80 using (1S,5R)-7-oxo-2,6-diazabicyclo[3.2.0]heptane-6-sulfonic acid (compound H) and {4-[2-(tert-butoxycarbonylmethylamino)ethylcarbamoyl]phenylthio}acetic acid as starting materials. The final deprotection step, using trifluoroacetic acid, has been performed in analogy to example 1.

–ESI-MS spectrum: m/z: 441 [M–H]+

{4-[2-(Tert-butoxycarbonylmethylamino)ethylcarbamoyl]phenylthio}acetic acid was prepared in analogy to the procedure described in example 80 using 4-ethoxycarbonylmethylthiobenzoic acid and commercially available (2-aminoethyl)methylcarbamic acid tert-butyl ester.

Example 85

(1S,5R)-7-oxo-2-{2-[4-(piperazinylcarbonyl)phenylthio]acetyl}-2,6-diazabicyclo[3.2.0]heptane-6-sulfonic acid (212)

The titled compound has been prepared following scheme 13 and in analogy to example 80 using (1S,5R)-7-oxo-2,6-diazabicyclo[3.2.0]heptane-6-sulfonic acid (compound H) and 4-(4-carboxymethylthiobenzoyl)piperazine-1-carboxylic acid tert-butyl ester as starting materials. The final deprotection step, using trifluoroacetic acid, has been performed in analogy to example 1.

–ESI-MS spectrum: m/z: 453 [M–H]$^+$ 4-(4-Carboxymethylsulfanyl-benzoyl)piperazine-1-carboxylic acid tert-butyl ester was prepared in analogy to the procedure described in example 80 using 4-ethoxycarbonylmethylthiobenzoic acid and commercially available piperazine-1-carboxylic acid tert-butyl ester.

Example 86

(1S,5R)-2-{2-[4-(2-aminoethoxy)phenylthio]acetyl}-7-oxo-2,6-diazabicyclo[3.2.0]heptane-6-sulfonic acid (213)

The titled compound has been prepared following scheme 13 and in analogy to example 80 using (1S,5R)-7-oxo-2,6-diazabicyclo[3.2.0]heptane-6-sulfonic acid (compound H) and [4-(2-tert-butoxycarbonylaminoethoxy)phenylthio]acetic acid as starting materials. The final deprotection step, using trifluoroacetic acid, has been performed in analogy to example 1.

–ESI-MS spectrum: m/z: 400 [M–H]$^+$

[4-(2-Tert-butoxycarbonylaminoethoxy)phenylthio]acetic acid was prepared in analogy to the procedure described in J.

Med. Chem. 2000, 721 using first bromo acetic ethyl ester and then the commercially available (2-bromoethyl)carbamic acid tert-butyl ester.

Example 87

(1S,5R)-2-(2-{5-[N-(2-aminoethyl)carbamoyl](2-pyridylthio)}acetyl)-7-oxo-2,6-diazabicyclo[3.2.0]heptane-6-sulfonic acid (214)

The titled compound has been prepared following scheme 13 and in analogy to example 80 using (1S,5R)-7-oxo-2,6-diazabicyclo[3.2.0]heptane-6-sulfonic acid (compound H) and [4-(2-tert-butoxycarbonylaminoethylcarbamoyl)phenylthio]acetic acid as starting materials. The final deprotection step, using trifluoroacetic acid, has been performed in analogy to example 1.
−ESI-MS spectrum: m/z: 428 [M−H]$^+$
[4-(2-Tert-butoxycarbonylamino-ethylcarbamoyl)phenylthio]acetic acid was prepared in analogy to the procedure described in Bioorg. Med. Chem. Lett. 2003, 1517 using bromo acetic acid ethyl ester and commercially available (2-aminoethyl)carbamic acid tert-butyl ester.

Example 88

(1S,5R)-2-[2-(5-{N-[2-(methylamino)ethyl]carbamoyl}(2-pyridylthio))acetyl]-7-oxo-2,6-diazabicyclo[3.2.0]heptane-6-sulfonic acid (215)

The titled compound has been prepared following scheme 13 and in analogy to example 80 using (1S,5R)-7-oxo-2,6-diazabicyclo[3.2.0]heptane-6-sulfonic acid (compound H) and {4-[2-(tert-butoxycarbonylmethylamino)ethylcarbamoyl]phenylthio}acetic acid as starting materials. The final deprotection step, using trifluoroacetic acid, has been performed in analogy to example 1.
−ESI-MS spectrum: m/z: 442 [M−H]$^+$
{4-[2-(Tert-butoxycarbonylmethylamino)ethylcarbamoyl]phenylthio}acetic acid was prepared in analogy to the procedure described in Bioorg. Med. Chem. Lett. 2003, 1517 using bromo acetic acid ethyl ester and commercially available (2-methylaminoethyl)carbamic acid tert-butyl ester.

Example 89

(1S,5R)-2-{2-[(3-carbamoylpyridyl-4)carbonylamino]acetyl}-7-oxo-2,6-diazabicyclo[3.2.0]heptane-6-sulfonic acid (402)

The titled compound was prepared following scheme 11 in analogy to example 24 using (5S,1R)-4-(2-bromoacetyl)-4,7-diazabicyclo[3.2.0]heptan-6-one (compound F) which was first sulfonated (J. Org. Chem. 1982, 5160) and the commercially available 3,4-pyridine dicarboxamide as starting materials.
+ESI-MS spectrum: m/z: 398 [M+H]$^+$.

Example 90

Sodium 2-{[(4S)-2-(2-hydroxyphenyl)(4,5-dihydro-1,3-thiazolin-4-yl)]carbonyl}(1S,5R)-7-oxo-2,6-diazabicyclo[3.2.0]heptane-6-sulfonate (404)

The titled compound was prepared following scheme 13 in analogy to example 14 using (5S,1R)-4,7-diazabicyclo[3.2.0]heptan-6-one (compound E) and the (4S) 4,5-dihydro-2-(2-hydroxyphenyl)-4-thiazolecarboxylic acid (JP59141554). The resulting compound was then sulfonated according to the procedure described in J. Org. Chem. 1982, 5160.
−ESI-MS spectrum: m/z: 397 [M+H]$^+$.

Example 91

Sodium (1S,5R)-2-{2-[(5-fluoro-2-oxohydropyrimidin-4-yl)amino]acetyl}-7-oxo-2,6-diazabicyclo[3.2.0]heptane-6-sulfonate (405)

The titled compound was prepared following scheme 11 in analogy to example 22 using (5S,1R)-4-(2-bromoacetyl)-4,7-diazabicyclo[3.2.0]heptan-6-one (compound F) and the commercially available 4-amino-5-fluoro pyridine-2-one.
−ESI-MS spectrum: m/z: 361 [M+H]$^+$.

Example 92

(1S,5R)-2-[2-amino-2-(4-carbamoylphenyl)acetyl]-7-oxo-2,6-diazabicyclo[3.2.0]heptane-6-sulfonic acid (406)

The titled compound was prepared following scheme 13 in analogy to example 14 using (5S,1R)-4,7-diazabicyclo[3.2.0]heptan-6-one (compound E) and 2-amino-2-(4carbamoylphenyl)acetic acid, obtained according to the procedure described in Eur. J. Med. Chem. 2003, 289 from 4-{[(tert-butoxy)carbonylamino](methoxycarbonyl)methyl}benzoic acid (WO-A-2000/076970). The resulting compound was then sulfonated according to the procedure described in J. Org. Chem. 1982, 5160.
+ESI-MS spectrum: m/z: 368 [M+H]$^+$.

Example 93

(1S,5R)-2-{2-[4-(imidazolylcarbonyl)-1-methylpiperazinium]acetyl}-7-oxo-2,6-diazabicyclo[3.2.0]heptane-6-sulfonate, inner salt (407)

The titled compound was prepared following scheme 13 in analogy to example 24 using (5S,1R)-4-(2-bromoacetyl)-4,7-diazabicyclo[3.2.0]heptan-6-one (compound F) and 1-(1H-imidazol-1-ylcarbonyl)-4-methyl-piperazine (Ind. J. Chem., Section B, 1987, 748).
+ESI-MS spectrum: m/z: 426 [M]$^+$.

Example 94

Sodium (1S,5R)-2-{[(4-carbamoylphenyl)amino]carbonylamino}-7-oxo-2,6-diazabicyclo[3.2.0]heptane-6-sulfonate (408)

The titled compound was prepared following the procedure described for example 18 of U.S. Pat. No. 6,566,355 using (5S,1R)-4,7-diazabicyclo[3.2.0]heptan-6-one (compound E) and 4-[(3-phenyl-1,2-oxaziridin-2-yl)carbonylamino]benzamide. The resulting compound was then sulfonated according to the procedure described in J. Org. Chem. 1982, 5160.
−ESI-MS spectrum: m/z: 369 [M+H]$^+$.
Biological Evaluation Antimicrobial activity of the compounds and of their combinations was determined against a selection of organisms according to the standard procedures described by the National Committee for Clinical Laboratory Standards (National Committee for Clinical Laboratory Standards (2000).

Methods for Dilution Antimicrobial Susceptibility Tests for Bacteria That Grow Aerobically-Fifth Edition: Approved Standard M7-A5. NCCLS, Wayne, Pa., USA).

The compounds to be tested were dissolved in 100% DMSO or sterile broth according to their aqueous solubility and were diluted to the final reaction concentration (0.06-32 µg/mL) in microbial growth media (IsoSensiTest Broth+16 µg/mL 2,2'-bipyridyl). In all cases the final concentration of DMSO incubated with the bacteria is less than or equal to 1%. For estimation of the minimal inhibitory concentrations (MIC), 2-fold dilutions of compounds were added to wells of a microtitre plate containing 106 bacteria/mL. Plates were incubated overnight at an appropriate temperature (30° C. or 37° C.) and optical densities assessed by eye. The MIC value is defined as the lowest compound concentration completely inhibiting visible growth of the test organism. When combinations between compounds of formula I with compounds of formula II and III-XIII are evaluated the compounds of formula I are tested in dilution series as described above while the compounds of formula II and III-XIII were present in all wells at a constant concentration of 4 µg/mL each.

The MIC values (in mg/L) of representative compounds and of representative combinations including these compounds are listed in tables 3, 4 and 5. Table 3 lists the MIC values obtained for two representative antibiotics of formula I when combined either with a compound of formula II or with a compound of formula III-XIII in comparison to the activity obtained with a combination involving the antibiotic of formula I with a compound of formula II and a compound of formula III-XIII together. Table 4 lists the activity of representative compounds of formula I alone or in combination with compounds of formula II and formula III-XIII. Table 5 lists the MIC values obtained for representative compounds of formula II with selected compounds of formula I and formula III-XIII.

If in table 4 in the upper three rows a cell is left empty, then this means that in the combination of that column no compound of the category of that row was used.

TABLE 3

Activity of representative monobactam antibiotics alone and in representative combinations according to the invention

| | | compound of formula I | | | | | | | | |
|---|---|---|---|---|---|---|---|---|---|---|
| | | 1 | | | | | Aztreonam | | | |
| | | compound of formula II | | | | | | | | |
| | | | | 206 | 323 | | | | 206 | 323 |
| | | | | Supplementary b-lactamase inhibitor | | | | | | |
| | Strain | | clavulanate | 501 | clavulanate | | clavulanate | 501 | | sulbactam |
| | | Minimal Inhibitory concentration (mg/L) of antibiotic at fixed inhibitor concentration of 4 mg/L | | | | | | | | |
| Enterobacter cloacae | B1102 | >32 | 32 | 16 | 16 | 8 | 2 | 16 | 2 | 0.125 | 2 |
| | ATCC13047/CRO-R | >32 | >32 | >32 | >32 | 8 | >32 | >32 | >32 | 8 | 8 |
| | M4018 | 32 | >32 | 16 | 8 | 2 | >32 | >32 | 32 | 1 | 4 |
| | MRW | >32 | 32 | 32 | 16 | 4 | >32 | 32 | 32 | 1 | 2 |
| Enterobacter aerogenes | Zayakosky | >32 | >32 | >32 | >32 | 16 | >32 | >32 | >32 | 16 | 8 |
| | B1 | 32 | >32 | >32 | 16 | 4 | 16 | >32 | 32 | 8 | 8 |

TABLE 4

Activity of combinations of representative antibiotics

| Antibiotic | Meropenem | Cefepime | Amoxicillin | Amoxicillin | Ampicillin | Aztreonam | Aztreonam | Aztreonam | Aztreonam |
|---|---|---|---|---|---|---|---|---|---|
| β-lactamase inhibitor of formula II | | 1/202 | 5/102 | | | | 1/323 | 1/324 | |
| β-lactamase inhibitor of formula V or VI | | clavulanate | clavulanate | 6/206 clavulanate | 1/323 sulbactam | | clavulanate | clavulanate | 1/102 sulbactam |

MIC (mg/L) of antibiotic at fixed inhibitor concentration of 4 mg/L

| Bacterial strain | | | | | | | | | |
|---|---|---|---|---|---|---|---|---|---|
| Acinetobacter baumannii J2 | 2 | 32 | 32 | 4 | 1 | >32 | 16 | 32 | 4 |
| Pseudomonas aeruginosa MK1184 | 2 | 32 | >32 | >32 | 4 | >32 | 16 | 8 | 16 |
| Pseudomonas aeruginosa 1973E | 1 | 4 | >32 | 4 | 4 | 8 | 8 | 8 | 4 |
| Enterobacter cloacae P99 | 0.13 | 2 | 8 | 0.25 | 4 | >32 | 2 | 2 | 2 |
| Klebsiella pneumoniae CF104 | <0.06 | 4 | 32 | 4 | 1 | >32 | 0.5 | 0.5 | 1 |
| Serratia marcescens S6 | 16 | 0.13 | >32 | 0.25 | 0.5 | 32 | 4 | 2 | 0.5 |
| Stenotrophomonas maltophilia 1AC736 | 32 | 4 | >32 | 0.125 | 0.125 | >32 | 0.5 | 8 | 2 |

| Antibiotic | Aztreonam | Aztreonam | Aztreonam | Aztreonam | Aztreonam | Aztreonam | Aztreonam |
|---|---|---|---|---|---|---|---|
| β-lactamase inhibitor of formula II | 2/206 | 2/206 | 20 | 20 | 20 | 20 | 20/206 |
| β-lactamase inhibitor of formula V or VI | clavulanate | clavulanate | clavulanate | 501 clavulanate | clavulanate | 102 clavulanate | clavulanate |

MIC (mg/L) of antibiotic at fixed inhibitor concentration of 4 mg/L

| Bacterial strain | | | | | | | |
|---|---|---|---|---|---|---|---|
| Acinetobacter baumannii J2 | 16 | 32 | >32 | <0.06 | >32 | >32 | >32 |
| Pseudomonas aeruginosa MK1184 | 16 | 8 | >32 | >32 | >32 | 8 | >32 |
| Pseudomonas aeruginosa 1973E | 8 | 8 | 16 | 16 | 16 | 32 | 16 |
| Enterobacter cloacae P99 | 16 | 4 | >32 | >32 | >32 | 16 | 16 |
| Klebsiella pneumoniae CF104 | 8 | 1 | 32 | 16 | 32 | 2 | 4 |
| Serratia marcescens S6 | >32 | 0.5 | 4 | 2 | 2 | 0.5 | 0.5 |
| Stenotrophomonas maltophilia 1AC736 | 0.5 | 0.125 | 4 | 0.25 | 0.25 | 0.25 | 0.5 |

| Antibiotic | Aztreonam | Aztreonam | Aztreonam | Aztreonam |
|---|---|---|---|---|
| β-lactamase inhibitor of formula I | 28 | 28/102 | 21 | 21/102 |
| β-lactamase inhibitor of formula V or VI | clavulanate | clavulanate | clavulanate | sulbactam |

MIC (mg/L) of antibiotic at fixed inhibitor concentration of 4 mg/L

| Bacterial strain | | | | |
|---|---|---|---|---|
| Acinetobacter baumannii J2 | >32 | >32 | >32 | 2 |
| Pseudomonas aeruginosa MK1184 | >32 | 32 | >32 | 32 |
| Pseudomonas aeruginosa 1973E | 16 | 16 | 16 | 16 |
| Enterobacter cloacae P99 | >32 | >32 | >32 | 32 |
| Klebsiella pneumoniae CF104 | 8 | 2 | 8 | 2 |
| Serratia marcescens S6 | 0.5 | 1 | 0.5 | 16 |
| Stenotrophomonas maltophilia 1AC736 | 0.5 | 1 | 0.5 | 8 |

| Antibiotic | Aztreonam | Aztreonam | Aztreonam |
|---|---|---|---|
| β-lactamase inhibitor of formula I | 21/102 | 21/323 | |
| β-lactamase inhibitor of formula V or VI | clavulanate | sulbactam | |

| Bacterial strain | | | |
|---|---|---|---|
| Acinetobacter baumannii J2 | >32 | 2 | |
| Pseudomonas aeruginosa MK1184 | 16 | 8 | |
| Pseudomonas aeruginosa 1973E | 8 | 32 | |
| Enterobacter cloacae P99 | 32 | 8 | |
| Klebsiella pneumoniae CF104 | <0.06 | 1 | |
| Serratia marcescens S6 | 0.5 | 2 | |
| Stenotrophomonas maltophilia 1AC736 | 2 | 4 | |

TABLE 4-continued

Activity of combinations of representative antibiotics

| Antibiotic of formula I | 21 | 21 | 12 | 12 | 12 | 12 | 12 | 12 | 9 | 9 | 29 | 29 | 29 | 29 | 29 |
|---|---|---|---|---|---|---|---|---|---|---|---|---|---|---|---|
| β-lactamase inhibitor of formula II | 323 | 324 | 102 | 102 | 103 | 323 | 324 | 102 | 102 | 102 | 102 | 102 | 102 | 102 | 323 |
| β-lactamase inhibitor of formula V or VI | clavulanate | sulbactam | | sulbactam | sulbactam | sulbactam | sulbactam | clavulanate | clavulanate | | sulbactam | clavulanate | clavulanate | sulbactam | sulbactam |

Bacterial strain | MIC (mg/L) of antibiotic at fixed inhibitor concentration of 4 mg/L

| Bacterial strain | | | | | | | | | | | | | | | |
|---|---|---|---|---|---|---|---|---|---|---|---|---|---|---|---|
| Acinetobacter baumannii J2 | 8 | 2 | 4 | 4 | 1 | 2 | 2 | >32 | >32 | >32 | >32 | >32 | 2 | 2 | 2 |
| Pseudomonas aeruginosa MK1184 | 32 | 32 | >32 | 4 | | 16 | 16 | 16 | >32 | 8 | >32 | 8 | 4 | 4 | 8 |
| Pseudomonas aeruginosa 1973E | 16 | 16 | >32 | 8 | 16 | 4 | 16 | 4 | 4 | 8 | 4 | 8 | 8 | 8 | 8 |
| Enterobacter cloacae P99 | 8 | 8 | >32 | 8 | 32 | 8 | 8 | 16 | 8 | 32 | >32 | 0.25 | 0.25 | 2 | 2 |
| Klebsiella pneumoniae CF104 | 2 | 4 | >32 | 2 | 4 | 4 | 4 | 0.25 | 0.5 | 0.5 | >32 | 0.5 | 0.5 | 8 | 8 |
| Serratia marcescens S6 | 2 | 4 | 32 | 1 | 16 | 16 | 16 | 2 | 1 | 1 | 32 | 1 | 1 | 2 | 2 |
| Stenotrophomonas maltophila 1AC736 | 2 | 4 | 1 | 4 | 2 | 0.5 | 4 | 0.125 | 0.25 | 0.5 | 1 | 0.5 | 0.5 | 1 | 1 |

| Antibiotic of formula I | 22 | 22 | 22 | 23 | 23 | 23 | 23 | 26 | 26 |
|---|---|---|---|---|---|---|---|---|---|
| β-lactamase inhibitor of formula II | | 324 | 324 | | 324 | 102 | 102 | 102 | 102 |
| β-lactamase inhibitor of formula V or VI | Clavulanate | Clavulanate | Sulbactam | | Sulbactam | Clavulanate | Clavulanate | | Clavulanate |

Bacterial strain | MIC (mg/L) of antibiotic at fixed inhibitor concentration of 4 mg/L

| Bacterial strain | | | | | | | | | |
|---|---|---|---|---|---|---|---|---|---|
| Acinetobacter baumannii J2 | | 8 | 2 | | 2 | 8 | 8 | 2 | 4 |
| Pseudomonas aeruginosa MK1184 | | 4 | 4 | | 8 | 8 | 8 | 8 | 2 |
| Pseudomonas aeruginosa 1973E | | 4 | 4 | | 16 | 16 | 16 | 16 | 2 |
| Enterobacter cloacae P99 | | 4 | 4 | | 8 | 8 | 4 | 8 | 2 |
| Klebsiella pneumoniae CF104 | | 0.25 | 0.13 | | 2 | 2 | 1 | 2 | 0.25 |
| Serratia marcescens S6 | | 0.13 | 1 | | 0.5 | 0.25 | 0.25 | 0.5 | 0.25 |
| Stenotrophomonas maltophila 1AC736 | | 1 | not tested | | | | not tested | | 4 |
| Acinetobacter baumannii J51 | | | not tested | | | | | | 4 |

| Antibiotic of formula I | 26 | 26 | 26 | 26 | 26 | 26 | 26 | 26 | 26 |
|---|---|---|---|---|---|---|---|---|---|
| β-lactamase inhibitor of formula II | 102 | 324 | 102 | 324 | | 501 | | | |
| β-lactamase inhibitor of formula V or VI | Sulbactam | Sulbactam | | | clavulanic acid | | sulbactam | tazobactam | BRL427158 |

Bacterial strain | MIC (mg/L) of antibiotic at fixed inhibitor concentration of 4 mg/L

| Bacterial strain | | | | | | | | | |
|---|---|---|---|---|---|---|---|---|---|
| Acinetobacter baumannii J2 | 2 | 2 | 4 | 4 | >32 | 0.5 | 2 | 4 | 0.5 |
| Pseudomonas aeruginosa MK1184 | 2 | 2 | 2 | 4 | 4 | 2 | 4 | 2 | 2 |
| Pseudomonas aeruginosa 1973E | 4 | 2 | 2 | 2 | 2 | 2 | 2 | 2 | 2 |
| Enterobacter cloacae P99 | 2 | 2 | 2 | 8 | 8 | 8 | 8 | 16 | 16 |
| Klebsiella pneumoniae CF104 | 1 | 1 | 1 | 1 | 0.5 | 1 | 1 | 1 | 1 |
| Serratia marcescens S6 | <0.06 | <0.06 | ≤0.06 | ≤0.06 | ≤0.06 | ≤0.06 | ≤0.06 | ≤0.06 | ≤0.06 |
| Stenotrophomonas maltophila 1AC736 | 0.25 | 0.25 | 0.25 | 0.25 | ≤0.06 | 0.125 | ≤0.06 | ≤0.06 | 0.125 |
| Acinetobacter baumannii J51 | not tested | not tested | 2 | 1 | 1 | ≤0.06 | 2 | 4 | 32 |
| Enterobacter aerogenes Zayakosky 5 | not tested | not tested | 4 | 8 | 8 | 16 | 16 | 16 | 0.5 |

| Antibiotic of formula I | 41 | 41 | 41 | 48 | 48 | 48 | 25 | 25 | 25 | 47 | 47 | 47 | 32 | 32 | 32 | 33 | 33 | 33 |

TABLE 4-continued

Activity of combinations of representative antibiotics

| β-lactamase inhibitor of formula II | 102 | 324 | 102 | 324 | 102 | 324 | 102 | 324 | 102 | 324 | 102 | 324 |
|---|---|---|---|---|---|---|---|---|---|---|---|---|
| β-lactamase inhibitor of formula V or VI | clavulanic acid | clavulanic acid | clavulanic acid | clavulanic acid | clavulanic acid | clavulanic acid | clavulanic acid | clavulanic acid | clavulanic acid | clavulanic acid | clavulanic acid | clavulanic acid |
| Bacterial strain | MIC (mg/L) of antibiotic at fixed inhibitor concentration of 4 mg/L | | | | | | | | | | | |
| Acinetobacter baumannii J2 | 16 | 4 | >32 | >32 | >32 | >32 | >32 | >32 | 4 | 8 | 16 | 8 |
| Pseudomonas aeruginosa MK1184 | 4 | 4 | 4 | 2 | 2 | 4 | 4 | 4 | 4 | 4 | 16 | 32 |
| Pseudomonas aeruginosa 1973E | 4 | 8 | 8 | 8 | 4 | 8 | 16 | 8 | 8 | 8 | 16 | 16 |
| Enterobacter cloacae P99 | >32 | 16 | >32 | 16 | 32 | 4 | >32 | 32 | 8 | 4 | 4 | 16 |
| Klebsiella pneumoniae CF104 | >32 | 0.5 | >32 | 4 | 2 | 0.5 | >32 | >32 | 1 | 2 | 0.5 | 0.5 |
| Serratia marcescens S6 | 1 | 0.5 | 8 | 2 | 2 | 1 | 2 | 2 | 0.25 | 0.25 | 0.25 | 0.25 |
| Stenotrophomonas maltophila 1AC736 | 1 | 1 | 4 | 2 | 4 | 1 | 1 | 1 | 0.5 | 0.5 | 2 | 2 |

TABLE 5

Activity of compounds of general formula II in representative combinations

| Bridged Monobactam of formula II | Supplementary β-lactamase inhibitor of formula V or VI | Antibiotic of formula I | MIC of antibiotic at fixed inhibitor concentration (4 mg/L) | | | | | | |
|---|---|---|---|---|---|---|---|---|---|
| | | | Acinetobacter sp. J2 | Pseudomonas aeruginosa MK1184 | Pseudomonas aeruginosa 1973E | Enterobacter cloacae P99 | Klebsiella pneumoniae CF104 | Serratia marcescens S6 | Stenotrophomonas malthophilia 1AC736 |
| | | Meropenem | 2 | 2 | 1 | 0.125 | <0.06 | 16 | 32 |
| | | Cefepime | 32 | 32 | 4 | 2 | 4 | 0.125 | 4 |
| | | Aztreonam | >32 | >32 | 8 | >32 | >32 | 32 | >32 |
| | | 1 | >32 | >32 | 16 | >32 | >32 | 1 | 0.5 |
| 101 | clavulanate | 1 | >32 | 8 | 4 | 32 | 2 | 0.5 | 0.125 |
| 102 | clavulanate | 1 | 4 | 4 | 2 | 4 | 1 | 0.25 | 0.125 |
| 103 | clavulanate | 1 | 8 | 8 | 4 | 32 | 0.5 | 0.25 | 0.125 |
| 104 | clavulanate | 1 | >32 | 32 | 4 | 32 | 0.5 | 2 | 0.125 |
| 105 | clavulanate | 1 | 8 | 16 | 8 | 32 | 0.5 | 0.125 | 0.125 |
| 106 | clavulanate | 1 | >32 | 32 | 4 | >32 | 0.25 | 0.25 | 0.125 |
| 107 | clavulanate | 1 | 8 | 8 | 4 | 32 | 1 | 0.125 | 0.125 |
| 108 | clavulanate | 1 | >32 | >32 | 4 | 4 | 1 | 0.25 | 0.125 |
| 109 | clavulanate | 1 | 4 | 16 | 4 | 32 | 0.5 | 0.125 | 0.125 |
| 110 | clavulanate | 1 | 2 | 32 | 4 | >32 | 0.125 | 0.25 | 0.125 |
| 111 | clavulanate | 1 | 4 | 8 | 4 | 4 | <0.06 | 0.25 | 0.125 |
| 112 | clavulanate | 1 | 16 | >32 | 8 | >32 | <=0.06 | 0.5 | 0.125 |
| 113 | clavulanate | 1 | >32 | >32 | 4 | 32 | 0.125 | 0.25 | 0.25 |
| 114 | clavulanate | 1 | >32 | 16 | 4 | 32 | 0.125 | 0.25 | 0.125 |
| 115 | clavulanate | 1 | >32 | 16 | 4 | 32 | 0.125 | 0.25 | 0.125 |
| 116 | clavulanate | 1 | 16 | 8 | 16 | 32 | 0.5 | 0.25 | 0.125 |
| 117 | clavulanate | 1 | >32 | 16 | 4 | 32 | 0.125 | 0.25 | 0.25 |
| 118 | clavulanate | 1 | >32 | 32 | 4 | 32 | 0.125 | 0.25 | 0.125 |
| 119 | clavulanate | 1 | >32 | 32 | 4 | >32 | 0.125 | 0.25 | 0.125 |
| 120 | clavulanate | 1 | 32 | 16 | 8 | 32 | 0.25 | 0.25 | 0.125 |
| 121 | clavulanate | 1 | >32 | 16 | 4 | 32 | 0.25 | 0.25 | 0.25 |
| 122 | clavulanate | 1 | >32 | 16 | 4 | 16 | 0.125 | 0.25 | 0.125 |
| 123 | clavulanate | 1 | >32 | 32 | 4 | 32 | 0.125 | 0.25 | 0.125 |
| 124 | clavulanate | 1 | >32 | 32 | 8 | 32 | 0.125 | 0.25 | 0.125 |
| 125 | clavulanate | 1 | 4 | 16 | 8 | 32 | <0.06 | 0.5 | 0.125 |
| 126 | clavulanate | 1 | 2 | 16 | 8 | 32 | >32 | 0.125 | 0.125 |
| 201 | clavulanate | 1 | 4 | 32 | 8 | 32 | >32 | 2 | 0.125 |
| 202 | clavulanate | 1 | 4 | 8 | 4 | 16 | 2 | 0.5 | 0.125 |
| 203 | clavulanate | 1 | 2 | 32 | 4 | 32 | 1 | 0.25 | 8 |
| 204 | clavulanate | 1 | 2 | 32 | 4 | 8 | 2 | 0.25 | 8 |
| 205 | clavulanate | 1 | 2 | 16 | 4 | 16 | 0.5 | 0.5 | 2 |
| 206 | clavulanate | 1 | 4 | >32 | 4 | 8 | 0.25 | 4 | 0.125 |
| 301 | clavulanate | 1 | 8 | >32 | 4 | 16 | 1 | 0.25 | 0.125 |
| 302 | clavulanate | 1 | >32 | >32 | 4 | 32 | 2 | 0.25 | 0.125 |
| 303 | clavulanate | 1 | >32 | >32 | 4 | 32 | 2 | 0.5 | 0.125 |
| 304 | clavulanate | 1 | >32 | >32 | 4 | 32 | 1 | 0.25 | 0.125 |
| 305 | clavulanate | 1 | >32 | >32 | 4 | 4 | 4 | 0.25 | 0.25 |
| 306 | clavulanate | 1 | >32 | >32 | 4 | 32 | 2 | 0.5 | 0.25 |
| 307 | clavulanate | 1 | >32 | >32 | 8 | 32 | 2 | 0.25 | 0.125 |
| 308 | clavulanate | 1 | >32 | >32 | 4 | 16 | 0.5 | 0.5 | 0.125 |
| 309 | clavulanate | 1 | >32 | >32 | 4 | 32 | 2 | 0.5 | 0.125 |
| 310 | clavulanate | 1 | >32 | 16 | 4 | 4 | 2 | 0.5 | 0.125 |
| 311 | clavulanate | 1 | 4 | >32 | 4 | 8 | 0.5 | 0.25 | 0.125 |
| 312 | clavulanate | 1 | >32 | >32 | 8 | 8 | 4 | 0.5 | 0.125 |
| 313 | clavulanate | 1 | 4 | >32 | 4 | 16 | 0.5 | 0.25 | 0.125 |
| 314 | clavulanate | 1 | 4 | >32 | 4 | 32 | 1 | 0.25 | 0.125 |
| 315 | clavulanate | 1 | 4 | >32 | 4 | 8 | 1 | 0.25 | 0.125 |
| 316 | clavulanate | 1 | 16 | 32 | 4 | 8 | 0.5 | 0.25 | 0.125 |
| 317 | clavulanate | 1 | 16 | >32 | 8 | 8 | 0.5 | 0.25 | 0.125 |
| 318 | clavulanate | 1 | 16 | >32 | 4 | >32 | 0.5 | 0.25 | 0.125 |
| 319 | clavulanate | 1 | >32 | >32 | 4 | 16 | 0.25 | 0.25 | 0.125 |
| 320 | clavulanate | 1 | >32 | >32 | 8 | 8 | 0.5 | 0.25 | 0.125 |
| 321 | clavulanate | 1 | 16 | >32 | 4 | >32 | 1 | 0.25 | 0.125 |
| 322 | clavulanate | 1 | 16 | >32 | 8 | >32 | 0.125 | 1 | 0.125 |
| 323 | clavulanate | 1 | 16 | 16 | 8 | 4 | 2 | 0.25 | 0.125 |
| 324 | clavulanate | 1 | 32 | 8 | 8 | 4 | 1 | 1 | 0.125 |
| 325 | clavulanate | 1 | 4 | 16 | 4 | 4 | >32 | 0.25 | 0.125 |
| 326 | clavulanate | 1 | 4 | 32 | 4 | 8 | >32 | 0.125 | 0.125 |
| 327 | clavulanate | 1 | 2 | >32 | 2 | 32 | 2 | 0.25 | 0.125 |
| 328 | clavulanate | 1 | 8 | 32 | 4 | 4 | 1 | 1 | 0.125 |
| 331 | clavulanate | 1 | >32 | >32 | 4 | 4 | 0.5 | 2 | 0.125 |
| 332 | clavulanate | 1 | >32 | 16 | 4 | 16 | 1 | 2 | 0.125 |
| 333 | clavulanate | 1 | >32 | 32 | 4 | 32 | 1 | 0.25 | 0.125 |
| 401 | clavulanate | 1 | 4 | >32 | 8 | 16 | 0.5 | 0.125 | 0.125 |
| 402 | clavulanate | 1 | 8 | 32 | 4 | 32 | <0.06 | 0.25 | <0.06 |
| 403 | clavulanate | 1 | 8 | >32 | 2 | 32 | 4 | 0.5 | 0.125 |

TABLE 5-continued

Activity of compounds of general formula II in representative combinations

| Bridged Monobactam of formula II | Supplementary β-lactamase inhibitor of formula V or VI | Antibiotic of formula I | MIC of antibiotic at fixed inhibitor concentration (4 mg/L) | | | | | | |
|---|---|---|---|---|---|---|---|---|---|
| | | | Acinetobacter sp. J2 | Pseudomonas aeruginosa MK1184 | Pseudomonas aeruginosa 1973E | Enterobacter cloacae P99 | Klebsiella pneumoniae CF104 | Serratia marcescens S6 | Stenotrophomonas malthophilia 1AC736 |
| 404 | clavulanate | 1 | 4 | >32 | 4 | 16 | 0.5 | 0.25 | 0.25 |
| 406 | clavulanate | 1 | >32 | 32 | 8 | 32 | 2 | 0.5 | 0.125 |
| 407 | clavulanate | 1 | >32 | >32 | 8 | 32 | 1 | 0.5 | 0.125 |
| 408 | clavulanate | 1 | >32 | >32 | 16 | 32 | 2 | 0.5 | 0.125 |

Further objects of the invention according to the following paragraphs 1-2 are also disclosed herein:

1. A pharmaceutical composition, comprising a combination of a) an antibiotically active compound of the following formula I:

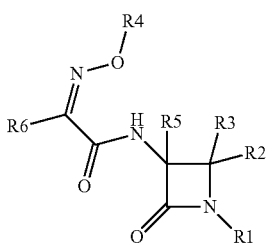

in which
R1 signifies SO$_3$H, OSO$_3$H, CRaRa'COOH, OCRaRa'COOH, 5-tetra-zolyl, SO$_2$NHRb or CONHRc,
  wherein Ra and Ra' are independently selected from hydrogen; alkyl; allyl; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; alkylamino; dialkylamino; alkoxyalkyl and a 5-6 membered heteroaromatic ring which may be substituted with 1 to 4 substituents selected from alkyl, hydroxyl, alkoxy, amino, alkylamino, dialkylamino and halogen;
  wherein Rb is hydrogen; alkyl; alkoxycarbonyl; alkylaminocarbonyl; benzylaminocarbonyl in which the benzyl may be substituted with 1 to 5 substituents selected from alkyl, hydroxyl, alkoxy, amino, alkylamino, dialkylamino and halogen; or phenylaminocarbonyl in which the phenyl may be substituted with 1 to 5 substituents selected from alkyl, hydroxyl, alkoxy, amino, alkylamino, dialkylamino and halogen;
  wherein Rc is hydrogen; alkyl; phenyl which may be substituted with 1 to 5 substituents selected from alkyl, hydroxyl, alkoxy, amino, alkylamino, dialkylamino and halogen; benzyl which may be substituted with 1 to 5 substituents selected from alkyl, hydroxyl, alkoxy, amino, alkylamino, dialkylamino and halogen; alkoxycarbonyl; SO$_2$phenyl; SO$_2$NHalkyl; or a 5-6 membered heteroaromatic ring which may be substituted with 1 to 4 substituents selected from alkyl, hydroxyl, alkoxy, amino, alkylamino, dialkylamino and halogen;
R2 and R3 independently signify hydrogen; alkyl; alkenyl; alkynyl; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; azido; halogen; dihalogenomethyl; trihalogenomethyl; alkoxycarbonyl; carboxyl; sulfonyl or CH$_2$X1,
  wherein X1 is azido; amino; halogen; hydroxyl; cyano; carboxyl; aminosulfonyl; alkoxycarbonyl; alkanoylamino; phenylaminocarbonyl; alkylaminocarbonyl; aminocarbonyl; carbamoyloxy; alkylaminosulfonyl; phenylaminosulfonyl in which the phenyl may be substituted with 1 to 5 substituents selected from alkyl, hydroxyl, alkoxy, amino, alkylamino, dialkylamino and halogen; phenyl which may be substituted with 1 to 5 substituents selected from alkyl, hydroxyl, alkoxy, amino, alkylamino, dialkylamino and halogen; or which may be substituted with 1 to 5 substituents selected from alkyl, hydroxyl, alkoxy, amino, alkylamino, dialkylamino and halogen;
R4 signifies hydrogen; alkyl; C(Rx)(Ry)Z,
  wherein Rx and Ry are independently selected from hydrogen; alkyl; allyl; (C$_3$-C$_6$)cycloalkyl; phenyl which may be substituted with 1 to 5 substituents selected from alkyl, hydroxyl, alkoxy, amino, alkylamino, dialkylamino and halogen; (C$_2$-C$_7$) alkene and (C$_2$-C$_7$)alkyne; or Rx and Ry taken together may form an alkylene bridge —(CH$_2$)$_n$— with n being an integer number from 2 to 6; and
Z is COOH; CH$_2$N(OH)COR' wherein
  R' is hydrogen, alkyl, alkylamino, alkoxy, benzyl which may be substituted with 1 to 5 substituents selected from alkyl, hydroxyl, alkoxy, amino, alkylamino, dialkylamino and halogen, phenyl which may be substituted with 1 to 5 substituents selected from alkyl, hydroxyl, alkoxy, amino, alkylamino, dialkylamino and halogen, or a 5-6 membered heteroaromatic ring which may be substituted with 1 to 4 substituents selected from alkyl, hydroxyl, alkoxy, amino, alkylamino, dialkylamino and halogen;
or Z is one of the following six groups

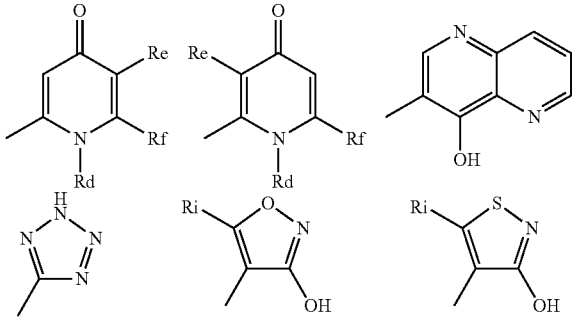

in which groups
Rd, Re and Rf are independently selected from hydrogen; alkyl; amino; monoalkylamino; carboxyaminoalkyl;

alkoxycarbonyl; benzyl which may be substituted with 1 to 5 substituents selected from alkyl, hydroxyl, alkoxy, amino, alkylamino, dialkylamino and halogen; diphenylmethyl; trityl; and ORg wherein Rg is hydrogen; alkyl; benzyl which may be substituted with 1 to 5 substituents selected from alkyl, hydroxyl, alkoxy, amino, alkylamino and halogen; or phenyl which may be substituted with 1 to 5 substituents selected from alkyl, hydroxyl, alkoxy, amino, alkylamino and halogen;

or, when Re and Rf are vicinal substituents, Re and Rf taken together may also be —O—CH=CH—CH$_2$—, —O—CH$_2$—CH$_2$—O—, —CH$_2$—CH$_2$—CH$_2$—, —CH$_2$—CH$_2$—CH$_2$—CH$_2$—, —CH=CH—CH=CH— or —CH=C(OH)—C(OH)=CH—;

Ri is hydrogen; alkyl; alkylamino; alkoxy; benzyl which may be substituted with 1 to 5 substituents selected from alkyl, hydroxyl, alkoxy, amino, alkylamino, dialkylamino and halogen; phenyl which may be substituted with 1 to 5 substituents selected from alkyl and hydroxyl; or a 5-6 membered heteroaromatic ring which may be substituted with 1 to 5 substituents selected from alkyl, hydroxyl, alkoxyalkoxy, amino, alkylamino, dialkylamino and halogen;

R5 signifies hydrogen, alkyl, halogenomethyl, dihalogenomethyl, trihalogenomethyl, alkoxy, formylamino or alkylcarbonylamino;

R6 signifies phenyl which may be substituted with 1 to 5 substituents selected from alkyl, hydroxyl, alkoxyalkoxy, amino, alkylamino, dialkylamino and halogen; or a 5-6 membered heteroaromatic ring which may be substituted with 1 to 4 substituents selected from alkyl, hydroxyl, alkoxy, amino, alkylamino, carbonylamino and halogen; or a pharmaceutically acceptable salt thereof;

with a β-lactamase inhibitor of one of the following groups b1) to b11):

b1) a bridged monobactam derivative of the following formula II:

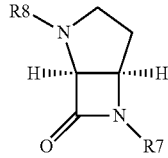

in which:

R7 signifies SO$_3$H, OSO$_3$H or OCRjRj'COOH, wherein Rj and Rj' are independently selected from hydrogen; alkyl; phenyl which may be substituted with 1 to 5 substituents selected from alkyl, hydroxyl, alkoxyalkoxy, amino, alkylamino, dialkylamino and halogen; benzyl which may be substituted with 1 to 5 substituents selected from alkyl, hydroxyl, alkoxyalkoxy, amino, alkylamino, dialkylamino and halogen; alkylamino and alkoxyalkyl;

R8 is alkoxycarbonylamino, the acyl residue of an α or β amino acid, or a residue of the formula Q-(X)$_r$—Y—, wherein Q is a 3-6 membered ring which optionally contains nitrogen, sulphur and/or oxygen and which is optionally fused to a phenyl ring or to a 5-6 membered heterocyclic ring and which is optionally substituted with 1 to 4 substituents selected from alkyl, allyl, hydroxyl, alkoxyalkoxy, amino, alkylamino, dialkylamino, carboxamide which may be substituted, carboxylic acid, carbonylalkoxy, aminocarbonyl, alkylaminocarbonyl, halogen, halogenomethyl, dihalogenomethyl, trihalogenomethyl, sulfamide, substituted sulfamide with substituents selected from alkyl, allyl, phenyl which may be substituted with 1 to 5 substituents selected from alkyl, hydroxyl, alkoxyalkoxy, amino, alkylamino and halogen and benzyl which may be substituted with 1 to 5 substituents selected from alkyl, hydroxyl, alkoxyalkoxy, amino, alkylamino, halogen and benzyl, urea which may be substituted with alkyl, aminoalkyl, alkoxyalkyl or aminoalkoxyalkyl, and carbamate which may be substituted with alkyl, aminoalkyl, alkoxyalkyl or aminoalkoxyalkyl, X signifies a linear spacer of from 1 to 6 atoms length and containing carbon, nitrogen, oxygen and/or sulphur atoms, of which up to 2 atoms can be nitrogen atoms and 1 atom can be oxygen or sulphur, r is an integer of from 0 to 1; and Y is selected from —CO—, —CS—, —NHCO—, —NHCONH— and —SO$_2$—;

or a pharmaceutically acceptable salt thereof, or b2) a monobactam derivative of the general formula III:

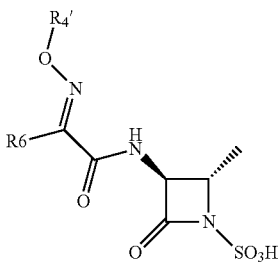

in which

R4' signifies hydrogen, alkyl or CH(Rx')Z', wherein

Rx' is selected from hydrogen; (C$_1$-C$_6$)alkyl; allyl; phenyl and (C$_3$-C$_6$)cycloalkyl; and Z' signifies COOH or a group of one of the following two formulae:

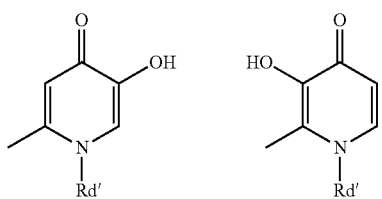

in which Rd' is hydrogen or hydroxy; and

R6 is as defined for formula I; or a pharmaceutically acceptable salt thereof;

or b3) a penam sulfone derivative of the general formulae IV or V:

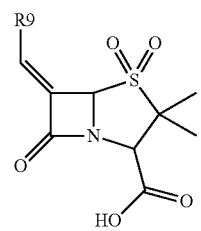

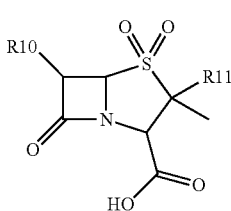

in which
R9 signifies COOH or a 5-6 membered monocyclic or polycyclic heteroaromatic group;
R10 signifies hydrogen or halogen;
R11 signifies CH₂R12; CH=CHR12 wherein R12 is hydrogen, halogen, cyano, carboxylic acid, acyl such as acetyl, carboxamide which may be substituted, alkoxycarbonyl or a 5-6 membered heteroaromatic ring which is optionally substituted with 1 to 5 substituents selected from alkyl, hydroxyl, alkoxy, amino, alkylamino, dialkylamino and halogen; or which is optionally fused with a 5-6 membered heteroaromatic ring; CH=NR12' wherein R12' is amino, alkylamino, dialkylamino, aminocarbonyl, acylamino such as acetylamino, hydroxy, alkoxy,
or a pharmaceutically acceptable salt thereof;
or
b4) an oxapenam derivative of the general formula VI:

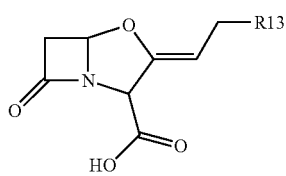

in which
R13 signifies OR14; S(O)ₙR14 or a 5-6 membered heteroaromatic ring which may be substituted with 1 to 5 substituents selected from alkyl, hydroxyl, alkoxy, amino, alkylamino, dialkylamino and halogen; whereby n=0, 1 or 2, and R14 is hydrogen, alkyl, (C₂-C₇)alkene, (C₂-C₇)alkyne or a 5-6 membered heteroaromatic ring which may be substituted with 1 to 5 substituents selected from alkyl, hydroxyl, alkoxy, amino, alkylamino, dialkylamino and halogen,
or a pharmaceutically acceptable salt thereof;
or
b5) a penem derivative of the general formula VII:

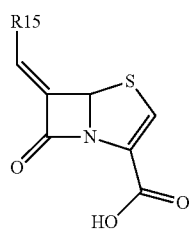

in which
R15 signifies a 5-6 membered heteroaromatic ring which may be substituted with 1 to 5 substituents selected from alkyl, hydroxyl, alkoxy, amino, alkylamino, dialkylamino and halogen; or which is optionally fused with a 5-6 membered heteroaromatic ring and/or which is optionally bound to the exo-methylene group over a —CH=CH— spacer being preferably in the (E)-configuration,
or a pharmaceutically acceptable salt thereof;
or
b6) a cephem sulfone derivative of the general formula VIII:

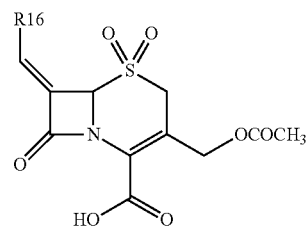

in which
R16 signifies COOR17, whereby R17 signifies hydrogen or alkyl; or a 5-6 membered heteroaromatic ring which is optionally fused with a 5-6 membered heteroaromatic ring being optionally substituted with 1 to 5 substituents selected from alkyl, hydroxyl, alkoxy, amino, alkylamino, dialkylamino, halogen; and/or being optionally bound to the exo-methylene group over a —CH=CH— spacer being preferably in the (E)-configuration,
or a pharmaceutically acceptable salt thereof;
or
b7) a carbapenem derivative of the general formula IX:

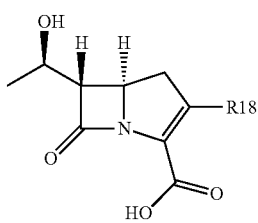

in which R18 signifies —S-alkyl, —S—(CH₂)₂—NH—CH=NH or a group of the following two formulae

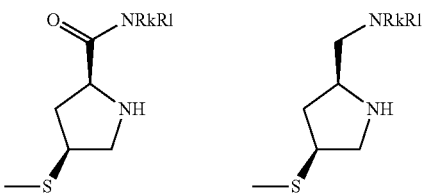

wherein Rk and Rl are individually selected from hydrogen, alkyl, 2-, 3-, 4-carboxyphenyl and sulfamoyl, or a pharmaceutically acceptable salt thereof;
or
b8) a boronate derivative of the general formula X:

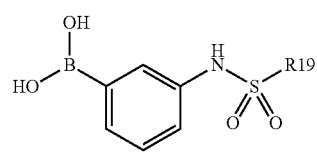

wherein R19 signifies a 5-6 membered heteroaromatic ring which may be substituted with amino, alkylamino, dialkylamino or alkylsulfoxide, or a pharmaceutically acceptable salt thereof;
or
b9) a boronate derivative of the general formula XI:

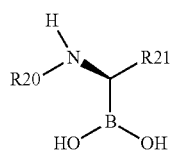

XI wherein
R20 and 21 are independently selected from a 5-6 membered heteroaromatic ring; phenyl which may be substituted with 1 to 5 substituents selected from alkyl, hydroxyl, alkoxy, amino, alkylamino, dialkylamino and halogen and benzyl which may be substituted with 1 to 5 substituents selected from alkyl, hydroxyl, alkoxy, amino, alkylamino, dialkylamino and halogen,
or a pharmaceutically acceptable salt thereof;
or
b10) a phosphonate derivative of the general formula XII:

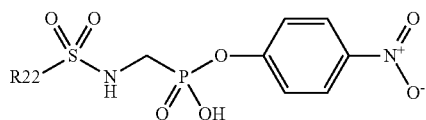

XII wherein
R22 is selected from a 5-6 membered heteroaromatic ring which may be substituted with 1 to 5 substituents selected from alkyl, hydroxyl, alkoxy, amino, alkylamino, dialkylamino and halogen and which is optionally fused with a 5-6 membered heteroaromatic ring; phenyl which may be substituted with 1 to 5 substituents selected from alkyl, hydroxyl, alkoxy, amino, alkylamino, dialkylamino and halogen; and benzyl which may be substituted with 1 to 5 substituents selected from alkyl, hydroxyl, alkoxy, amino, alkylamino, dialkylamino and halogen,
or a pharmaceutically acceptable salt thereof;
or
b11) a diazabicyclooctane derivative of the general formula XIII:

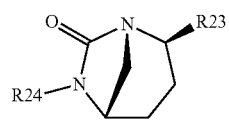

XIII in which
R23 signifies hydrogen, carboxylic acid, alkoxycarbonyl or carboxamide which may be substituted, and
R24 signifies $SO_3H$, $OSO_3H$ or $OCRjRj'COOH$, wherein Rj and Rj' are as defined for formula II,
or a pharmaceutically acceptable salt thereof.
2. Any embodiment as disclosed in the following claims 2 to 5, with their dependency or reference to claim 1 being replaced by a reference to preceding paragraph 1.

The invention claimed is:
1. A compound of the following formula Ia:

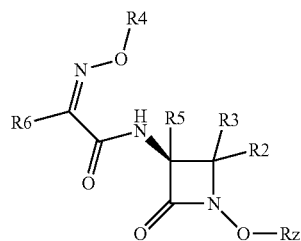

Ia in which
Rz is $SO_3H$
R2 and R3 are alkyl;
R4 is $CH_2Z$, with Z having the formula

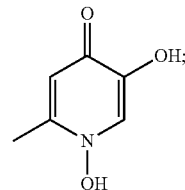

R5 signifies hydrogen, alkyl, halogenomethyl, dihalogenomethyl, trihalogenomethyl, alkoxy, formylamino or alkylcarbonylamino;
R6 signifies phenyl which may be substituted with 1 to 5 substituents selected from the group consisting of alkyl, hydroxyl, alkoxy, amino, alkylamino, dialkylamino and halogen; or a 5-6 membered heteroaromatic ring which may be substituted with 1 to 4 substituents selected from the group consisting of alkyl, hydroxyl, alkoxy, amino, alkylamino, carbonylamino and halogen;
or a pharmaceutically acceptable salt or inner salt of said compound.

2. The compound of claim 1, wherein R6 is an optionally amino-substituted and optionally chloro-substituted 5-6-membered heteroaromatic ring or pharmaceutically acceptable salt or inner salts of said compound.

3. The compound of claim 1, wherein R5 is hydrogen or a pharmaceutically acceptable salt or inner salt of said compound.

4. The compound of claim 2, wherein R6 is selected from the group consisting of 2-amino-1,3-thiazol-4-yl, 5-amino-1,2,4-thiadiazol-3-yl, 5-amino-1,2,4-oxadiazol-3-yl, 3-aminoisoxazol-5-yl, 5-amino-1-methylpyrazol-3-yl, 5-aminopyrazol-3-yl, 6-amino-2-pyridyl, 4-aminopyrimidin-2-yl, 2-carbonylamino-1,3-thiazol-4-yl, 2-amino-5-chloro-1,3-thiazol-4-yl and 2-thienyl; or a pharmaceutically acceptable salt or inner thereof of said compound.

5. A pharmaceutical composition comprising a compound claim 1 or a pharmaceutically acceptable salt or inner salt of said compound.

6. A compound of the following formula Ia:

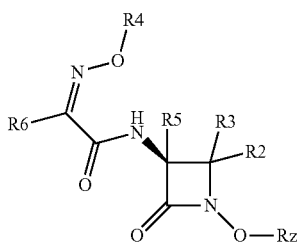

in which
Rz is SO$_3$H;
R2 and R3 are methyl;
R4 is CH$_2$Z, with Z having the formula

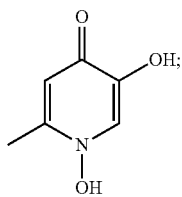

R5 is hydrogen;
R6 is an amino-substituted and optionally chloro-substituted 5-membered heteroaromatic ring;
or a pharmaceutically acceptable salt or inner salt of said compound.

7. The compound of claim 6 wherein R6 is selected from the group consisting of 2-amino-1,3-thiazol-4-yl, 5-amino-1,2,4-thiadiazol-3-yl, 5-amino-1,2,4-oxadiazol-3-yl, 3-aminoisoxazol-5-yl and 2-amino-5-chloro-1,3-thiazol-4-yl;
or a pharmaceutically acceptable salt or inner salt of said compound.

8. The compound of claim 7 wherein R6 is 2-amino-1,3-thiazol-4-yl, 5-amino-1,2,4-thiadiazol-3-yl or 2-amino-5-chloro-1,3-thiazol-4-yl;
or a pharmaceutically acceptable salt or inner salt of said compound.

9. The compound of claim 7 wherein R6 is 2-amino-1,3-thiazol-4-yl;
or a pharmaceutically acceptable salt or inner salt of said compound.

10. The compound of claim 7 wherein R6 is 2-amino-5-chloro-1,3-thiazol-4-yl;
or a pharmaceutically acceptable salt or inner salt of said compound.

11. The compound of claim 7 wherein R6 is 5-amino-1,2,4-thiadiazol-3-yl;
or a pharmaceutically acceptable salt or inner salt of said compound.

12. A pharmaceutical composition comprising a compound claim 6 or a pharmaceutically acceptable salt or inner salt of said compound.

* * * * *